United States Patent [19]

Taniguchi et al.

[11] Patent Number: 5,710,150
[45] Date of Patent: Jan. 20, 1998

[54] BENZAZEPINE DERIVATIVE, PHARMACEUTICAL COMPOSITION THEREOF, AND INTERMEDIATE THEREOF

[75] Inventors: Nobuaki Taniguchi; Akihiro Tanaka; Akira Matsuhisa; Ken-ichiro Sakamoto; Hiroyuki Koshio; Takeyuki Yatsu, all of Ibaraki, Japan

[73] Assignee: Yamanouchi Pharmaceutical Co., Ltd., Tokyo, Japan

[21] Appl. No.: 607,217

[22] Filed: Feb. 26, 1996

Related U.S. Application Data

[63] Continuation of PCT/JP94/01409 Aug. 25, 1994.

[30] Foreign Application Priority Data

Aug. 26, 1993 [JP] Japan ................................. 5-211589
Jan. 14, 1994 [JP] Japan ................................. 6-002341

[51] Int. Cl.$^6$ .......................... C07D 223/16; A61K 31/55
[52] U.S. Cl. .......................... 514/213; 540/480; 540/544; 540/575; 540/553; 540/593
[58] Field of Search .......................... 540/593, 480, 540/544, 553, 575; 514/213

[56] References Cited

U.S. PATENT DOCUMENTS 5,244,898  9/1993  Ogawa et al. .................... 514/213

*Primary Examiner*—Mukund J. Shah
*Assistant Examiner*—Deepak R. Rao
*Attorney, Agent, or Firm*—Sughrue, Mion, Zinn, Macpeak & Seas, PLLC

[57] ABSTRACT

Benzazepine derivatives represented by the following general formula (I) useful as arginine vasopressin antagonists or pharmaceutically acceptable salts thereof, pharmaceutical compositions thereof, and difluorobenzazepinone derivatives represented by the following general formulae (II) and (III) which are useful as production intermediates of the compound (I).

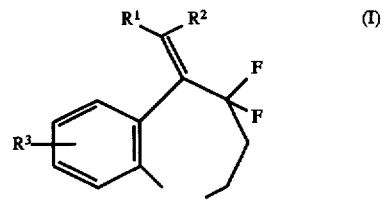

(I)

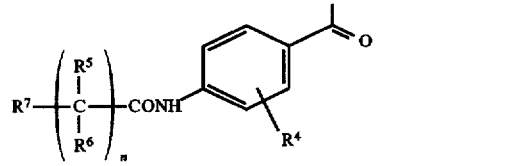

(II)

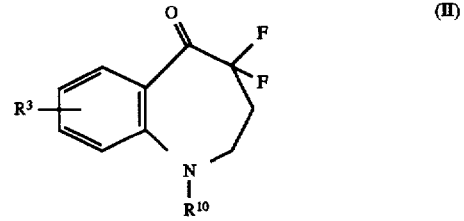

(III)

13 Claims, No Drawings

BENZAZEPINE DERIVATIVE, PHARMACEUTICAL COMPOSITION THEREOF, AND INTERMEDIATE THEREOF

This is a continuing application of PCT/JP94/01409, filed Aug. 25, 1994.

TECHNICAL FIELD

This invention relates to novel benzazepine derivatives which are useful as arginine vasopressin antagonists, to pharmaceutically acceptable salts thereof, to pharmaceutical compositions which contain these compounds as active ingredients and to intermediates for the synthesis of these compounds.

BACKGROUND ART

Arginine vasopressin (AVP) is a peptide consisting of 9 amino acid residues, which is synthesized and secreted in the hypothalamo-neurohypophyseal system. As antagonists for the arginine vasopressin, peptide type compounds and non-peptide type compounds have been synthesized. For example, a compound disclosed in an unexamined published Japanese patent application (Kokai) No. 2-32098 is known as the peptide type compound. On the other hand, 2,3,4,5-tetrahydro-1H-1-benzazepine derivatives represented by the following general formula have been disclosed in EP-A-0514667 and an unexamined published Japanese patent application (Kokai) No. 5-132466 as non-peptide type vasopressin antagonists.

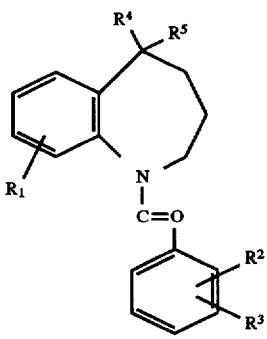

(In the above formula, $R^4$: . . . . . . . . . ., a lower alkoxycarbonyl-substituted alkylidene group, a (lower alkyl)amino-lower alkylidene group, a cyano lower alkylidene group, . . . . . .; see the aforementioned patent publication as to other symbols.)

Also, International Patent Publication No. 91/05549 disclosing the compound represented by the following general formula and 2,3,4,5-tetrahydro-1H-1-benzazepine derivatives described in an unexamined published Japanese patent application (Kokai) No. 4-154765 are known.

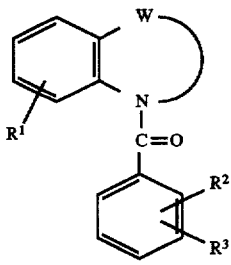

(In the above formula,

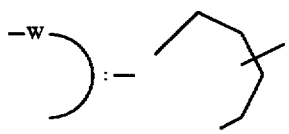

substituent . . . . . .; substituent group: . . . . . . oxo group, hydroxyimino group, alkylidene group, . . . . . .; see aforementioned patent publications as to other symbols.)

In addition, the inventors of the present invention have previously found arginine vasopressin antagonism in the following benzoylaminobenzoyl-1,2,3,4-tetrahydro-1H-1-benzazepine derivative and filed a patent application (of an unexamined published Japanese patent application 5-320135).

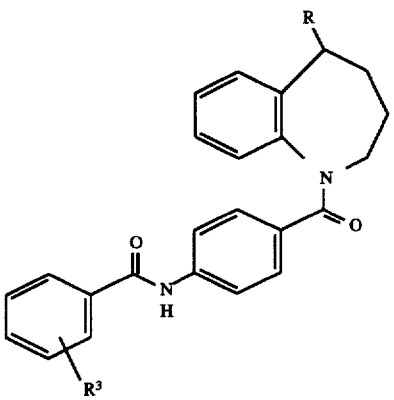

(In the above formula, R: . . . . . . . . ;

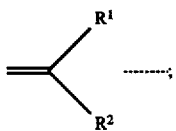

$R^1$ and $R^2$: one is hydrogen atom and the other is a lower alkoxy group, a lower alkoxycarbonyl group or phenyl group; see the aforementioned patent publication as to other symbols.)

The (substituted)methylidene-substituted benzazepine derivatives disclosed in these patent publications show isomerization from exo-olefin to endo-olefin under acidic or basic conditions. Particularly, It is known that a compound having an electron attractive group at the α-position is apt to undergo such an isomerization. In consequence, these compounds are not only difficult to synthesize due to isomerization but also insufficient in terms of handling or stability in vivo because of their inferior physical stability.

DISCLOSURE OF THE INVENTION

The inventors of the present invention have conducted extensive studies on compounds having arginine vasopressin antagonism and accomplished the present invention based on the finding that a novel benzazepine derivative represented by the following general formula (I) unexpectedly shows stable and excellent arginine vasopressin antagonism.

Accordingly, the present invention relates to a benzazepine derivative represented by the following general formula (I) or a pharmaceutically acceptable salt thereof.

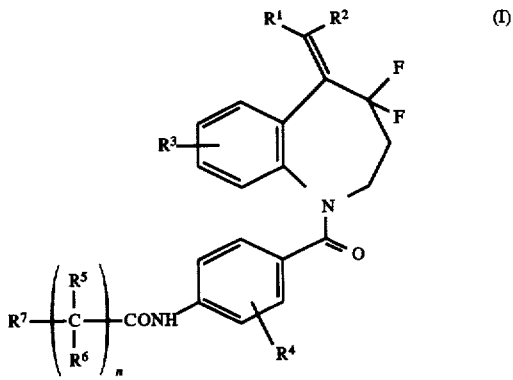

[Symbols in the formula have the following meanings; $R^1$ and $R^2$: one of them represents a hydrogen atom and the other represents a group represented by

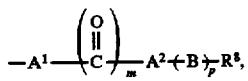

$A^1$ and $A^2$: these may be the same or different from each other and each represents a single bond, a lower alkylene group or a lower alkenylene group, m: 0 or 1, B: a group represented by

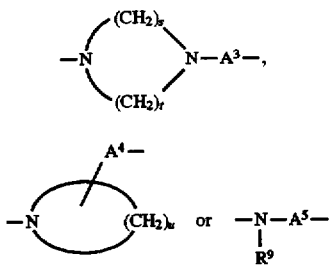

(nitrogen atoms in these formulae may be oxidized), p: 0 or an integer of from 1 to 3 (provided that, when p is 2 or 3, the groups defined by B may be the same or optionally different), $R^8$: a hydrogen atom; a lower alkyl group; a lower alkenyl group; a cycloalkyl group; a hydroxyl group; a lower alkoxy group; a carboxyl group; a lower alkoxycarbonyl group; a cyano group; an aryl group which may be substituted; a nitrogen-containing aromatic five- or six-membered heterocyclic group which may be substituted; a nitrogen-containing saturated five- to eight-membered heterocyclic group which may have a bridge and which may be substituted with a lower alkyl group on the nitrogen atom of the ring; or a group represented by

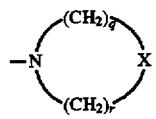

(the nitrogen atom in the formula may be oxidized), s and t: these may be the same or different from each other and each is an integer of 1 to 3 (provided that the total number of s and t is an integer of from 3 to 5), u: an integer of from 2 to 7, $A^3$, $A^4$ and $A^5$: these may be the same or different from one another and each represents a single bond, a lower alkylene group or a lower alkenylene group (provided that, when the adjacent group is linked to $A^3$ or $A^5$ via a nitrogen atom or oxygen atom, $A^3$ or $A^5$ is a group other than single bond ), $R^9$: a hydrogen atom or a lower alkyl group, q and r: these may be the same or different from each other and each is an integer of from 1 to 3 (provided that the total number of q and r is an integer of from 3 to 5), X: a group represented by —O— or —S(O)$_w$—, w: 0, 1 or 2, $R^3$ and $R^4$: these may be the same or different from each other and each represents a hydrogen atom; a halogen atom; a lower alkyl group; a lower alkoxy group; or an amino group which may be substituted with a lower alkyl group, $R^5$ and $R^6$: these may be the same or different from each other and each represents a hydrogen atom or a lower alkyl group ($R^5$ and $R^6$ may be combined to mean a lower alkylene group to form a saturated carbon ring with adjacent carbon atoms), n: 0 or 1, and $R^7$: an aryl group which may be substituted or an aromatic five- or six-membered heterocyclic group which may be substituted.]

The present invention also relates to a pharmaceutical composition, especially an arginine vasopressin antagonizing agent, which contains the compound represented by the aforementioned general formula (I) or a pharmaceutically acceptable salt thereof as an active ingredient.

The present invention also relates to difluorobenzazepinone derivatives represented by the following general formulae (II) and (III) or salts thereof, which are useful as intermediates for the production of the compound represented by the aforementioned general formula (I) or a pharmaceutically acceptable salt thereof.

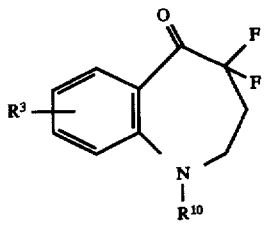

(In the formula, $R^3$ is as defined in the foregoing and $R^{10}$ represents a hydrogen atom or a protecting group for the amino group.)

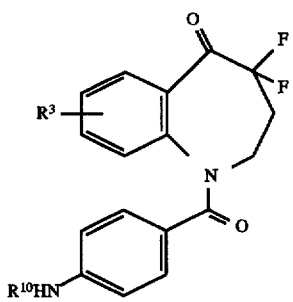

(III)

(In the formula, $R^3$ and $R^{10}$ are as defined above.)

Chemical structure of the compound of the present invention is characterized in that a difluoro group is linked to a ring carbon atom adjacent to the carbon atom in the azeping ring on which a (substituted) methylidene group is substituted. Because of the possession of difluoro group, the compound of the present invention does not undergo isomerization and shows sufficient stability and excellent persistency in the living body. Moreover, it exerts excellent arginine vasopressin antagonism. Particularly, a compound in which the methylidene group is substituted with a (substituted) aminocarbonyl group has excellent arginine vasopressin antagonism. In addition, the compound of the present invention is excellent in oral absorption property.

The following describes the compound of the present invention in detail.

Illustrative examples of the heterocyclic group moiety of the "aromatic five- or six-membered heterocyclic group which may be substituted" represented by $R^7$ of the compound of the present invention include a nitrogen-containing aromatic five- or six-membered heterocyclic group which contains at least one nitrogen atom as a hetero atom and may have an oxygen or sulfur atom, such as a pyrrolyl group, a pyrazolyl group, an imidazolyl group, a triazolyl group, a tetrazolyl group, a pyridyl group, a pyridazyl group, a pyrimidinyl group, a pyrazinyl group, a thiazolyl group, an isothiazolyl group, an oxazolyl group, an isoxazolyl group or the like, and an aromatic five- or six-membered heterocyclic group which contains an oxygen atom and/or a sulfur atom as a hetero atom, such as a thienyl group, a furyl group, a pyranyl group or the like.

The heterocyclic group moiety of the "nitrogen-containing aromatic five- or six-membered heterocyclic group which may be substituted" represented by $R^8$ is a nitrogen-containing aromatic five- or six-membered heterocyclic group which contains at least one nitrogen atom as a hetero atom and may have an oxygen atom and/or a sulfur atom, and its illustrative examples include those cited above as illustrative examples of the nitrogen-containing five- or six-membered heterocyclic group.

Illustrative examples of the heterocyclic group moiety of the "nitrogen-containing saturated five- to eight-membered heterocyclic group which may have a bridge and which may be substituted with a lower alkyl group on the nitrogen atom of the ring" represented by $R^8$ include monocyclic or bridged saturated heterocyclic groups which contain a nitrogen atom as the hetero atom, such as a pyrrolidinyl group, a piperidinyl group, a piperazinyl group, a pyrazolidinyl group, an imidazolidinyl group, a homopiperazinyl group (a hexahydrodiazepinyl group), an azocanyl group, an azabicyclo[2.2.2]octyl groups

(a quinuclidinyl group),

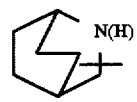

(a 2-azabicyclo[2.2.2]octyl group) and the like], an azabicyclo[2.2.1]heptyl groups

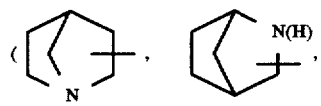

and the like), an azabicyclo[3.2.1]octyl groups

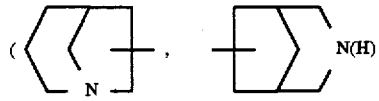

and the like), an azabicyclo[3.3.1]nonyl groups

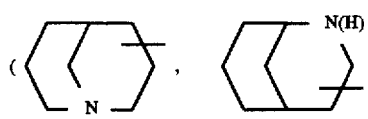

and the like), and an azabicyclo[3.2.2]nonyl groups

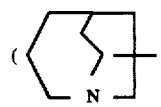

and the like). In these rings, (H) means that this position may have a hydrogen atom or a substituent or a connecting arm which will be described later.

In addition, examples of the aryl group moiety of the "aryl group which may be substituted" represented by $R^7$ and $R^8$ include aryl groups having 6 to 14 carbon atoms, such as a phenyl group, a biphenyl group, a naphthyl group, an anthryl group, a phenanthoryl group and the like.

The substituents to be located on the aromatic five- or six-membered heterocyclic group, nitrogen-containing aromatic five- or six-membered heterocyclic group or aryl ring ef the aforementioned groups $R^7$ and $R^8$ may be selected from those which are commonly used in the art as substituents on aromatic heterocyclic rings or aryl rings. These rings may have 1 or 2 or more substituents which are the same or different from one another.

Preferred examples of these substituents include a) a lower alkyl, lower alkenyl or lower alkynyl group which may be substituted with a halogen atom or a hydroxyl group, b) a lower alkoxy group which may be substituted with a halogen atom, a cyano group, a hydroxyl group, a carboxyl group, a lower alkoxycarbonyl group, a lower alkanoyl group, a lower alkanoyloxy group, a carbamoyl group, a lower alkylaminocarbonyl group or a phthalimide group; a hydroxyl group; a mercapto group; or a lower alkylthio group, c) a halogen atom, a cyano group, or a nitro group, d) a carboxyl group; a lower alkoxycarbonyl group; a lower alkanoyl group; a lower alkanoyloxy group; a carbamoyl group; or a lower alkylaminocarbonyl group, e) an amino group which may be substituted with a lower alkyl group; a lower alkanoylamino group; a 1-pyrrodinyl group; a piperidino group; a morpholino group; or a piperazinyl, imidazolidinyl or homopiperazinyl group which groups may be substituted with a lower alkyl group on the nitrogen atom of the ring, f) a cycloalkyl group, g) a phenyl group which may be substituted with a lower alkyl group, a lower alkenyl group, a lower alkynyl group, a halogen atom, a lower alkoxy group, an amino group which may be substituted with a lower alkyl group, a hydroxyl group or a carboxyl group, and h) an imidazolyl, triazolyl, tetrazolyl, pyrrolyl, pyridyl, pyrazinyl or pyrimidinyl group, which may be substituted with a lower alkyl group, a cycloalkyl group or a phenyl group.

Particularly preferred examples of the substituents on the aromatic five-or six-membered heterocyclic group, nitrogen-containing aromatic five- or six-membered heterocyclic group and an aryl group of $R^8$ include a halogen atom, a lower alkyl group, a lower alkoxy group and an amino group which may be substituted with a lower alkyl group.

With regard to the substituent of the aryl group of $R^7$, all of the aforementioned groups may be used as preferred substituents when the aryl group is phenyl, and a lower alkyl group may be used as a preferred substituent when the aryl group is naphthyl or the like.

Unless otherwise noted, the term "lower" as used in the definition of the general formula of the present invention means a straight or branched carbon chain having 1 to 6 carbon atoms.

Illustrative examples of the "lower alkyl group" include straight or branched alkyl groups each having 1 to 6 carbon atoms, such as methyl, ethyl, propyl, isopropyl, butyl, isobutyl, sec-butyl, tert-butyl, pentyl, isopentyl, neopentyl, tert-pentyl, 1-methylbutyl, 2-methylbutyl, 1,2-dimethylpropyl, hexyl, isohexyl, 1-methylpentyl, 2-methylpentyl, 3-methylpentyl, 1,1-dimethylbutyl, 1,2-dimethylbutyl, 2,2-dimethylbutyl, 1,3-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl, 1-ethyl-2-methylpropyl and the like.

Illustrative examples of the "lower alkenyl group" include straight or branched alkenyl groups each having 2 to 6 carbon atoms, such as vinyl, allyl, 1-propenyl, isopropenyl, 1-butenyl, 2-butenyl, 3-butenyl, 2-methyl-1-propenyl, 2-methylallyl, 1-methyl-1-propenyl, 1-methylallyl, 1-pentenyl, 2-pentenyl, 3-pentenyl, 4-pentenyl, 3-methyl-1-butenyl, 3-methyl-2-butenyl, 3-methyl-3-butenyl, 2-methyl-1-butenyl, 2-methyl-2-butenyl, 2-methyl-3-butenyl, 1-methyl-1-butenyl, 1-methyl-2-butenyl, 1-methyl-3-butenyl, 1,1-dimethylallyl, 1,2-dimethyl-1-propenyl, 1,2-dimethyl-2-propenyl, 1-ethyl-1-propenyl, 1-ethyl-2-propenyl, 1-hexenyl, 2-hexenyl, 3-hexenyl, 4-hexenyl, 5-hexenyl, 1,1-dimethyl-1-butenyl, 1,1-dimethyl-2-butenyl, 1,1-dimethyl-3-butenyl, 3,3-dimethyl-1-butenyl, 1-methyl-1-pentenyl, 1-methyl-2-pentenyl, 1-methyl-3-pentenyl, 1-methyl-4-pentenyl, 4-methyl-1-pentenyl, 4-methyl-2-pentenyl, 4-methyl-3-pentenyl and the like.

Illustrative examples of the "lower alkynyl group" include straight or branched alkynyl groups each having 2 to 6 carbon atoms, such as ethynyl, 1-propynyl, 2-propynyl, 1-butynyl, 2-butynyl, 3-butynyl, 1-methyl-2-propynyl, 1-pentynyl, 2-pentynyl, 3-pentynyl, 4-pentynyl, 3-methyl-1-butynyl, 2-methyl-3-butynyl, 1-methyl-2-butynyl, 1-methyl-3-butynyl, 1,1-dimethyl-2-propynyl, 1-hexynyl, 2-hexynyl, 3-hexynyl, 4-hexynyl, 5-hexynyl and the like.

Illustrative examples of the "cycloalkyl group" include cycloalkyl groups preferably having 3 to 8 carbon atoms, such as cyclopropyl, cyclobutyl, cyclopentyl, cyclohexyl, cycloheptyl, cyclooctyl and the like.

Illustrative examples of the "lower alkoxy group" include lower alkoxy groups having the aforementioned lower alkyl group as its alkyl moiety, such as methoxy, ethoxy, propoxy, isopropoxy, butoxy, isobutoxy, sec-butoxy, tertbutoxy, pentyloxy (amyloxy), isopentyloxy, tert-pentyloxy, neopentyloxy, 2-methylbutoxy, 1,2-dimethylpropoxy, 1-ethylpropoxy, hexyloxy and the like.

Illustrative examples of the "lower alkylthio group" include lower alkylthio groups having the aforementioned lower alkyl group as its alkyl moiety, such as methylthio, ethylthio, propylthio, isopropylthio, butylthio, isobutylthio, pentylthio, isopentylthio, hexylthio, isohexylthio and the like.

Illustrative examples of the "lower alkanoyl group" include lower acyl groups of 1 to 6 carbon atoms derived from saturated aliphatic carboxylic acids, such as formyl, acetyl, propionyl, bytylyl, isobutylyl, valeryl, isovaleryl, pivaloyl, hexanoyl and the like.

Illustrative examples of the "lower alkanoyloxy group" include those groups which contain the aforementioned lower alkanoyl group as the alkanoyl moiety, such as acetoxy, propionyloxy and the like.

Examples of the "halogen atom" include fluorine, chlorine, bromine and iodine.

The term "amino group which may be substituted with a lower alkyl group" means an amino group or an amino group mono- or di-substituted with the aforementioned lower alkyl group, and its illustrative examples including mono-lower alkylamino groups such as methylamino, ethylamino, propylamino, isopropylamino, butylamino, isobutylamino, sec-butylamino, tert-butylamino, pentyl(amyl)amino, isopentylamino, neopentylamino, tert-pentylamino, hexylamino and the like and symmetric or asymmetric di-lower alkylamino groups such as dimethylamino, diethylamino, dipropylamino, diisopropylamino, dibutylamino, diisobutylamino, ethylmethylamino, methylpropylamino and the like.

The "lower alkoxycarbonyl group" is a lower alkoxycarbonyl group having the aforementioned lower alkyl group as its alkyl moiety, which is formed by the esterification of a straight- or branched-chain alcohol having 1 to 6 carbon atoms with a carbonyl group, such as methoxycarbonyl, ethoxycarbonyl, propoxycarbonyl, isopropoxycarbonyl, butoxycarbonyl, isobutoxycarbonyl, sec-butoxycarbonyl, tert-butoxycarbonyl, pentyloxycarbonyl, isopentyloxycarbonyl, neopentyloxycarbonyl, tert-pentyloxycarbonyl, hexyloxycarbonyl or the like.

In the same manner, the "lower alkylaminocarbonyl group" is a lower alkylaminocarbonyl group having an amino group substituted with the aforementioned lower alkyl group in its alkylamino moiety.

The term "lower alkylene group" means a straight or branched divalent carbon chain having 1 to 6 carbon atoms, with its illustrative examples including methylene, methylmethylene, ethylene, trimethylene, tetramethylene, 2-methyltrimethylene, 1-ethylethylene, pentamethylene, 1,2-diethylethylene, hexamethylene and the like.

The term "lower alkenylene group" means a straight or branched divalent carbon chain having 2 to 6 carbon atoms, with its illustrative examples including vinylene, propenylene, 2-propenylene, 1-methylvinylene, 2-methylvinylene, butenylene, 2-butenylene, 3-butenylene, 1-methylpropenylene, 1-methyl-2-propenylene, 2-pentenylene, 1-methyl-1-butenylene, 2-hexenylene and the like.

Illustrative examples of the "protecting group for amino group" include urethane-type protecting groups such as benzyloxycarbonyl, tert-butoxycarbonyl, tert-amyloxycarbonyl and the like which may be substituted with a lower alkyl group, a lower alkoxy group, a halogen atom, nitro group, phenylazo group or p-phenylazo group; acyl-type protecting groups such as formyl, acetyl, trifluoroacetyl, benzoyl and the like; aralkyl-type protecting groups such as benzyl, benzhydryl, trityl and the like; organic sulfonyl-type protecting groups such as alkanesulfonyl (e.g., methanesulfonyl, ethanesulfonyl, and trifluoromethanesulfonyl) and aromatic sulfonyl (e.g., benzenesulfonyl and toluenesulfonyl (particularly p-toluenesulfonyl)); and silyl-type protecting groups such as trimethylsilyl, triisopropylsilyl and tert-butyldimethylsilyl.

The salt of the compound of the present invention may be an acid addition salt with an inorganic or organic acid or a salt with an inorganic or organic base, and a pharmaceutically acceptable salt is preferable. Illustrative examples of such salts include: an acid addition salt with a mineral acid such as hydrochloric acid, hydrobromic acid, hydroiodic acid, sulfuric acid, nitric acid, phosphoric acid or the like, with an organic acid such as formic acid, acetic acid, propionic acid, oxalic acid, malonic acid, succinic acid, fumaric acid, maleic acid, lactic acid, malic acid, tartaric acid, citric acid, methanesulfonic acid, ethanesulfonic acid or the like or with an acidic amino acid such as aspartic acid, glutamic acid or the like; and a salt with an inorganic base such as sodium, potassium, magnesium, calcium, aluminium or the like, with an organic base such as methylamine, ethylamine, ethanolamine or the like or with a basic amino acid such as lysine, ornithine or the like. Also useful are quaternary ammonium salts. Illustrative examples of quaternary ammonium salts include a lower alkyl halide, a lower alkyl trifurate, a lower alkyl tosylate, a benzyl halide and the like, preferably methyl iodide, benzyl chloride and the like.

When the compound of the present invention has a tertiary amine, said amine may be oxidized, and all of such oxide derivatives are included herein.

The compound of the general formula (I) may form optical isomers due to the asymmetric carbon atom, geometrical isomers due to the double bond or cyclohexane ring or endo-exo stereoisomers due to the ring having a bridge. Mixtures and separated forms of various isomers including such geometrical isomers and optical isomers are also included in the scope of the present invention. Also included in the present invention are hydrates, various solyates, tautomers and the like of the compound of general formula (I). All types of polymorphism of the inventive compound are also included in the present invention.

A preferred example of the compound (I) of the present invention is a compound, or a pharmaceutically acceptable salt thereof, wherein the group represented by

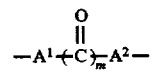

is selected from
1) a single bond,
2) a group of formula

3) a lower alkylene group or a lower alkenylene group, or
4) a group of formula

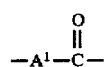

($A^1$ is a lower alkylene group or a lower alkenylene group), and $R^8$ is a hydrogen atom; a cyano group; a carboxyl group; a lower alkoxycarbonyl group; a lower alkyl group; a lower alkenyl group; a cycloalkyl group; a hydroxyl group; a lower alkoxy group; a phenyl or naphthyl group which may be substituted with a lower alkyl group, a halogen atom, an amino group which may be substituted with a lower alkyl group, or a lower alkoxy group; a nitrogen-containing aromatic five- or six-membered heterocyclic group which is selected from a pyridyl group, an imidazolyl group, a pyrazinyl group, a pyrimidinyl group, a pyridazinyl group, a pyrazolyl group, a pyrrolyl group, a tetrazolyl group, a triazolyl group, a thiazolyl group and an oxazolyl group and which may be substituted with a lower alkyl group, a halogen atom, an amino group which may be substituted with a lower alkyl group, or a lower alkoxy group; a nitrogen-containing saturated five- to eight-membered heterocyclic group which is selected from a pyrrolidinyl group, a piperidyl group, a piperazinyl group, an imidazolidinyl group, a homopiperazinyl group, a pyrazolidinyl group, an azabicyclo[2.2.2]octyl group, an azabicyclo[2.2.1]heptyl group and an azabicyclo[3.2.1]octyl and which may have a bridge and which may be substituted with a lower alkyl group on the nitrogen atom of the ring; or a group represented by

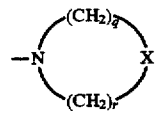

(N atom in the formula may be oxidized) (wherein q and r: 1, 2 or 3 and q+r=3 to 5, X: O or $S(O)_w$, w: 0, 1 or 2), and $R^7$ is phenyl group which may have 1 to 5 substituents; a naphthyl group which may be substituted with a lower alkyl group; or an aromatic five- or six-membered heterocyclic group which is selected from a thienyl group, a furyl group, a pyrrolyl group, a pyridyl group, an imidazolyl group, a pyrazinyl group, a pyrimidinyl group, a pyranyl group, a pyridazinyl group, a pyrazolyl group, a tetrazolyl group, a triazolyl group, a thiazolyl group, an isothiazolyl group, an oxazolyl group and an isoxazolyl group, and which may be substituted with a lower alkyl group, a halogen atom, an amino group which may be substituted with a lower alkyl group, or a lower alkoxy group; in which each of the substituents for the phenyl group for $R^7$ is selected from:

a) a lower alkyl, lower alkenyl or lower alkynyl group which may be substituted with a halogen atom or a hydroxyl group, b) a lower alkoxy group which may be substituted with a halogen atom, a cyano group, a hydroxyl group, a carboxyl group, a lower alkoxycarbonyl group, a lower alkanoyl group, a lower alkanoyloxy group, a carbamoyl group, a lower alkylaminocarbonyl group or a phthalimide group; a hydroxyl group; a mercapto group; or a lower alkylthio group, c) a halogen atom, a cyano group, or a nitro group, d) a carboxyl group; a lower alkoxycarbonyl group; a lower alkanoyl group; a lower alkanoyloxy group; a carbamoyl group; or a lower alkylaminocarbonyl group, e) an amino group which may be substituted with a lower alkyl group; a lower alkanoylamino group; a 1-pyrrolidinyl group; a piperidino group; a morpholino group; or a piperazinyl, imidazolidinyl or homopiperazinyl group which groups may be substituted with a lower alkyl group on the nitrogen atom of the ring, f) a cycloalkyl group, g) a phenyl group which may be substituted with a lower alkyl group, a lower alkenyl group, a lower alkynyl group, a halogen atom, a lower alkoxy group, an amino group which may be substituted with a lower alkyl group, a hydroxyl group or a carboxyl group, and h) an imidazolyl, triazolyl, tetrazolyl, pyrrolyl, pyridyl, pyrazinyl or pyrimidinyl group, which groups may be substituted with a lower alkyl group, a cycloalkyl group or a phenyl group. Further preferable compound is a compound or a pharmaceutically acceptable salt thereof, wherein the group represented by

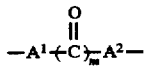

is selected from
1) a single bond,
2)

or
3) a lower alkylene group or a lower alkenylene group, and
$R^8$ is a hydrogen atom; a cyano group; a carboxyl group; a lower alkoxycarbonyl group; a lower alkyl group; a lower alkenyl group; a cycloalkyl group; a hydroxyl group; a lower alkoxy group; a phenyl group which may be substituted with a lower alkly group or a halogen atom; a nitrogen-containing aromatic five- or six-membered heterocyclic group which is selected from a pyridyl group, an imidazolyl group, a triazolyl group, a thiazolyl group and an oxazolyl group and which may be substituted with a lower alkyl group or with an amino group which may be substituted with a lower alkyl group; a nitrogen-containing saturated five- to eight-membered heterocyclic group which is selected from a pyrrolidinyl, a piperidyl group, a homopiperazinyl group, an azabicyclo[2.2.2]octyl group and an azabicyclo[3.2.1]octyl group, which may have a bridge, and which may be substituted with a lower alkyl group on the nitrogen atom of the ring; or a group represented by

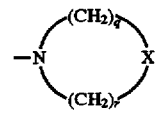

(N atom in the formula may be oxidized) (wherein q and r: 1, 2 or 3 and q+r=3 to 5, X: O or $S(O)_w$, w: 0, 1 or 2), and
$R^7$ is a phenyl group which may have 1 to 5 substituents; a naphthyl group; or an aromatic five- or six-membered heterocyclic group which is selected from a thienyl group, a furyl group, a pyrrolyl group, a pyridyl group, an imidazolyl group, a triazolyl group, a thiazolyl group and an oxazolyl group and which may be substituted with a lower alkyl group; in which each of the substituents for the phenyl group of $R^7$ is selected from:

a) a lower alkyl, lower alkenyl or lower alkynyl group, which groups may be substituted with a halogen atom or a hydroxyl group, b) a lower alkoxy group which may be substituted with a hydroxyl group, a carboxyl group or a carbamoyl group; or a lower alkylthio group, c) a halogen atom, or a nitro group, e) an amino group which may be substituted with a lower alkyl group; a 1-pyrrolidinyl group; a piperidino group; a morpholino group; or a piperazinyl or homopiperazinyl group which groups may be substituted with a lower alkyl group on the nitrogen atom of the ring, g) a phenyl group which may be substituted with a lower alkyl group, a lower alkoxy group, an amino group which may be substituted with a lower alkyl group, or a hydroxyl group, and h) an imidazolyl, triazolyl or pyrrolyl group, which groups may be substituted with a lower alkyl group, a cycloalkyl group or a phenyl group. More preferable compound is a compound or a pharmaceutically acceptable salt thereof, wherein when the group represented by

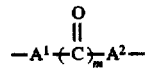

is
1) a single bond, then
p is 0, and $R^8$ is a cyano group, a carboxyl group or a lower alkoxycarbonyl group, or
2)

or 3) a lower alkylene group or a lower alkenylene group, then
p is 0, 1 or 2, and
$R^8$ is a hydrogen atom; a lower alkyl group; a lower alkenyl group; a hydroxyl group; a lower alkoxy group; a cycloalkyl group; a phenyl group which may be substituted with a lower alkly group or a halogen atom;

a nitrogen-containing aromatic five- or six-membered heterocyclic group which is selected from a pyridyl group, an imidazolyl group, a triazolyl group, a tiazoryl group and an oxazolyl group and which may be substituted with a lower alkyl group or with an amino group which may be substituted with a lower alkyl group; a nitrogen-containing saturated five- to eight-membered heterocyclic group which is selected from a pyrrolidinyl group, a piperidyl group, a homopiperazinyl group, an azabicyclo[2.2.2]octyl group and an azabicyclo[3.2.1]octyl group, which may have a bridge, and which may be substituted with a lower alkyl group on the nitrogen atom of the ring; or
a group represented by

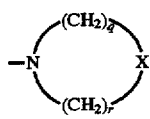

(N atom in the formula may be oxidized) (wherein q and r: 1, 2 or 3 and q+r=3 to 5, X: O or S(O)$_w$, w: 0, 1 or 2), with the proviso that, when

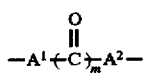

is

and p=0, R$^8$ represents

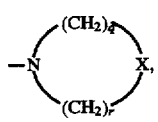

and when

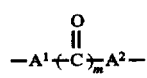

is a lower alkylene group and p=0, R$^8$ represents a hydroxyl group. Most preferable compound is a compound or a pharmaceutically acceptable salt thereof, wherein
1) when the group represented by

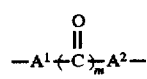

is a single bond, then

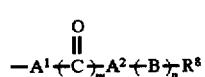

is
(1) —R$^{8a}$ (wherein R$^{8a}$ is a cyano group, a carboxyl group or a lower alkoxycarbonyl group), 2) when the group represented by

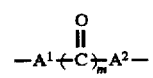

is

then

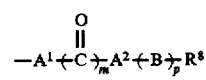

is

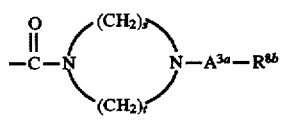 (2-1)

(wherein s$^a$ and t$^a$: 1, 2 or 3, s$^a$t$^a$=3 to 5,

A$^{3a}$: a single bond or a lower alkylene group, and

R$^{8b}$: a hydrogen atom, a lower alkyl group or a phenyl group),

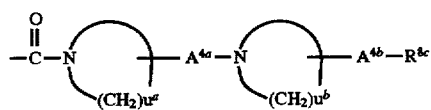 (2-2)

(wherein u$^a$ and u$^b$: 4, 5 or 6,

A$^{4a}$ and A$^{4b}$: each is a single bond, and

R$^{8c}$: a hydrogen atom),

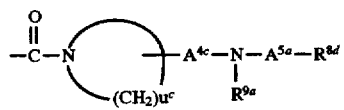 (2-3)

(wherein u$^c$: 4, 5 or 6,

A$^{4c}$ and A$^{5a}$: each is a single bond, and

R$^{9a}$ and R$^{8d}$: the same or different from each other and each represents a lower alkyl group),

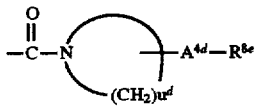 (2-4)

(wherein u$^d$: 4, 5 or 6,

A$^{4d}$: a single bond, and $R^{8e}$: a hydrogen atom),

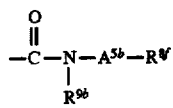
(2-5)

(wherein $R^{9b}$: a hydrogen atom or a lower alkyl group, $A^{5b}$: a single bond or a lower alkylene group, and $R^{8f}$: a hydrogen atom, a cycloalkyl group, a phenyl group, a pyridyl group, a piperidyl group which may be substituted with a lower alkyl group on the nitrogen atom of the ring, a quinuclidinyl group, a hydroxyl group, a lower alkoxy group or a lower alkyl group),

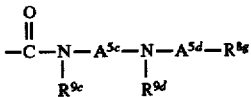
(2-6)

(wherein $A^{5c}$: a lower alkylene group, $A^{5d}$: a single bond, $R^{9c}$ and $R^{9d}$: the same or different from each other and each represents hydrogen atom or a lower alkyl group, and $R^{8g}$: a hydrogen atom or a lower alkyl group), or

(2-7)

$R^{8h}$: a group represented by a formula

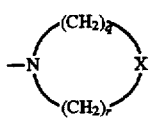

(wherein q and r: 1, 2 or 3 and q+r=3 to 5, X: O or S(O)$_w$, and w: 0, 1 or 2), or 3) when the group represented by

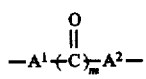

is a lower alkylene group or a lower alkenylene group, then

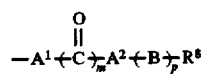

represents

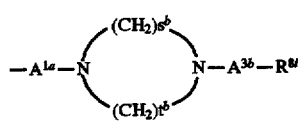
(3-1)

(wherein $A^{1a}$: a lower alkylene group, $s^b$ and $t^b$: 1, 2 or 3, $s^b+t^b$: 3 to 5, $A^{3b}$: a single bond, and $R^{8i}$: a hydrogen atom or a lower alkyl group),

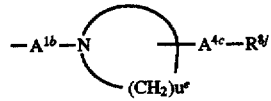
(3-2)

(wherein $A^{1b}$: a lower alkylene group $u^e$: 4, 5 or 6, $A^{4c}$: a single bond, and $R^{8j}$: a hydrogen atom),

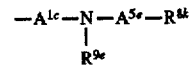
(3-3)

(wherein $A^{1c}$: a lower alkylene group, $R^{8k}$ and $R^{9e}$: a hydrogen atom or a lower alkyl group, and $A^{5e}$: a single bond), or (3-4) —$A^{1d}$—$R^{8l}$ (wherein $A^{1d}$: a lower alkylene group, and $R^{8l}$: a hydroxyl group).

Particularly preferred is a compound or a pharmaceutically acceptable salt thereof wherein $R^7$ is a phenyl group which may be substituted with 1 to 3 substituents each selected from a lower alkyl group which may be substituted with a halogen atom, a lower alkoxy group which may be substituted with a carbamoyl group, a halogen atom, a piperidino group, a phenyl group which may be substituted with a lower alkyl group, an imidazolyl, triazolyl, or pyrrolyl group which groups may be substituted with a lower alkyl group; a naphthyl group; or a thienyl, furyl or pyrrolyl group which groups may be substituted with a lower alkyl group, more preferably a compound wherein the group represented by the formula

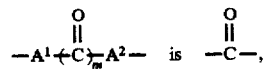

or a pharmaceutically acceptable salt thereof, particularly the Z form thereof and its pharmaceutically acceptable salt.

Illustrative examples of particularly superior compounds are shown in the following.

(1) 4'-[[4,4-Difluoro-5-(4-methyl-1-piperazinyl) carbonylmethylene-2,3,4,5-tetrahydro-1H-1-benzazepin-1-yl]carbonyl]-2-phenylbenzanilide or a pharmaceutitally acceptable salt thereof (particularly its Z form).

(2) 4'-[[4,4-Difluoro-5-[(1-piperazinylcarbonyl)methylene] 2,3,4,5-tetrahydro-1H-1-benzazepin-1-yl]carbonyl]-2-phenylbenzanilide or a pharmaceutitally acceptable salt thereof (particularly its Z form).

(3) 4'-[[4,4-Difluoro-5-[[(4dimethylaminopiperidino) carbonyl]methylene]-2,3,4,5-tetrahydro-1H-1-benzazepin-1-yl]carbonyl]-2-phenylbenzanilide or a pharmaceutitally acceptable salt thereof (particularly its Z form).

(4) 4'-[[4,4-Difluoro-5-[[(4-methylhexahydro-1,4-diazepin-1yl)carbonyl]methylene]-2,3,4,5-tetrahydro-1H-1-benzazepin-1-yl]carbonyl]-2-phenylbenzanilide or a pharmaceutitally acceptable salt thereof (particularly its Z form).

(5) 4'-[[5-[[(hexahydro-1,4-Diazepin-1-yl)carbonyl] methylene]-4,4-difluoro-2,3,4,5-tetrahydro-1H-1- benzazepin-1-yl]carbonyl]-2-phenylbenzanilide or a pharmaceutitally acceptable salt thereof (particularly its Z form).

(6) 4'-[[4,4-Difluoro-5-[[N-methyl-N-(1-methyl-4-piperidyl)carbamoyl]methylene]-2,3,4,5-tetrahydro-1H-1-benzazepin-1-yl]carbonyl]-2-phenylbenzanilide or a pharmaceutitally acceptable salt thereof (particularly its Z form).

(7) 4'-[[4,4-Difluoro-5-[[N-(3quinuclidinyl)carbamoyl]methylene]-2,3,4,5-tetrahydro-1H-1-benzazepin-1-yl]carbonyl]-2-phenylbenzanilide or a pharmaceutitally acceptable salt thereof (particularly its Z form and its enantiomer).

(8) N-[4-[[4,4-Difluoro-5-[[(4dimethylaminopiperidino)carbonyl]methylene]-2,3,4,5-tetrahydro-1H-1-benzazepin-1-yl]carbonyl]phenyl]-3-methylthiophene-2-carboxyamide or a pharmaceutitally acceptable salt thereof (particularly its Z form).

(9) 4'-[[4,4-Difluoro-5-(N-isopropylcarbamoylmethylene)-2,3,4,5-tetrahydro-1H-1-benzazepin-1-yl]carbonyl]-2-phenylbenzanilide or a pharmaceutitally acceptable salt thereof (particularly its Z form).

(10) 4'-[[4,4-Difluoro-5-[N-(2-methoxyethyl)carbamoylmethylene]-2,3,4,5-tetrahydro-1H-1-benzazepin-1-yl]carbonyl]-2-phenylbenzanilide or a pharmaceutitally acceptable salt thereof (particularly its Z form).

(11) 4'-[[4,4-Difluoro-5-(N-isopropylcarbamoylmethylene)-2,3,4,5-tetrahydro-1H-1-benzazepin-1-yl]carbonyl]-2-ethoxybenzanilide or a pharmaceutitally acceptable salt thereof (particularly its Z form).

(Production method)

The compound of the present invention and salts thereof can be produced by various synthetic techniques making use of the characteristics of its basic skeleton or the type of substituents. In that case, it may be effective from the viewpoint of production techniques to substitute the carbonyl group of an intermediate compound or the compound of the present invention with an appropriate protecting group, namely a functional group which can be converted easily into a carbonyl group. Protective groups disclosed, for instance, by Greene and Wuts in "Protective Groups in Organic Synthesis", 2nd ed. may be used optionally in accordance with the reaction conditions. In addition to these groups, a hydroxymethylene group (—CH(OH)—) is also a functional group which can be converted easily into a carbonyl group, and such a functional group can also be used as a carbonyl protecting group.

The following describes typical examples of the process for the production of the compound of the present invention.

First Production Process

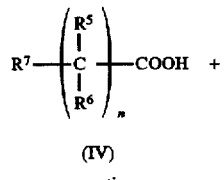

(IV)

or a reactive derivative thereof

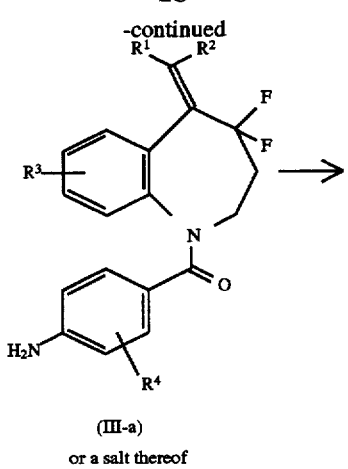

(III-a)

or a salt thereof

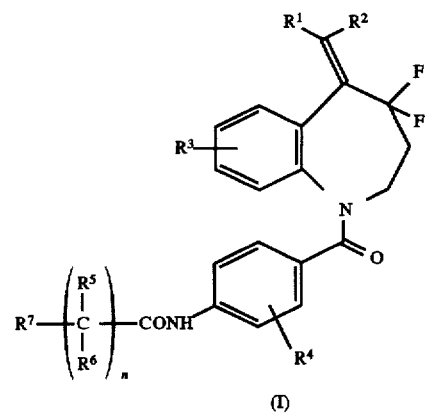

(I)

(In the above formulae, $R^1$, $R^2$, $R^3$, $R^4$, $R^5$, $R^6$, $R^7$ and n are as defined in the foregoing.)

In this production process, the compound (I) of the present invention is produced by subjecting the carboxylic acid represented by the general formula (IV) or a reactive derivative thereof and the substituted aniline represented by the general formula (III-a) or a salt thereof to amidation and, if necessary, removing the protective group.

Examples of the reactive derivative of the compound (IV) include: usual carboxylic acid esters such as methyl ester, ethyl ester, isobutyl ester, tert-butyl ester and the like; its acid halides such as acid chloride, acid bromide and the like; its acid azides; its active esters obtained by allowing it to react with a phenolic compound such as 2,4-dinitrophenol or an N-hydroxylamine compound such as 1-hydroxysuccinimide, 1-hydroxybenzotriazole or the like; its symmetric acid anhydrides; and its mixed acid anhydrides including organic acid-based mixed acid anhydrides obtained by allowing it to react with halocarboxylic acid alkyl esters such as alkylcarbonic acid halides or pivaloyl halides and phosphoric acid-based mixed acid anhydrides obtained by allowing it to react with diphenylphosphoryl chloride or N-methylmorpholine.

Also, when the carboxylic acid is allowed to react as a free acid or without isolating the active ester, it is desirable to use a condensing agent such as dicyclohexylcarbodiimide, carbonyldiimidazole, diphenylphosphoryl azide, diethylphosphoryl cyanide, 1-ethyl-3-(3-dimethylaminopropyl)carbodiimide hydrochloride or the like.

Particularly, according to the present invention, the acid chloride method, a method in which the reaction is carried out in the coexistence of an active esterification agent and a condensing agent or a method in which a usual ester is treated with an amine may be employed advantageously, because such methods can produce the compound of the present invention simply and easily.

Though it varies depending on the reactive derivative, condensing agent and the like to be used, the reaction may be carried out generally in an inert organic solvent selected, for example, from halogenated hydrocarbons such as dichloromethane, dichloroethane, chloroform and the like, aromatic hydrocarbons such as benzene, toluene, xylene and the like, ethers such as ether, tetrahydrofuran and the like, esters such as ethyl acetate and the like, N,N-dimethylformamide and dimethylsulfoxide, and at a cooling temperature or at a temperature of from cooling temperature to room temperature or from room temperature to heating temperature depending on the reactive derivative used.

In order to effect smooth progress of the reaction, it may be advantageous to use the substituted aniline (III-a) in an excess amount or carry out the reaction in the presence of a base such as N-methylmorpholine, trimethylamine, triethylamine, N,N-dimethylaniline, pyridine, 4-(N,N-dimethylamino)pyridine, picoline, lutidine or the like. Pyridine can be used also as a solvent.

Second Production Process

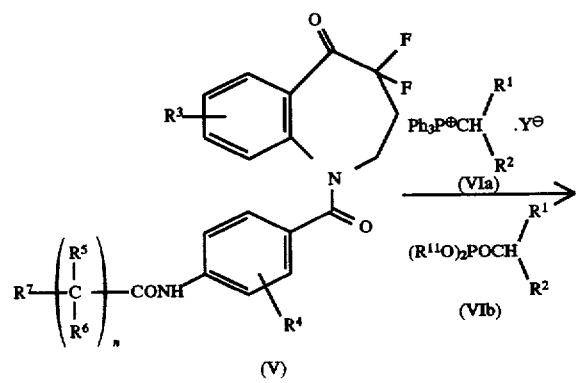

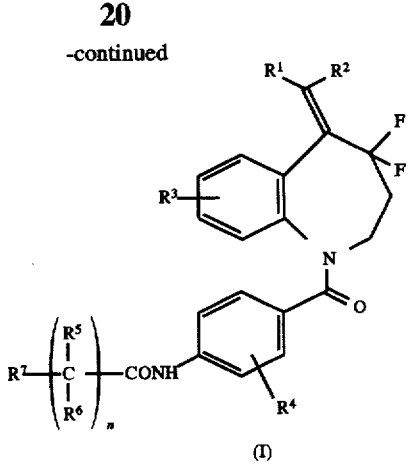

(In the above formulae, Ph represents a phenyl group, Y represents a halogen atom, $R^{11}$ represents a lower alkyl group, and $R^1$, $R^2$, $R^3$, $R^4$, $R^5$, $R^6$, $R^7$ and n are as defined in the foregoing.)

That is, the compound (I) of the present invention can be produced by allowing a compound represented by the general formula (V) to react with a phosphonium salt represented by the general formula (VIa) or a phosphonate represented by the general formula (VIb).

The reaction with the phosphonium salt (VIa) is not particularly limited, provided that it is carried out under the conditions used for the synthesis of olefin by the Wittig reaction, and may be carried out in a reaction solvent such as ether, tetrahydrofuran, benzene, toluene, dichloromethane, chloroform or the like at a temperature of from −78° C. to a heated temperature. In addition, it is desirable to add a base to the reaction system, and examples of such base include inorganic bases such as sodium hydroxide, sodium carbonate and the like, alcolates such as sodium methoxide, sodium ethoxide, potassium tert-butoxide and the like, organic bases such as triethylamine, pyridine and the like and organic metals such as n-butyllithium and the like. The halogen atom represented by Y means chlorine atom, bromine atom or the like.

The reaction with the phosphonate (VIb) is also carried out in an inert solvent such as methanol, ethanol, benzene, toluene, tetrahydrofuran, ether, dimethylformamide, dimethyl sulfoxide or the like in the presence of a base such as sodium hydride, sodium amide, sodium methoxide, sodium ethoxide or the like.

Third Production Process

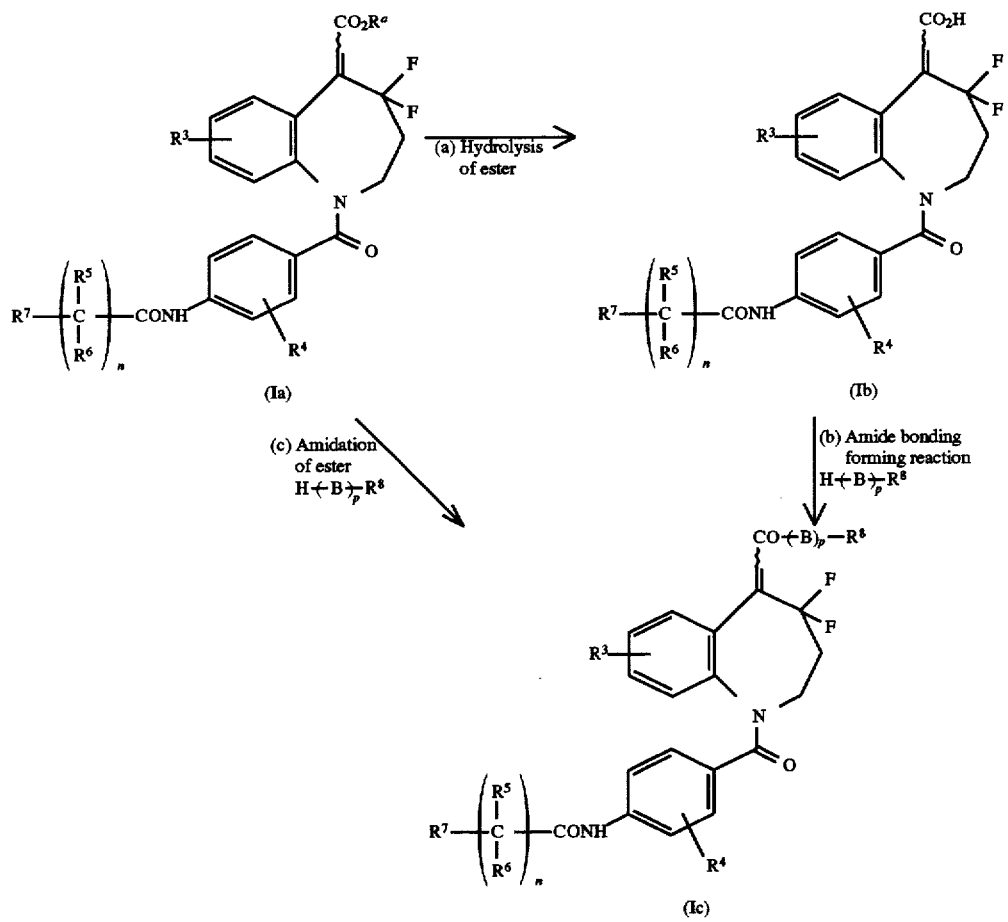

(In the above formulae, $R^a$ represents a lower alkyl group, and $R^1$, $R^2$, $R^3$, $R^4$, $R^5$, $R^6$, $R^7$, n, B, $R^8$ and p are as defined in the foregoing.)

In the third process, a compound of the present invention is converted into other inventive compounds. In the reaction "a", an inventive compound (Ia) in which $R^1$ or $R^2$ is an ester is hydrolyzed to convert it into another inventive compound (Ib) in which $R^1$ or $R^2$ is a carboxylic acid. In the reaction "b", this inventive compound (Ib) is reacted with an amine to form amide bonding, thereby converting it into still another inventive compound (Ic) in which $R^1$ or $R^2$ is an amide. In the reaction "c", the inventive compound (Ia) is reacted with an amine H—(—B—)$_p$—$R^8$ to convert it into the inventive compound (Ic) in which $R^1$ or $R^2$ is an amide.

The reactions "b" and "c" are carried out under the same conditions as those of the amidation reaction of the first production process. In the reaction "a", hydrolysis is carried out in a solvent shown in the first production process or a mixed solvent of alcohol (e.g., methanol and ethanol) with water, in the presence of an appropriate acid or base catalyst with cooling or at a temperature of from cooling temperature to room temperature or from room temperature to a heating temperature.

In this connection, the compounds (IIIa) and (V) as starting compounds of these processes can be obtained easily by a method shown by the following reaction formulae.

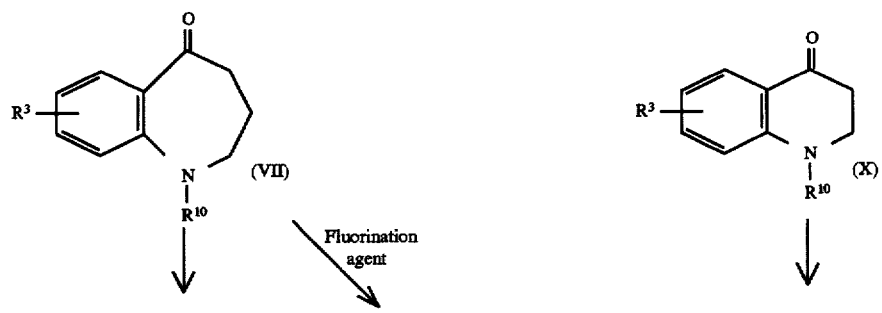

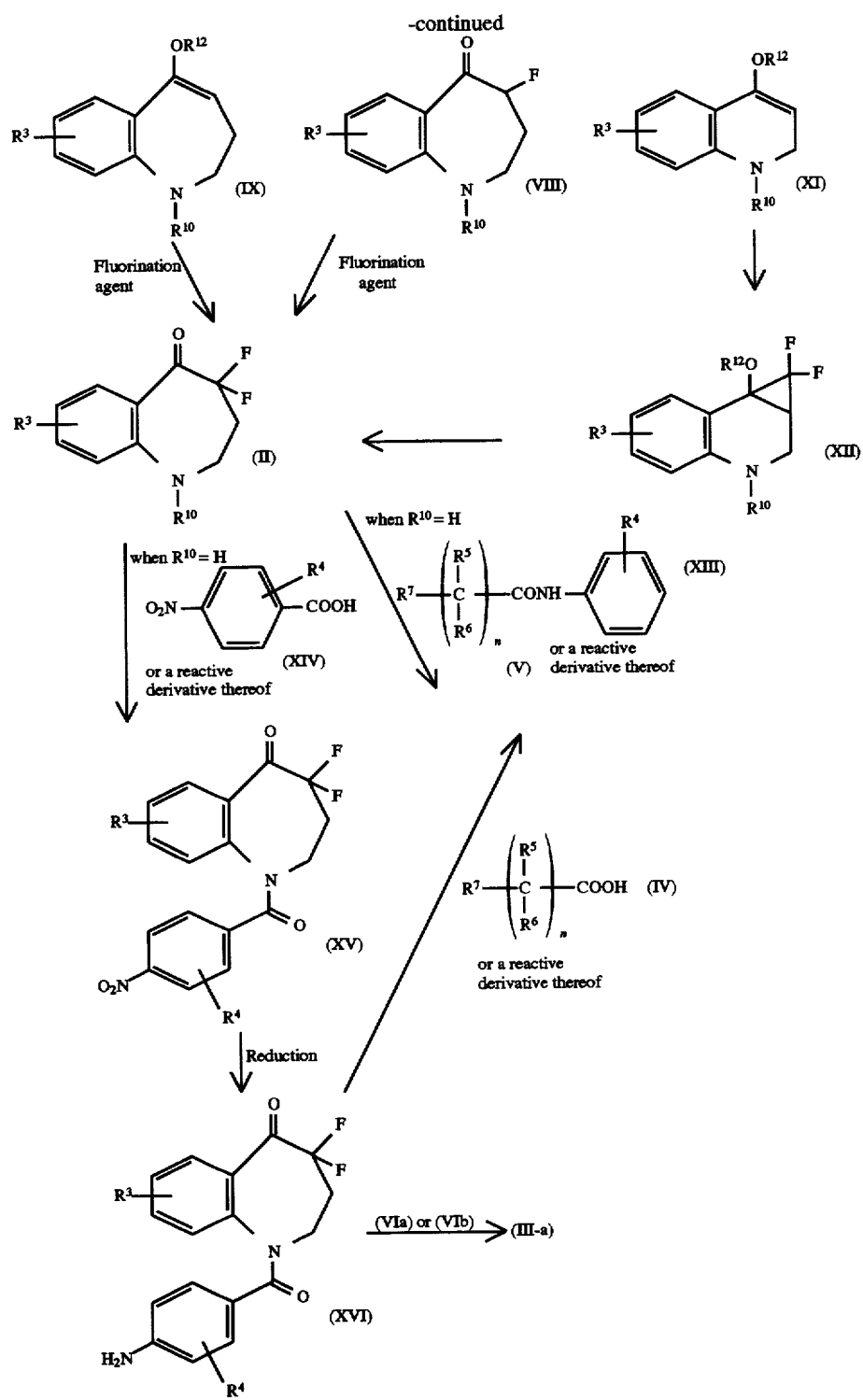

(In the above formulae, $R^1$, $R^2$, $R^3$, $R^4$, $R^5$, $R^6$, $R^7$, $R^{10}$ and n are as defined in the foregoing, and $R^{12}$ is a lower alkyl group or a lower alkanoyl group.)

That is, when the benzazepin-5-one derivative (VII) is used as the starting material, the compound (II) is produced by subjecting the material to stepwise fluorination using a fluorination agent such as N-fluorobenzeneimide and N-fluoropyridinium trifluoromethane sulfonate ((VII)→(VIII) →(II)), or by firstly subjecting it to enol etherification under a basic or acidic condition to obtain a compound (IX) and then directly effecting difluorination of the intermediate using the same fluorination agent ((VII)→(IX) →(II)). When the tetrahydroquinolin-4-one derivative (X) is used as the starting material, the compound (II) is produced in accordance with the method disclosed in Chem. Pharm. Bull., 27 (12), 3123 (1979) in which the material is subjected to enol etherification in the same manner as described above to effect formation of a three-membered ring with difluorocarbene or the like generated from sodium chlorodifluoroacetate and then the ring is enlarged in the presence of a base such as lithium hydroxide or under an acidic condition ((X)→(XI)→(XII)→(II)).

Next, the compound (V) is obtained by converting substituent $R^{10}$ of the thus obtained compound (II) into a hydrogen atom and then effecting amidation of the substituted carbonylaminobenzoic acid (XIII) or a reactive derivative thereof in the same manner as the case of the first production process, or, alternatively, the compound (III-a) can be produced by allowing the compound (II) to deprotection and to react with p-nitrobenzoic acid or a reactive derivative thereof in the same manner as described in the first production process to obtain a 4,4-difluoro-1-(p-nitrobenzoyl)benzdiazepinone derivative (XV) which is subsequently subjected to reduction to obtain a p-aminobenzoylbenzazepine derivative (XVI) and then allowing the latter derivative to react with the compound (VIa) or (VIb) in the same manner as described in the second production process. The other intermediate compound (III) can be produced by introducing a protecting group into the p-aminobenzoylbenzazepine derivative of the compound (III-a).

Also, the compound (V) can be obtained when the compound (XVI) is subjected to amidation with the compound (IV) or a reactive derivative thereof in the same manner as described in the first production process.

These production reactions can be effected by applying usually used methods.

(Other Production Methods)

In addition to the aforementioned production processes, the compound (I) of the present invention can also be produced by the conversion of various substituents.

For example, a compound in which
—$A^1$—$(CO)_m$—$A^2$—$(B)_p$—$R^8$ is not an amide and —$(B)_p$—$R^8$ is an amine-based substituent can be produced by a usual N-alkylation reaction in which a corresponding halide or sulfonate compound is reacted with a corresponding amine, by a method in which a corresponding amide is reduced with an amide reducing agent, or by another conventional method in which a 5-ethylidene-5-hydroxybenzazepine derivative obtained by allowing the compound (V) to react with Grignard's reagent prepared from a vinyl halide is treated with a corresponding amine in the presence of a catalyst. In this connection, such halides and sulfonates can be produced by treating the hydroxy compound obtained in the second production process (also obtainable by reducing the ester, carboxylic acid or aldehyde compound obtained in the third production process) with halogens or sulfonic acids in the usual way. Such production processes are useful particularly for the production of compounds in which $A^1$ or $A^2$ is a lower alkylene group or a lower alkenylene group (e.g., allylamines).

Also, an N-oxide compound can be produced by applying a conventional oxidation method, for example, by treating a corresponding tertiary amine compound with an organic peracid or hydrogen peroxide.

In addition, an aromatic amino compound can be produced by reducing a corresponding nitro compound in the usual way. Also, a compound substituted with a lower alkyl group can be produced by employing the aforementioned conventional N-alkylation reaction, and a compound having a saturated ring can also be produced by using a corresponding dihalide and employing the aforementioned conventional N-alkylation reaction.

The compound of the present invention obtained in this manner is isolated and purified in the form of free compound or its salts, hydrates or various solyates such as solyates with ethanol or a polymorphism compound. Pharmaceutically acceptable salts of the compound (I) can also be produced by subjecting it to conventional salt forming reactions.

Isolation and purification are carried out by applying usual chemical operations such as extraction, fractional crystallization, various types of fractional chromatography and the like.

Various types of isomers can be isolated making use of differences in the physicochemical properties among these isomers.

Each optical isomer can be made into stereochemically pure isomer by the use of proper starting compound or by means of a racemic resolution of racemic compounds (for example, by making them into diastereomer salts with a usual optically active acid or base and then subjecting the salts to optical resolution).

INDUSTRIAL APPLICABILITY

Compounds of the present invention and salts thereof show excellent antagonism on arginine vasopressin $V_1$ and/or $V_2$ receptor. That is, the inventive compounds include a compound which shows strong antagonism on both $V_1$ and $V_2$ receptors, a compound which shows excellent antagonism selectively on $V_1$ receptor and a compound which shows excellent antagonism selectively on $V_2$ receptor.

Particularly preferred is the compound which shows strong antagonism on both $V_1$ and $V_2$ receptors.

The inventive compounds are excellent in oral absorption and show proper prolonged action because of its stability against metabolism in the living body.

In consequence, on the basis of these functions, the inventive compounds show water diuresis action, urea excretion enhancing action, factor VIII secretion inhibiting action, vasodilation action, cardiac function accelerating action, mesangial cell contraction inhibiting action, mesangial cell proliferation inhibiting action, liver gluconeogenesis inhibiting action, platelet aggregation inhibiting action, aldosterone secretion inhibiting action, endotheline production inhibiting action, central blood pressure controlling action, renin secretion controlling action, memory controlling action, thermoregulation action, prostaglandin production controlling action and the like, are useful as characteristic water diuretics, urea excretion enhancers, vasodilators, hypotensive drugs, agents used to treat heart failure and renal failure and blood coagulation inhibitors, and are effective for the prevention and/or treatment of heart failure, hyponatremia, syndrome of inappropriate antidiuretic hormone secretion (SIADH), hypertension, renal diseases (nephrosis, nephritis, diabetic nephropathy, chronic or acute renal failure), edema, brain edema, ascites, hepatic cirrhosis, hypokalemia, water metabolism disorder, diabetes, various ischemic diseases, cerebrovascular disease, cyclothymic failure, gastric ulcer, nausea, vomiting, syncope, renal function disorder and the like and for the alleviation of secondary diseases of cerebral infarction, intracerebral bleeding and the like.

In addition, the compounds (II) and (III) of the present invention and salts thereof are useful as advantageous intermediates for use in the production of the compound (I) of the present invention and its pharmaceutically acceptable salts. Reaction passway for the production of the compound (I) or its pharmaceutically acceptable salt from the compound (II), (III) or a salt thereof is as described in the foregoing.

Usefulness of the compounds of the present invention was confirmed by the following tests.

(1) $V_1$ receptor binding assay

A rat liver membrane sample was prepared in accordance with the method of Nakamura et al. (*J. Biol. Chem.*, 258, 9283 (1983)), and [$^3$H]-Arg-vasopressin (2 nM, specific activity=75.8 Ci/mmol), 70 μg of the membrane sample and each drug to be tested ($10^{-8}$ to $10^{-4}$M) were incubated at 30° C. for 30 minutes in 250 μl of 100 mM Tris-HCl buffer (pH=8.0) containing 5 mM of magnesium chloride, 1 mM of ethylenediaminetetraacetic acid (EDTA) and 0.1% of bovine serum albumin (BSA). Thereafter, the incubation solution was sucked off using a cell harvester and free ligand and excess buffer were removed by passing the reaction mixture through a glass filter (GF/B), thereby trapping receptor-bound labeled ligand on the glass filter. The glass filter was taken out, thoroughly dried and then mixed with a liquid scintillation cocktail, and the amount of the membrane-bound [$^3$H]-vasopressin was measured using a liquid scintillation counter to calculate the inhibition ratio by the following formula.

$$\text{Inhibition ratio (\%)} = 100 - \frac{C_1 - B_1}{C_0 - B_1} \times 100$$

$C_1$: amount of [$^3$H]-vasopressin bound to the membrane in the coexistence of known amount of each drug to be tested and [$^3$H]-vasopressin $C_0$: amount of [$^3$H]-vasopressin bound to the membrane when the drug to be tested was not added $B_1$: amount of [$^3$H]-vasopressin bound to the membrane in the presence of excess vasopressin ($10^{-6}$M)

Concentration of the drug to be tested which gives 50% inhibition ratio by the above calculation was defined as $IC_{50}$ and used in the following formula to calculate binding affinity of non-radioactive ligand, namely dissociation constant (Ki).

$$Ki = \frac{IC_{50}}{1 + [L]/KD}$$

[L]: concentration of radioactive ligand
KD: dissociation constant calculated from Scatchard plot Negative logarithm of the thus calculated Ki value was used as pKi value. The results are shown in Table 1.

(2) $V_2$ receptor binding assay

A rabbit renal medulla membrane sample was prepared in accordance with the method of Campbell et al. (*J. Biol. Chem.*, 247, 6167 (1972)), and [$^3$H]-Arg-vasopressin (2 nM, specific activity =75.8 Ci/mmol), 100 μg of the membrane sample and each drug to be tested ($10^{-8}$ to $10^{-4}$M) were subjected to the assay in the same manner as the case of the aforementioned $V_1$ receptor binding assay and the pKi values were calculated in the same manner. The results are shown in Table 1.

Compounds of the present invention are possessed of excellent arginine vasopressin antagonism. For example, the compounds of Examples 11, 12, 13, 15, 24, 28 and 85 showed excellent antagonisms on both $V_1$ and $V_2$ receptors, which were markedly strong even in comparison with a $V_2$ receptor antagonist compound OPC-31260 and a $V_1$ receptor antagonist compound OPC-21268 which are under development as arginine vasopressin antagonists. It was confirmed also that the compounds of Examples 42, 103, 104, 105 and 113 show markedly stronger $V_1$ receptor antagonism than that of OPC-21268 and are excellent in $V_1$ selectivity (see Table 1).

TABLE 1

Antagonism on arginine vasopressin $V_1$ and $V_2$ receptors

| Example No. | Binding activity on arginine vasopressin $V_1$ receptor (pKi) | Binding activity on arginine vasopressin $V_2$ receptor (pKi) |
|---|---|---|
| 11 | 8.89 | 9.06 |
| 12 | 9.66 | 9.71 |
| 13 | 10.10 | 9.58 |
| 14 | 8.91 | 9.39 |
| 15 | 9.79 | 9.13 |
| 19 | 8.58 | 8.84 |
| 22 (a) | 8.02 | 8.36 |
| 24 | 10.50 | 9.26 |
| 28 | 10.08 | 9.37 |
| 42 | 8.94 | 6.33 |
| 80 | 9.44 | 8.50 |
| 81 | 9.14 | 8.64 |
| 82 | 8.58 | 8.13 |
| 83 | 9.63 | 8.47 |
| 84 | 9.99 | — |
| 85 | 10.02 | 9.97 |
| 96 | 8.70 | 8.13 |
| 103 | 8.70 | 6.35 |
| 104 | 9.01 | 6.68 |
| 105 | 9.47 | 6.81 |
| 106 | 8.95 | 8.24 |
| 109 | 8.40 | 8.06 |
| 110 | 9.40 | 7.75 |
| 111 | 9.25 | 7.79 |
| 113 | 9.58 | 7.50 |
| 121 | 9.53 | 8.59 |
| 122 | 9.45 | 8.94 |
| 123 | 9.70 | 9.16 |
| 125 | 9.55 | 8.08 |
| 126 | 9.54 | 8.22 |
| 127 | 8.76 | 8.19 |
| 129 | 9.32 | 8.24 |
| 131 | 9.15 | 7.99 |
| 133 | 9.44 | 8.28 |
| 134 | 9.50 | 8.94 |
| 135 | 9.71 | 8.11 |
| Comparative compound (1)* | 6.71 | 8.01 |
| Comparative compound (2)** | 7.85 | 4.29 |

* OPC-31260 (WO 9105549, compound of Example 408, hydrochloride)

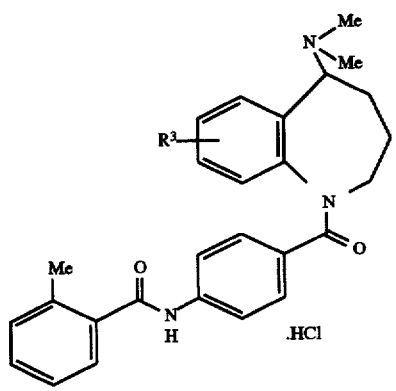

** OPC-21268 (EP 0382185, compound of Example 141)

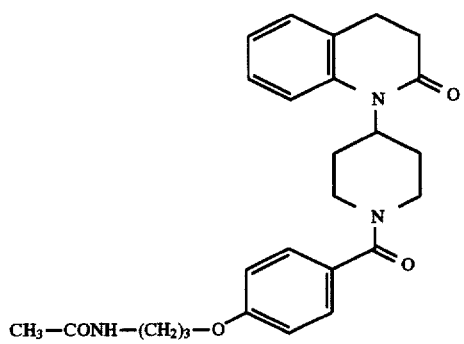

Water diuresis action in conscious rats (oral administration)

Each compound to be tested was suspended in 0.5% methylcellulose solution and orally administered in a dose of 3 mg/kg to male Wister rats (body weight, 270 to 300 g) which have been subjected to fasting with no water for 16 to 20 hours. Using a metabolic cage, urine samples were collected just after the administration of each test sample until 4 hours thereafter to measure the amount of urine.

In the test group in which each of the compounds of Examples 11, 13, 15, 24 and 84 was administered, the amount of urine collected during a period of from just after its administration to 2 hours later was 55 to 85 times larger than that in the solvent-administered group, and the amount of urine collected during a period of from 2 hours to 4 hours after its administration was 5 to 19 times larger than that in the solvent-administered group, thus showing prolonged water diuresis enhancing effect. On the other hand, in the OPC-31260-administered group, the amount of urine collected during a period of from just after its administration to 2 hours later was 11 times larger than that in the solvent-administered group, but the amount of urine collected during a period of from 2 hours to 4 hours after its administration was almost the same as that in the solvent-administered group, thus showing disappearance of the water diuresis enhancing effect.

On the basis of the above results, it was confirmed that the water diuresis enhancing effect of the compounds of the present invention by their oral administration into conscious rats is strong and long-acting in comparison with OPC-31260.

$V_1$ Antagonism in conscious rats (oral administration)

$V_1$ antagonism was examined using male Wister rats (body weight, 300 to 320 g) each of which has been subjected, 2 to 3 days before the test, to cannulation into left carotid for the measurement of blood pressure and into left jugular for the administration of arginine vasopressin (AVP). Blood pressure was measured under no anesthesia from the carotid cannula via a pressure transducer. Each compound to be tested was suspended in 0.5% methylcellulose solution and orally administered in a dose of 1 or 10 mg/kg.

Increase in the diastolic blood pressure caused by the intravenous administration of 30 mU/kg of AVP before the administration of a compound to be tested was defined as 100%, and increase in the blood pressure caused by the intravenous administration of 30 mU/kg of AVP was measured periodically during a period of from 30 minutes after the test compound administration to 8 hours thereafter to calculate inhibition ratio of pressure increment by the test compound, namely $V_1$ antagonism of the test compound.

Pressure increment by AVP was repressed to 50% or below during a period of from 30 minutes after the test sample administration to 6 hours thereafter by the administration of 1 mg/kg of each of the compounds of Examples 11, 13 and 24, thus showing prolonged $V_1$ antagonism. On the other hand, oral administration of OPC-21268 in a dose of 10 mg/kg which was ten times larger than the dose of the inventive compound was effective in repressing the pressure increment by AVP to a 50% or lower level only during a period of from 30 minutes to 1 hour after the administration, and the pressure increment by AVP returned to the 100% level 4 hours after the administration, thus showing disappearance of the $V_1$ antagonism.

On the basis of the above results, it was confirmed that the $V_1$ antagonism of the compounds of the present invention by their oral administration into conscious rats is strong and long-acting in comparison with OPC-21268.

A pharmaceutical composition which contains as its active ingredient one or a plurality of the compounds of the general formula (I) and pharmaceutically acceptable salts thereof is made into various dosage forms such as tablets, powders, fine granules, granules, capsules, pills, solutions, injections, suppositories, ointments, plasters and the like, making use of conventionally used pharmaceutical carriers, excipients and other additives, and administered orally or parenterally.

Clinical dose of the compound of the present invention for human may be optionally decided taking symptoms, weight, age, sex and the like of each patient into consideration, but it may generally be in the range of from 0.1 to 500 mg per adult per day in the case of oral administration, and the daily dose may be used in one portion or divided portions. Since the dose varies under various conditions, sufficient effects may be obtained in some cases with smaller dose than the above range.

As solid compositions for oral administration according to the present invention, tablets, powders, granules and the like may be used. In such solid compositions, one or a plurality of active ingredients may be mixed with at least one inert diluent such as lactose, mannitol, glucose, hydroxypropylcellulose, fine crystalline cellulose, starch, polyvinyl pyrrolidone or magnesium aluminate metasilicate. In accordance with the conventional way, the composition may contain other additives than the inert diluent, which include a lubricant such as magnesium stearate, a disintegrating agent such as fibrin calcium glycolate, a stabilizing agent such as lactose and a solubilizing agent or a solubilization aid such as glutamic acid or aspartic acid. As occasion demands, tablets or pills may be coated with a film of gastric or enteric substance such as sucrose, gelatin, hydroxypropylcellulose, hydroxypropylmethylcellulose phthalate or the like.

Liquid compositions for use in oral administration include pharmaceutically acceptable emulsions, solutions, suspensions, syrups, elixirs and the like which contain commonly used inert diluents such as purified water and ethyl alcohol. In addition to the inert diluents, such compositions may also contain auxiliary agents such as a solubilizing agent or a solubilization aid, a moistening agent, a suspending agent and the like, as well as a sweetening agent, a flavoring agent, an aromatic agent and an antiseptic agent.

Injections for use in parenteral administration include aseptic aqueous or non-aqueous solutions, suspensions and emulsions. Examples of diluent for use in aqueous solutions and suspensions include distilled water for injection use and physiological saline. Examples of diluent for use in non-aqueous solutions and suspensions include propylene glycol, polyethylene glycol, plant oils (e.g., olive oil), alcohols (e.g., ethyl alcohol) and Polysorbate 80 (trade name). Such compositions may also contain additives such as a tonicity agent, an antiseptic agent, a moistening agent, an emulsifying agent, a dispersing agent, a stabilizing agent (e.g., lactose) and solubilization aid, a solubilizing agent and the like.

infrared absorption spectrum, nuclear magnetic resonance spectrum and mass spectrometry data, respectively.

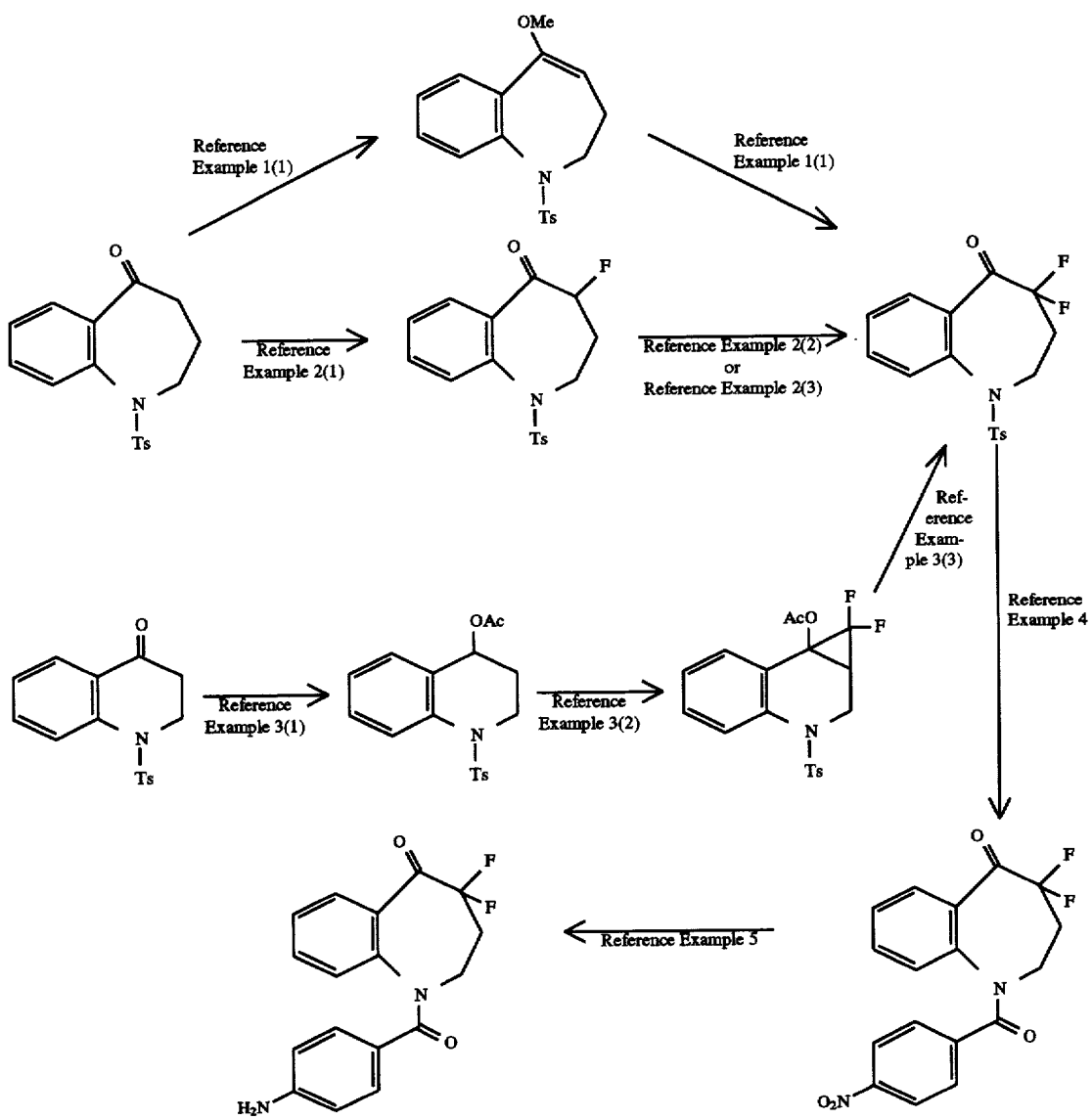

These compositions are sterilized by bacterial filtration through a bacteria-retaining filter, bactericide blending or irradiation. Alternatively, an aseptically produced solid composition may be used by dissolving it in sterile water or a sterile solvent for injection use prior to its use.

BEST MODE OF CARRYING OUT THE INVENTION

Thus, the compounds of the present invention and their production processes have been described which will be further illustrated in detail with reference to the following examples. The present invention, however, is not limited by these examples. In this connection, examples of the production methods of the intermediates of the present invention and other starting compounds to be used herein are shown as Reference Examples.

In the following examples, IR, $^1$H-NMR and MS mean

[In the above formulae, Ts means p-toluenesulfonyl group (tosyl group), Me means methyl group and Ac means acetyl group.]

(Reference Example 1)
(Fluorination method A-1)

(1) In 10 ml of dimethylformamide was suspended 165 mg of 60% sodium hydride, and 1.0 g of 1-tosyl-2,3,4,5-tetrahydro-1-H-1-benzazepin-5-one was added to the suspension under ice-cooling, followed by 1 hour of stirring in the ice bath. To this was added dropwise 0.90 ml of dimethyl sulfate, and the mixture was stirred for 30 minutes. After adding ammonium chloride aqueous solution to the reaction solution and subsequently evaporating the solvent, the thus obtained residue was treated with chloroform and water to effect phase separation, and the resulting organic layer was dried over anhydrous magnesium sulfate. The solvent was evaporated and the resulting residue was applied to column chromatography, which was eluted with hexane-ethyl acetate (4:1, v/v) to obtain 621 mg of 5-methoxy-1-tosyl-2,3-dihydro-1H-1-benzazepine.

$^1$H-NMR (δppm in CDCl$_3$, TMS internal standard): 2.09 (2H, m), 2.38 (3H, s), 3.21 (3H, s), 4.02 (2H, m), 4.60 (1H, t), 7.20–7.60 (total 8H) MS m/z (EI): 329 (M$^+$).

(2) In 6 ml of dichloroethane were suspended 213 mg of 5-methoxy-1-tosyl-2,3-dihydro-1H-1-benzazepine and 480 mg of N-fluoropyridinium trifluoromethanesulfonate, and the suspension was heated overnight under reflux. Water was added to separate the organic layer which was subsequently washed with saturated sodium bicarbonate aqueous solution and dried over anhydrous magnesium sulfate. The solvent was evaporated and the resulting residue was applied to column chromatography, which was eluted with hexane-ethyl acetate (4:1, v/v) to obtain 621 mg of 4,4-difluoro-1-tosyl-2,3,4,5-tetrahydro-1H-1-benzazepin-5-one.

(Reference Example 2)
(Fluorination method A-2)

(1) In 150 ml of tetrahydrofuran was dissolved 3.55 ml of diisopropylamine, and 14.9 ml of n-butyllithium was added dropwise while stirring at −78° C. in an atmosphere of argon. After 30 minutes of stirring under ice-cooling, the reaction mixture was cooled to −78° C., 60 ml of tetrahydrofuran solution containing 6.39 g of 1-tosyl-2,3,4,5-tetrahydro-1H-1-benzazepin-5-one was added dropwise thereto and the resulting mixture was stirred for 30 minutes. Then, 90 ml of tetrahydrofuran solution containing 8.94 g of N-fluorobenzenesulfonimide was added dropwise, and the mixture was stirred for 1 hour while gradually increasing the temperature to 0° C. After adding saturated ammonium chloride aqueous solution to the reaction solution, the mixture was concentrated under a reduced pressure. Ethyl acetate was added thereto to separate the water layer, and the organic layer was washed with saturated sodium thiosulfate aqueous solution, saturated sodium bicarbonate aqueous solution and saturated sodium chloride aqueous solution in that order. The organic layer was then dried over anhydrous magnesium sulfate and concentrated under a reduced pressure. The resulting residue was applied to silica gel column chromatography, which was eluted with chloroform to obtain 5.31 g of 4-fluoro-1-tosyl-2,3,4,5-tetrahydro-1H-1-benzazepin-5-one.

Elemental analysis data (C$_{17}$H$_{16}$NO$_3$SF)

|  | C % | H % | N % | S % | F % |
|---|---|---|---|---|---|
| calcd. | 61.25 | 4.84 | 4.20 | 9.62 | 5.70 |
| found | 61.07 | 4.80 | 4.16 | 10.01 | 5.87 |

IR (KBr, cm$^{-1}$): 1706 $^1$H-NMR (δppm in CDCl$_3$, TMS internal standard): 2.13 (1H, m), 2.44 (3H, s), 2.69 (1H, m), 3.64 (1H, m), 4.30 (1H, m), 5.06 (1H, ddd), 7.30 (2H, d), 7.36 (1H, m), 7.53 (1H, m), 7.56 (1H, m), 7.73 (2H, d), 7.82 (1H, m) MS (EI): 333 (M$^+$).

(2) To 300 ml of tetrahydrofuran solution containing 2.62 g of diisopropylamine and 2.91 g of potassium t-butoxide was added dropwise 16.2 ml of 1.6N n-hexane solution of n-butyllithilum at −78° C., followed by 30 minutes of stirring at −78° C. To this reaction solution was added 70 ml of tetrahydrofuran solution containing 7.2 g of 4-fluoro-1-tosyl-2,3,4,5-tetrahydro-1H-1-benzazepin-5-one, followed by 1 hour of stirring at −78° C. The reaction solution was mixed with 70 ml of tetrahydrofuran solution containing 10.22 g of N-fluorobenzenesulfonimide, and the mixture was stirred for 2 hours at −78° C. and then for 1 hour at room temperature. The reaction solution was mixed with 500 ml of 0.1N hydrochloric acid aqueous solution and the mixture was extracted with ethyl acetate. The resulting organic layer was washed with 10% sodium thiosulfate, 1N sodium hydroxide and saturated sodium chloride aqueous solution in that order and dried over anhydrous magnesium sulfate, subsequently evaporating the solvent. The resulting residue was applied to silica gel column chromatography, which was eluted with a mixed solvent of n-hexane and ethyl acetate (4:1, v/v) to obtain 2.31 g of 4,4-difluoro-1-tosyl-2,3,4,5-tetrahydro-1H-1-benzazepin-5-one.

(Fluorination method A-2, alternative)

(3) Trimethylsilyltrifluoromethane sulfonate (5.22 ml) was added dropwise to methylene chloride solution containing 1.80 g of 4-fluoro-1-tosyl-2,3,4,5-tetrahydro-1H-1-benzazepin-5-one and 4.52 ml of triethylamine under ice-cooling, and the mixture was stirred for 1 hour at room temperature. The reaction solution was diluted with ether and washed with saturated sodium bicarbonate aqueous solution, ice-cooled 1N hydrochloric acid aqueous solution, saturated sodium bicarbonate aqueous solution and saturated sodium chloride aqueous solution in that order. After drying on anhydrous magnesium sulfate, the solvent was evaporated under a reduced pressure to obtain a silyl enol ether derivative. The silyl enol ether and 2.67 g of N-fluoropyridinium trifluoromethanesulfonate were dissolved in 20 ml of dichloroethane and heated for 2 hours under reflux. Chloroform was added to the reaction solution, and the mixture was washed with saturated sodium chloride aqueous solution and then dried over anhydrous magnesium sulfate, subsequently evaporating the solvent under a reduced pressure. The resulting residue was applied to silica gel column chromatography, which was eluted with a mixed solvent of ethyl acetate and hexane (3:7, v/v) to obtain 1.78 g of 4,4-difluoro-1-tosyl-2,3,4,5-tetrahydro-1H-1-benzazepin-5-one.

IR (KBr, cm$^{-1}$): 1724 $^1$H-NMR (δppm in CDCl$_3$, TMS internal standard): 2.41 (2H, m), 2.43 (3H, s), 4.09 (2H, m), 7.25 (2H, d), 7.40 (1H, m), 7.48 (2H, d), 7.55 (3H, m) MS 351 (M$^+$).

(Reference Example 3)
(Fluorination method B)

(1) 1,2,3,4-Tetrahydroquinolin-4-one (2.00 g) and 114 mg of p-toluenesulfonic acid were dissolved in 30 ml of acetic acid isopropenyl ether, and the solution was heated under reflux for 2 days simultaneously evaporating acetic acid. Then, saturated sodium bicarbonate aqueous solution was added and the mixture was extracted with ethyl acetate, followed by drying on anhydrous magnesium sulfate. After evaporating the solvent, the resulting residue was crystallized from chloroform-diethyl ether-hexane to obtain 518 mg of 4-acetoxy-1-tosyl-1,2-dihydroquinoline.

$^1$H-NMR (δppm in CDCl$_3$, TMS internal standard): 2.16 (3H, s), 2.35 (3H, s), 4.60 (2H, d), 5.43 (1H, t), 7.05 (1H, d), 7.11 (2H, d), 7.19 (1H, t), 7.32 (1H, t), 7.39 (2H, d), 7.74 (1H, d) MS m/z (EI): 343 (M$^+$).

(2) 4-Acetoxy-1-tosyl-1,2-dihydroquinoline (518 mg) was dissolved in 5 ml of diglyme and heated under reflux, subsequently adding dropwise a diglyme solution containing 2.62 g of sodium chlorodifluoroacetate. After cooling, ethyl acetate was added, and the mixture was washed with water and then dried over anhydrous magnesium sulfate. The solvent was evaporated and the resulting residue was applied to column chromatography, which was eluted with hexane-ethyl acetate (4:1, v/v) to obtain 225 mg of 7b-acetoxy-1,1-difluoro-3-tosylcyclopropa[c]-1,2,3,4-tetrahydroquinoline.

$^1$H-NMR (δppm in CDCl$_3$, TMS internal standard): 1.99 (3H, s), 2.10 (1H, m), 2.41 (3H, s), 4.04 (1H, dd), 4.25 (1H, dd), 7.21 (1H, d), 7.28 (2H, d), 7.33 (1H, t), 7.55 (1H, d), 7.60 (1H, d), 7.62 (2H, d) MS m/z (EI): 393 (M$^+$).

(3) 7b-Acetoxy-1,1-difluoro-3-tosylcyclopropa[c]-1,2,3,4-tetrahydroquinoline (40 mg) was dissolved in 2 ml of methanol and 2 ml of tetrahydrofuran, 1 ml of aqueous solution containing 7 mg of lithium hydroxide was added dropwise to the thus prepared solution, and the resulting mixture was stirred for 2 days at room temperature. After evaporation of the solvent, water was added and the mixture was extracted with ethyl acetate. Then, the resulting organic layer was washed with water and dried over anhydrous magnesium sulfate. Thereafter, the solvent was evaporated, and the resulting residue was applied to column chromatography, which was eluted with hexane-ethyl acetate (4:1, v/v) to obtain 27 mg of 1-tosyl-4,4-difluoro-2,3,4,5-tetrahydro-1H-1-benzazepin-5-one.

(Reference Example 4)

4,4-Difluoro-1-tosyl-2,3,4,5-tetrahydro-1H-1-benzazepin-5-one (3.00 g) was dissolved in 14 ml of acetic acid, 7 ml of concentrated sulfuric acid was added to the solution and then the resulting mixture was heated at 60° C. for 10 hours. The reaction solution was ice-cooled, adjusted to a basic range with potassium hydroxide and extracted three times with ethyl acetate, and the resulting organic layer was dried over anhydrous potassium carbonate. By evaporating the reaction solvent, 4,4-difluoro-2,3,4,5-tetrahydro-1H-1-benzazepin-5-one was obtained. This product was used in the following reaction without purification.

To 20 ml of a methylene chloride solution containing the just obtained ketone and 1.55 ml of triethylamine was added 1.9 g of 4-nitrobenzoyl chloride under ice-cooling, followed by 12 hours of stirring at room temperature. The reaction solution was diluted with ethyl acetate and washed with 1N hydrochloric acid aqueous solution, 1N sodium hydroxide aqueous solution and saturated sodium chloride aqueous solution in that order. The organic layer was dried over anhydrous magnesium sulfate, the solvent was evaporated under a reduced pressure and then the resulting residue was recrystallized using chloroform-ether to obtain 1.65 g of 4,4-difluoro-1-(4-nitrobenzoyl)-2,3,4,5-tetrahydro-1H-1-benzazepin-5-one. The mother liquor was evaporated under a reduced pressure, and the resulting residue was applied to silica gel column chromatography, which was eluted with chloroform to obtain additional 649 mg of 4,4-difluoro-1-(4-nitrobenzoyl)-2,3,4,5-tetrahydro-1H-1-benzazepin-5-one.

Melting point: 192°–195° C.
Elemental analysis data ($C_{17}H_{12}N_2O_4F_2$)

|  | C (%) | H (%) | N (%) | F (%) |
|---|---|---|---|---|
| calcd. | 58.96 | 3.49 | 8.09 | 10.97 |
| found | 59.00 | 3.62 | 7.93 | 10.91 |

IR (KBr, cm$^{-1}$): 1716, 1656 $^1$H-NMR (δppm in CDCl$_3$, TMS internal standard): 2.73 (2H, m), 4.35 (2H, m), 6.62 (1H, m), 7.25 (1H, m), 7.33 (1H, m), 7.48 (2H, m), 8.00 (1H, m), 8.10 (2H, m) MS (EI): 346 (M$^+$).

(Reference Example 5)

4,4-Difluoro-1-(4-nitrobenzoyl)-2,3,4,5-tetrahydro-1H-1-benzazepin-5-one (940 mg) was dissolved in 20 ml of acetic acid, 3.07 g of stannous chloride was added to the solution at room temperature and then the resulting mixture was heated under reflux for 5 hours. The reaction solution was ice-cooled and adjusted to a basic range with 1N sodium hydroxide. Then, after separating the organic layer, the water layer was extracted with ethyl acetate. The resulting organic layer was dried over anhydrous potassium carbonate and the solvent was evaporated under a reduced pressure. The thus prepared residue was recrystallized from chloroformhexane to obtain 711 mg of 1-(4-aminobenzoyl)-4,4-difluoro-2,3,4,5-tetrahydro-1H-1-benzazepin-5-one.

IR (KBr, cm$^{-1}$): 1712, 1628 $^1$H-NMR (δppm in CDCl$_3$, TMS internal standard): 1.59 (2H, m), 2.66 (2H, m), 3.88 (1H, m), 4.24 (1H, m), 6.45 (2H, m), 6.76 (1H, m), 7.17 (2H, d), 7.24 (2H, m), 7.95 (1H, m) MS (EI): 316 (M$^+$).

(Reference Example 6)

60% Sodium hydride (228 mg) was suspended in 10 ml of tetrahydrofuran, 0.984 ml of trimethyl phosphonoacetate was added dropwise to the suspension under ice-cooling, and the resulting mixture was stirred at room temperature for 30 minutes. At −78° C., 20 ml of a tetrahydrofuran solution containing 600 mg of 1-(4-aminobenzoyl)-4,4-difluoro-2,3,4,5-tetrahydro-1H-1-benzazepin-5-one was added dropwise, subsequently increasing the temperature to 0° C. spending 10 hours. Saturated ammonium chloride aqueous solution and water were added and the mixture was extracted with chloroform. The organic layer was dried over anhydrous magnesium sulfate, the solvent was evaporated under a reduced pressure and then the resulting residue was applied to silica gel column chromatography, which was eluted with a mixed solvent of ethyl acetate and hexane (4.5:5.5, v/v) to initially obtain 170 mg of methyl (E)-[1-(4-aminobenzoyl)-4,4-difluoro-2,3,4,5-tetrahydro-1H-1-benzazepin-5-ylidene]acetate.

$^1$H-NMR (δppm in CDCl$_3$, TMS internal standard): 2.40 (2H, m), 3.18 (1H, m), 3.71 (3H, s), 3.78 (2H, m), 5.08 (1H, m), 6.42 (2H, d), 6.59 (1H, s), 6.73 (1H, d), 7.14 (1H, m), 7.20 (1H, m), 7.29 (3H, m) MS (EI): 372 (M$^+$).

By further continuing the elution, 536 mg of methyl (Z)-[1-(4-aminobenzoyl)-4,4-difluoro-2,3,4,5-tetrahydro-1H-1-benzazepin-5-ylidene]acetate was obtained.

$^1$H-NMR (δppm in CDCl$_3$, TMS internal standard): 2.50 (2H, m), 3.20 (1H, m), 3.78 (2H, m), 3.82 (3H, s), 5.05 (1H, m), 6.18 (1H, s), 6.39 (2H, d), 6.73 (1H, d), 6.97 (2H, d), 7.12 (1H, m), 7.23 (1H, m), 7.37 (1H, m) MS (EI): 372 (M$^+$).

(Reference Example 7)

Triethyl phosphonoacetate (4.12 g) was added to 734 mg of 60% sodium hydride suspended in 70 ml of tetrahydrofuran under ice-cooling, and the mixture was stirred for 30 minutes under ice-cooling. To the reaction solution was added 1.16 g of 1-(4-aminobenzoyl)-4,4-difluoro-2,3,4,5-tetrahydro-1H-1-benzazepin-5-one, followed by 3 hours of stirring at room temperature. The reaction solution was poured into ice water and extracted with ethyl acetate. The organic layer was washed with saturated sodium chloride aqueous solution and dried over anhydrous magnesium sulfate, and then the solvent was evaporated to obtain 1.41 g of a mixture of ethyl (E) and (Z)-[1-(4-aminobenzoyl)-4,4-difluoro-2,3,4,5-tetrahydro-1H-1-benzazepin-5-ylidene]acetate.

MS (FAB): 387 (M++1).

(Reference Example 8)

o-Phenylbenzoic acid (163 mg) was dissolved in 5 ml of methylene chloride, a catalytically effective amount of N,N-dimethylformamide was added dropwise, and 0.165 ml of oxalyl chloride was added dropwise. After 3 hours of stirring at room temperature, benzene was added and the solvent was evaporated to obtain o-phenylbenzoic acid chloride.

1-(4-Aminobenzoyl)-4,4-difluoro-2,3,4,5-tetrahydro-1H-1-benzazepin-5-one (200 mg) and 5 ml of pyridine were dissolved in 10 ml of methylene chloride, and 10 ml of a methylene chloride solution containing the o-phenylbenzoic acid chloride obtained above was added dropwise under ice-cooling. After 1 hour of stirring at room temperature, the solvent was evaporated under a reduced pressure, and the thus obtained residue was dissolved in ethyl acetate and washed with saturated sodium carbonate aqueous solution, 1N hydrochloric acid aqueous solution and saturated sodium chloride aqueous solution in that order. After drying on anhydrous magnesium sulfate and subsequent evaporation of the solvent under a reduced pressure, the resulting residue was applied to column chromatography, which was eluted with a mixed solvent of ethyl acetate and hexane (2:3, v/v) to obtain 283 mg of 4,4-difluoro-1-[4-(2-phenylbenzoylamino)benzoyl]-2,3,4,5-tetrahydro-1H-1-benzazepin-5-one. This product was recrystallized from ethyl acetate-hexane.

Melting point: 201°–203° C. $^1$H-NMR (δppm in CDCl$_3$, TMS internal standard): 2.67 (2H, m), 3.30 (1H, m), 4.21 (1H, m), 6.65 (2H, m), 6.88 (1H, s), 6.97 (2H, m), 7.19 (2H, m), 7.24 (1H, m), 7.32–7.47 (total 7H), 7.55 (1H, m), 7.88 (1H, m), 7.96 (1H, m) MS (EI): 496 (M$^+$).

(Reference Example 9)

Using 2-(4-methylphenyl)benzoic acid and (Z)-1-(4-aminobenzoyl)-4,4-difluoro-2,3,4,5-tetrahydro-1H-1-benzazepin-5-one, a similar procedure as in Reference Example 8 was repeated to obtain 4,4-difluoro-1-[4-[2-(4methylphenyl)benzoylamino]benzoyl]-2,3,4,5-tetrahydro-1H-1-benzazepin-5-one.

$^1$H-NMR (δppm in CDCl$_3$, TMS internal standard): 2.35 (3H, s), 2.67 (2H, m), 3.50–4.80 (total 2H), 6.66 (1H, m), 6.94 (1H, s), 6.99 (2H, m), 7.18–7.32 (total 8H), 7.40 (1H, d), 7.46 (1H, m), 7.53 (1H, m), 7.86 (1H, m), 7.95 (1H, m) MS (EI): 511 (M$^+$+1).

(Example 1)

Using 396 mg of o-phenylbenzoic acid, 0.290 ml of oxalyl chloride and 620 mg of methyl (Z)-[1-(4-aminobenzoyl)4,4-difluoro-2,3,4,5-tetrahydro-1H-1-benzazepin-5ylidene]acetate, a similar procedure as in Reference Example 8 was repeated to obtain 878 mg of methyl (Z)-[4,4-difluoro-1-[4-(2-phenylbenzoylamino)benzoyl]-2, 3,4,5-tetrahydro-1H-1-benzazepin-5-ylidene]acetate.

$^1$H-NMR (δppm in CDCl$_3$, TMS internal standard): 2.30–2.80 (total 2H), 3.21 (1H, m), 3.83 (3H, s), 5.03 (1H, m), 6.17 (1H, s), 6.66 (1H, m), 6.91 (3H, m), 7.01 (2H, m), 7.09 (1H, t), 7.24 (1H, t), 7.33–7.45 (total 7H), 7.52 (1H, t), 7.56 (1H, t), 7.83 (1H, d) MS (EI): 552 (M$^+$).

(Example 2)

Using 127 mg of o-phenylbenzoic acid, 0.141 ml of oxalyl chloride and 200 mg of methyl (E)-[1-(4-aminobenzoyl)-4,4-difluoro-2,3,4,5-tetrahydro-1H-1-benzazepin-5ylidene]acetate, a similar procedure as in Reference Example 8 was repeated to obtain 287 mg of methyl (E)-[4,4-difluoro-1-[4-(2-phenylbenzoylamino)benzoyl]-2, 3,4,5-tetrahydro-1H-1-benzazepin-5-ylidene]acetate.

$^1$H-NMR (δppm in CDCl$_3$, TMS internal standard): 2.20–2.70 (total 2H), 3.30 (1H, m), 3.67 (3H, s), 4.98 (1H, m), 6.55–6.74 (total 2H), 6.85–7.70 (total 15H), 7.84 (1H, m) MS (EI): 553 (M$^+$+1).

(Example 3)

Using 630 mg of 2-(4-methylphenyl)benzoic acid, 0.389 ml of oxalyl chloride and 670 mg of methyl (Z)-[1-(4-aminobenzoyl)-4,4-difluoro-2,3,4,5-tetrahydro-1H-1-benzazepin-5-ylidene]acetate, a similar procedure as in Reference Example 8 was repeated to obtain 556 mg of methyl (Z)-[4,4-difluoro-1-[4-[2-(4methylphenyl)benzoylamino] benzoyl]-2,3,4,5-tetrahydro-1H-1-benzazepin-5-ylidene]acetate.

$^1$H-NMR (δppm in CDCl$_3$, TMS internal standard): 2.36 (3H, s), 2.40 (1H, m), 2.62 (1H, m), 3.21 (1H, m), 3.83 (3H, s), 5.04 (1H, m), 6.17 (1H, s), 6.67 (1H, d), 6.90 (1H, s), 6.94 (2H, d), 7.02 (2H, d), 7.10 (1H, t), 7.18 (2H, d), 7.22 (1H, t), 7.29 (2H, d), 7.37 (2H, m), 7.44 (1H, m), 7.52 (1H, m), 7.82 (1H, d) MS (EI): 566 (M$^+$+1).

(Example 4)

Using 277 mg of 2-(3-methylphenyl)benzoic acid, 0.127 ml of oxalyl chloride and 180 mg of methyl (Z)-[1-(4-aminobenzoyl)-4,4-difluoro-2,3,4,5-tetrahydro-1H-1-benzazepin-5-ylidene]acetate, a similar procedure as in Reference Example 8 was repeated to obtain 249 mg of methyl (Z)-[4,4-difluoro-1-[4-[2-(3methylphenyl)benzoylamino] benzoyl]-2,3,4,5-tetrahydro-1H-1-benzazepin-5-ylidene] acetate.

$^1$H-NMR (δppm in CDCl$_3$, TMS internal standard): 2.29 (3H, s), 2.41 (1H, m), 2.65 (1H, m), 3.21 (1H, m), 3.83 (3H, s), 5.03 (1H, m), 6.18 (1H, s), 6.66 (1H, m), 6.85–7.60 (total 15H), 7.85 (1H, d) MS (EI): 566 (M$^+$).

(Example 5)

Using 230 mg of 4,4-difluoro-1-[4-(2phenylbenzoylamino)benzoyl]-2,3,4,5-tetrahydro-1H-1-benzazepin-5-one, a similar procedure as in Reference Example 6 was repeated to obtain 100 mg of methyl (Z)-[4,4-difluoro- 1-[4-(2-phenylbenzoylamino)benzoyl]-2, 3,4,5-tetrahydro-1-H-1-benzazepin-5-ylidene]acetate.

(Example 6)

2-(4-Methylphenyl)benzoic acid (917 mg) was dissolved in 15 ml of methylene chloride containing one drop of dimethylformamide. Then, 4.86 ml of oxalyl chloride was added under ice-cooling, and the mixture was stirred at room temperature for 3 hours. To the reaction solution was added dropwise a mixture solution of 10 ml pyridine and 10 ml methylene chloride containing 1.4 g of ethyl (E)- and (Z)-[1-(4-aminobenzoyl)-4,4-difluoro-2,3,4,5-tetrahydro-1H-1-benzazepin-5-ylidene]acetate mixture, followed by 13 hours of stirring at room temperature. Water was added to the reaction solution and the mixture was extracted with ethyl acetate. The resulting organic layer was washed with 1N hydrochloric acid aqueous solution, 1N sodium hydroxide aqueous solution and saturated sodium chloride aqueous solution in that order and dried over anhydrous magnesium sulfate, and then the solvent was evaporated. The resulting residue was purified by applying it to silica gel column chromatography and eluting with a mixed solvent of n-hexane and ethyl acetate (2:1, v/v) to obtain 260 mg and 290 mg of ethyl (Z)- and (E)-[4,4-difluoro-1-[4-[2-(4methyl)phenyl]benzoylamino]benzoyl-2,3,4,5-tetrahydro-1H-1-benzazepin-5-ylidene]acetate.

Compound 6 (a)

(z) form $^1$H-NMR (δppm in CDCl$_3$, TMS internal standard): 1.34 (3H, t), 2.39 (3H, s), 2.40 (2H, m), 3.10–3.30 (1H, m), 4.29 (2H, q), 4.90–5.10 (1H, m), 6.17 (1H, s), 6.66 (1H, d), 6.80–7.60 (total 14H), 7.82 (1H, d) MS (FAB): 581 (M$^+$+1).

Compound 6 (b)

(E) form $^1$H-NMR (δppm in CDCl$_3$, TMS internal standard): 1.23 (3H, t), 2.35 (3H, s), 2.40 (2H, m), 3.19 (1H, m), 4.13 (2H, m), 5.02 (1H, m), 6.59 (1H, s), 6.66 (1H, d), 6.80–7.60 (total 14H), 7.82 (1H, d) MS (FAB): 581 (M$^+$+1).

(Example 7)

Methyl (Z)-[4,4-difluoro-1-[4-(2phenylbenzoylamino) benzoyl]-2,3,4,5-tetrahydro-1H-1-benzazepin-5-ylidene]

acetate (857 mg) was dissolved in 10 ml of methanol, 2 ml of aqueous solution containing 195 mg of lithium hydroxide monohydrate was added dropwise to the above solution under ice-cooling, and the mixture was stirred at room temperature for 7 hours. After evaporating the solvent under a reduced pressure, 1N hydrochloric acid aqueous solution was added, and the mixture was extracted with chloroform and dried over anhydrous magnesium sulfate. After evaporation of the solvent under a reduced pressure, the resulting residue was recrystallized from ethyl acetatehexane to obtain 633 mg of (Z)-[4,4-difluoro-1-[4-(2-phenylbenzoylamino)benzoyl]-2,3,4,5-tetrahydro-1H-1-benzazepin-5-ylidene]acetic acid.

Melting point: 224°–226° C. $^1$H-NMR ($\delta$ppm in CDCl$_3$, TMS internal standard): 2.41 (1H, m), 2.67 (1H, m), 3.24 (1H, m), 3.68 (1H, m), 5.00 (1H, m), 6.19 (1H, s), 6.67 (1H, m), 6.92 (2H, m), 6.98 (3H, m), 7.10 (1H, m), 7.24 (1H, d), 7.30–7.50 (total 8H), 7.53 (1H, m), 7.80 (1H, m) Ms (EI): 538 (M$^+$).

(Example 8)

Using 280 mg of methyl (E)-[4,4-difluoro-1-[4-(2phenylbenzoylamino)benzoyl]-2,3,4,5-tetrahydro-1H-1-benzazepin-5-ylidene]acetate, a similar procedure as in Example 7 was repeated to obtain 187 mg of (E)-[4,4-difluoro 1-[4-(2-phenylbenzoylamino)benzoyl]-2,3,4,5-tetrahydro-1H-1-benzazepin-5-ylidene]acetic acid.

$^1$H-NMR ($\delta$ppm in CDCl$_3$, TMS internal standard): 2.41 (2H, m), 3.10–3.50 (total 2H), 4.99 (1H, m), 6.59 (1H, s), 6.67 (1H, m), 6.89 (2H, m), 7.08 (2H, m), 7.17 (1H, m), 7.24–7.48 (total 8H), 7.52 (1H, m), 7.73 (1H, m) MS (EI): 53S (M$^+$).

(Example 9)

Using 527 mg of methyl (Z)-[4,4-difluoro-1-[4-[2-(4methylphenyl)benzoylamino]benzoyl]-2,3,4,5-tetrahydro-1H-1-benzazepin-5-ylidene]acetate, a similar procedure as in Example 7 was repeated to obtain 460 mg of (Z)-[4,4-difluoro-1-[4-[2-(4-methylphenyl)benzoylamino]benzoyl]-2,3,4,5- tetrahydro-1H-1-benzazepin-5-ylidene]acetic acid.

$^1$H-NMR ($\delta$ppm in CDCl$_3$, TMS internal standard): 2.35 (3H, s), 2.50–3.80 (total 4H), 5.02 (1H, m), 6.20 (1H, s), 6.69 (1H, m), 6.90–7.48 (total 14H), 7.52 (1H, m), 7.80 (1H, d) MS (EI): 552 (M$^+$).

(Example 10)

Using 240 mg of methyl (Z)-[4,4-difluoro-1-[4-[2-(3methylphenyl)benzoylamino]benzoyl]-2,3,4,5-tetrahydro-1H-1-benzazepin-5-ylidene]acetate, a similar procedure as in Example 7 was repeated to obtain 210 mg of (Z)-[4,4-difluoro-1-[4-[2-(3-methylphenyl)phenylbenzoylamino]benzoyl]-2,3,4,5-tetrahydro-1H-1-benzazepin-5-ylidene]acetic acid.

$^1$H-NMR ($\delta$ppm in CDCl$_3$, TMS internal standard): 2.35 (3H, s), 2.35–2.80 (total 3H), 3.20 (1H, m), 5.02 (1H, m), 6.19 (1H, s), 6.69 (1H, m), 6.85–7.60 (total 15H), 7.81 (1H, m) MS (EI): 552 (M$^+$).

(Example 11)

(Z)-[4,4-Difluoro-1-[4-(2phenylbenzoylamino)benzoyl]-2,3,4,5-tetrahydro-1H-1-benzazepin-5-ylidene]acetic acid (318 mg) and 96 mg of 1-hydroxybenzotriazole were dissolved in a mixed solvent of 10 ml of methylene chloride and 10 ml of acetonitrile, and 10 ml of a methylene chloride solution containing 136 mg of 1-ethyl-3-(dimethylaminopropyl)carbodiimide hydrochloride was added dropwise under ice-cooling. Then, 0.079 ml of N-methylpiperazine was added and the mixture was stirred overnight at room temperature. Then, 1N sodium hydroxide aqueous solution was added, and the mixture was extracted with chloroform and dried over anhydrous potassium carbonate. The solvent was evaporated, and the resulting residue was applied to silica gel column chromatography, which was eluted with a mixed solvent of chloroform and methanol (95:5, v/v) to obtain 308 mg of free base. This product was dissolved in methanol and converted into hydrochloride by adding 4N hydrochloric acid ethyl acetate solution, and then the solvent was evaporated under a reduced pressure. By recrystallizing the thus obtained residue from methanoldiethyl ether, 185 mg of (Z)-4'-[[4,4-difluoro-5-(4-methyl-1-piperazinyl)carbonylmethylene-2,3,4,5-tetrahydro-1H-1-benzazepin-1-yl]carbonyl]-2-phenylbenzanilide hydrochloride was obtained.

Melting point: 194°–197° C. $^1$H-NMR ($\delta$ppm in DMSO-d$_6$, TMS internal standard): 2.42 (2H, m), 2.81 (3H, s), 2.82–3.28 (total 4H), 3.36–3.70 (total 3H), 4.09 (1H, m), 4.43 (1H, m), 4.86 (1H, m), 6.77 (1H, s), 6.82 (1H, m), 7.01 (2H, m), 7.20 (1H, t), 7.25–7.41 (total 8H), 7.47 (2H, m), 7.56 (3H, m), 10.35 (1H, m), 11.13 (1H, m) MS (EI): 621 (M$^+$+1).

(Example 12)

Using 94 mg of (Z)-[4,4-difluoro-1-[4-(2phenylbenzoylamino)benzoyl]-2,3,4,5-tetrahydro-1H-1-benzazepin-5-ylidene]acetic acid and 90 mg of piperazine, a similar procedure as in Example 11 was repeated to obtain 70 mg of (Z)-4'-[[4,4-difluoro-5-[(1piperazinylcarbonyl)methylene]-2,3,4,5-tetrahydro-1H-1-benzazepin-1-yl]carbonyl]-2-phenylbenzanilide hydrochloride in the form of colorless amorphous solid.

$^1$H-NMR ($\delta$ppm in DMSO-d$_6$, TMS internal standard): 2.42 (2H, m), 3.02–3.22 (total 5H), 3.60–3.92 (total 4H), 4.87 (1H, m), 6.77 (1H, s), 6.82 (1H, m), 7.01 (2H, m), 7.20 (1H, m), 7.25–7.41 (total 8H), 7.47 (2H, m), 7.51–7.62 (total 3H), 9.30 (1H, m), 10.34 (1H, s) MS (EI): 606 (M$^+$).

(Example 13)

Using 196 mg of (Z)-[4,4-difluoro-1-[4-(2phenylbenzoylamino)benzoyl]-2,3,4,5-tetrahydro-1H-1-benzazepin-5-ylidene]acetic acid and 56 mg of 4dimethylaminopiperidine, a similar synthesis method of Example 11 was repeated and the product was recrystallized from chloroform-ether to obtain 160 mg of (Z)-4'-[[4,4-difluoro-5-[[(4-dimethylaminopiperidino)carbonyl]methylene]- 2,3,4,5-tetrahydro-1H-1-benzazepin-1-yl]carbonyl]-2-phenylbenzanilide hydrochloride.

Melting point: decomposition at 230° C. or above $^1$H-NMR ($\delta$ppm in DMSO-d$_6$, TMS internal standard): 1.39–1.80 (total 2H), 2.07 (2H, m), 2.41 (2H, m), 2.66 (1H, m), 2.72 (6H, s), 2.95–3.20 (total 2H), 3.43 (1H, m), 4.04 (1H, m), 4.52 (1H, m), 4.86 (1H, m), 6.78 (1H, s), 6.81 (1H, m), 7.01 (2H, m), 7.19 (1H, m), 7.26–7.43 (total 8H), 7.44–7.60 (total 5H), 10.35 (1H, s), 10.41 (1H, m) MS (EI): 649 (M$^+$+1).

(Example 14)

Using 275 mg of (Z)-[4,4-difluoro-1-[4-(2-phenylbenzoylamino)benzoyl]-2,3,4,5-tetrahydro-1H-1-benzazepin-5-ylidene]acetic acid and 0.063 ml of 2-aminomethylpyridine, a similar procedure as in Example 11 was repeated to obtain 190 mg of (Z)-4'-[[4,4-difluoro- 5-[N-(2-pyridylmethyl)carbonylmethylene]-2,3,4,5-tetrahydro-1H-1-benzazepin-1-yl]carbonyl]-2-phenylbenzanilide hydrochloride in the form of colorless amorphous solid.

¹H-NMR (δppm in CDCl₃, TMS internal standard): 2.32 (1H, m), 2.73 (1H, m), 3.20 (1H, m), 4.89 (3H, m), 6.41 (1H, m), 6.59 (1H, m), 6.85–7.10 (total 6H), 7.23 (1H, m), 7.30–7.50 (total 7H), 7.53 (1H, m), 7.70 (1H, m), 7.80 (1H, m), 7.89 (1H, m), 8.23 (1H, m), 8.45 (1H, m), 8.58 (1H, m) MS (EI): 629 (M⁺+1).

(Example 15)

Using 250 mg of (Z)-[4,4-difluoro-1-[4-(2phenylbenzoylamino)benzoyl]-2,3,4,5-tetrahydro-1H-1-benzazepin-5-ylidene]acetic acid and 76 mg of N,N,N'-trimethylethylenediamine, a similar procedure as in Example 11 was repeated and then the product was recrystallized from ethanol-diisopropyl ether to obtain 190 mg of (Z)-4'-[4,4-difluoro-5-[[N-(2-dimethylaminoethyl)-N-methylcarbonylmethylene]-2,3,4,5-tetrahydro-1H-1-benzazepin-1-yl]carbonyl]-2-phenylbenzanilide hydrochloride.

Melting point: 157°–160° C ¹H-NMR (δppm in DMSO-d₆, TMS internal standard): 2.41 (2H, m), 2.80 (6H, m), 3.08 (3H, s), 3.25 (2H, m), 3.55–4.00 (total 3H), 4.86 (1H, m), 6.79 (2H, m), 7.00 (2H, m), 7.19 (1H, m), 7.24–7.41 (total 8H), 7.46 (3H, m), 7.54 (5H, m), 10.34 (1H, s), 10.64 (1H, m) MS (EI): 622 (M⁺).

(Example 16)

Using 160 mg of (E)-[4,4-difluoro-1-[4-(2-phenylbenzoylamino)benzoyl]-2,3,4,5-tetrahydro-1H-1-benzazepin-5-ylidene]acetic acid and 0.043 ml of Nmethylpiperazine, a similar procedure as in Example 11 was repeated to obtain 90 mg of (E)-4'-[[4,4-difluoro-5-(4-methyl-1-piperazinyl)carbonylmethylene-2,3,4,5-tetrahydro-1H-1-benzazepin-1-yl]carbonyl]-2-phenylbenzanilide hydrochloride in the form of colorless amorphous solid.

¹H-NMR (δppm in DMSO-d₆, TMS internal standard ): 2.23–2.45 (total 2H), 2.70–3.25 (total 7H), 3.35–3.80 (total 3H), 4.08 (1H, m), 4.36 (1H, m), 4.91 (1H, m), 6.72 (1H, m), 6.97–7.59 (total 17H), 10.36 (1H, m), 10.72 (1H, m) MS (EI): 620 (M⁺+1).

(Example 17)

Using 226 mg of (Z)-[4,4-difluoro-1-[4-[2-(4methylphenyl)benzoylamino]benzoyl]-2,3,4,5-tetrahydro-1H-1-benzazepin-5-ylidene]acetic acid and 0.054 ml of N-methylpiperazine, a similar procedure as in Example 11 was repeated to obtain 160 mg of (Z)-4'-[[4,4-difluoro-5-(4-methyl-1-piperazinyl)carbonylmethylene-2,3,4,5-tetrahydro-1H-1-benzazepin-1-yl]carbonyl]-2-(4-methylphenyl)benzanilide hydrochloride in the form of colorless amorphous solid.

¹H-NMR (δppm in DMSO-d₆, TMS internal standard): 2.28 (3H, s), 2.45 (2H, m), 2.82 (3H, m), 2.83–3.25 (total 4H), 3.36–3.65 (total 3H), 4.09 (1H, m), 4.45 (1H, m), 4.86 (1H, m), 6.77 (1H, s), 6.83 (1H, m), 7.02 (2H, m), 7.13 (2H, d), 7.20 (1H, t), 7.27 (2H, d), 7.32 (1H, t), 7.36–7.47 (4H, m), 7.48–7.59 (3H, m), 10.36 (1H, m), 10.90 (1H, m) MS (EI): 634 (M⁺).

(Example 18)

Using 203 mg of (Z)-[4,4-difluoro-1-[4-[2-(4methylphenyl)benzoylamino]benzoyl]-2,3,4,5-tetrahydro-1-H-1-benzazepin- 5-ylidene]acetic acid and 0.045 ml of 2-aminomethylpyridine, a similar procedure as in Example 11 was repeated to obtain 150 mg of (Z)-4'-[[4,4-difluoro-5-[N-(2pyridylmethyl)carbonylmethylene]-2,3,4,5-tetrahydro-1H-1-benzazepin-1-yl]carbonyl]-2-(3-methylphenyl)benzanilide hydrochloride in the form of colorless amorphous solid.

¹H-NMR (67 ppm in DMSO-d₆, TMS internal standard): 2.27 (3H, s), 2.38 (1H, m), 2.67 (1H, m), 3.07 (1H, m), 4.65 (2H, m), 4.87 (1H, m), 6.63 (1H, s), 6.77 (1H, m), 7.03 (2H, m), 7.10–7.20 (total 3H), 7.24–7.34 (total 3H), 7.35–7.59 (total 7H), 7.75 (2H, m), 8.30 (1H, m), 8.75 (1H, m), 9.17 (1H, m), 10.33 (1H, s) MS (EI): 642 (M⁺).

(Example 19)

Using 210 mg of (Z)-[4,4-difluoro-1-[4-[2-(3methylphenyl)benzoylamino]benzoyl]-2,3,4,5-tetrahydro-1H-1-benzazepin-5-ylidene]acetic acid and 0.055 ml of N-methylpiperazine, a similar procedure as in Example 11 was repeated to obtain 140 mg of (Z)-4'-[[4,4-difluoro-5-(4-methyl-1-piperazinyl)carbonylmethylene-2,3,4,5-tetrahydro-1H-1-benzazepin-1-yl]carbonyl]-2-(3-methylphenyl)benzanilide hydrochloride in the form of colorless amorphous solid.

¹H-NMR (δppm in DMSO-d₆, TMS internal standard): 2.21 (3H, s), 2.45 (2H, m), 2.83 (3H, s), 2.84–3.20 (total 4H), 3.38–3.69 (total 3H), 4.10 (1H, m), 4.44 (1H, m), 4.86 (1H, m), 6.77 (1H, s), 6.82 (1H, m), 7.01 (2H, m), 7.09 (1H, m), 7.19 (4H, m), 7.26–7.41 (3H, m), 7.45 (2H, m), 7.50–7.60 (3H, m), 10.34 (1H, m), 10.71 (1H, m) MS (EI): 634 (M⁺).

(Example 20)

Ethyl (Z)-[1-[4-[2-(4methylphenyl)benzoylamino]benzoyl]-4,4-difluoro-2,3,4,5-tetrahydro-1H-1-benzazepin-5-ylidene]acetate (200 mg) was dissolved in 5 ml of a mixed solvent of 40% methylamine and 60% methanol and the solution was stirred for 2 hours at 50° C. in a sealed tube. After evaporation of the solvent, the resulting residue was applied to silica gel column chromatography, which was eluted with a mixed solvent of chloroform and methanol (40:1, v/v) to obtain 150 mg of (Z)-4'-[[4,4-difluoro-5-(N-methylcarbamoylmethylene)-2,3,4,5- tetrahydro-1H-1-benzazepin-1-yl]carbonyl]-2-(4methylphenyl)benzanilide.

¹H-NMR (δppm in DMSO-d₆, TMS internal standard): 2.27 (3H, s), 2.35 (2H, m), 2.64 (3H, d), 3.00 (1H, m), 4.90 (1H, m), 6.48 (1H, s), 6.75 (1H, d), 7.03 (1H, d), 7.12 (2H, d), 7.20–7.60 (total 11H), 8.23 (1H, d), 10.30 (1H, s₂MS (FAB): 566 (M⁺+1).

(Example 21)

Using 200 mg of ethyl (E)-[1-[4-[2-(4methylphenyl)benzoylamino]benzoyl]-4,4-difluoro-2,3,4,5-tetrahydro-1H-1-benzazepin-5-ylidene]acetate as the starting material, a similar procedure as in Example 20 was repeated to obtain 180 mg of (E)-4'-[[4,4-difluoro-5-(N-methylcarbamoylmethyl)-2,3,4,5-tetrahydro-1H-1-benzazepin-1yl]carbonyl]-2-(4-methylphenyl)benzanilide.

Melting point: 256°–258° C. ¹H-NMR (δppm in DMSO-d₆, TMS internal standard): 2.28 (3H, s), 2.40 (2H, m), 2.62 (3H, d), 3.06 (1H, m), 4.82 (1H, m), 6.68 (1H, s), 6.71 (1H, d), 7.10–7.60 (total 15H), 8.41 (1H, d), 10.29 (1H, s) MS (FAB): 566 (M++1).

(Example 22)

With ice-cooling, 0.28 ml of diethyl cyanomethylphosphonate was added to 20 ml of tetrahydrofuran suspension of 70 mg 60% sodium hydride and the mixture was stirred for 30 minutes. 4'-[(4,4-Difluoro-5-oxo-2,3,4,5-tetrahydro-1H-1-benzazepin-1-yl]carbonyl]-2-(4methylphenyl) benzanilide (220 mg) was added to the reaction solution, and the mixture was stirred for 3 hours under ice-cooling and then for 1 hour at room temperature. The reaction solution was poured into ice water and extracted with ethyl acetate. The ethyl acetate layer was washed with saturated sodium chloride aqueous solution and dried over anhydrous magnesium sulfate, and then the solvent was evaporated. The resulting residue was purified by applying it to silica gel column chromatography, which was eluted with n-hexane and ethyl acetate by changing their mixing ratio from 4:1 to 3:1 by volume, and the residue obtained from the eluates was recrystallized from chloroform-n-hexane to obtain 100 mg of (Z)- and (E)-4'-[(5-cyanomethylene-4,4-difluoro-2,3, 4,5-tetrahydro-1H-1-benzazepin-1-yl)carbonyl]-2-(4methylphenyl)benzanilide.

Compound 22 (a)
(z) form
Melting point: 133°–135° C. $^1$H-NMR (δppm in CDCl$_3$, TMS internal standard): 2.36 (3H, s), 2.50 (2H, m), 3.25 (1H, m), 5.05 (1H, m), 5.79 (1H, s), 6.72 (1H, d), 6.90–7.60 (total 14H), 7.74 (1H, d) MS (FAB): 534 (M$^+$+1).

Compound 22 (b)
(E) form
Melting point: 202°–205° C. $^1$H-NMR (δppm in CDCl$_3$, TMS internal standard): 2.34 (3H, s), 2.50 (2H, m), 3.25 (1H, m), 5.05 (1H, m), 6.20 (1H, s), 6.75 (1H, d), 7.0–7.6 (total 14H), 7.74 (1H, d) MS (FAB): 534 (M$^+$+1).

(Example 23)

(Z)-[4,4-Difluoro-1-[4-(2-phenylbenzoylamino)benzoyl]-2,3,4,5-tetrahydro-1H-1-benzazepin-5-ylidene]acetic acid (250 mg) and 75 mg of 1-hydroxybenzotriazole were dissolved in 10 ml of methylene chloride and 5 ml of acetonitrile, and 107 mg of 1-ethyl-3(dimethylaminopropyl) carbodiimide hydrochloride was added to the solution under ice-cooling. Next, 0.088 ml of N-ethylpiperazine was added and the mixture was stirred overnight at room temperature. Then, 1N sodium hydroxide aqueous solution was added to the reaction solution, and the mixture was extracted with chloroform and dried over anhydrous potassium carbonate. After evaporation of the solvent, the resulting residue was applied to silica gel column chromatography, which was eluted with chloroform-methanol (97:3, v/v) to obtain 293 mg of free base. Next, this product was dissolved in methanol and converted into hydrochloride by adding 4N hydrochloric acid ethyl acetate solution, and then the solvent was evaporated under a reduced pressure. The resulting residue was recrystallized from ethanol-diethyl ether to obtain 221 mg of (Z)-4'-[[5-[(4-ethyl-1-piperazinyl) carbonylmethylene]-4,4-difluoro-2,3,4,5-tetrahydro-1H-1-benzazepin-1-yl]carbonyl]-2-phenylbenzanilide hydrochloride.

Melting point: 189°–191° C. $^1$H-NMR (δppm in DMSO-d$_6$, TMS internal standard): 1.27 (3H, t), 2.41 (2H, m), 2.78–3.30 (total 6H), 3.52 (2H, m), 3.64 (1H, m), 4.10 (1H, m), 4.46 (1H, m), 4.86 (1H, m), 6.77 (1H, s), 6.82 (1H, m), 7.01 (2H, m), 7.20 (1H, m), 7.24–7.41 (total 8H), 7.43–7.51 (total 2H), 7.52–7.58 (total 3H), 10.34 (1H, s), 11.15 (1H, m) MS (FAB): 635 (M$^+$+1).

(Example 24)

(Z)-[4,4-Difluoro-1-[4-(2phenylbenzoylamino)benzoyl]-2,3,4,5-tetrahydro-1H-1-benzazepin-5-ylidene]acetic acid (250 mg) and 75 mg of 1-hydroxybenzotriazole were dissolved in 10 ml of methylene chloride and 5 ml of acetonitrile, and 107 mg of 1-ethyl-3(dimethylaminopropyl) carbodiimide hydrochloride was added to the solution under ice-cooling. Next, 0.088 ml of N-methylhomopiperazine was added and the mixture was stirred overnight at room temperature. Then, 1N sodium hydroxide aqueous solution was added to the reaction solution, and the mixture was extracted with chloroform and dried over anhydrous potassium carbonate. After evaporation of the solvent, the resulting residue was applied to silica gel column chromatography, which was eluted with chloroform-methanol (90:10, v/v) to obtain 240 mg of free base. Next, this product was dissolved in methanol and converted into hydrochloride by adding 4N hydrochloric acid ethyl acetate solution, and then the solvent was evaporated under a reduced pressure. The resulting residue was mixed with ethanoldiethyl ether to obtain 222 mg of (Z)-4'-[[4,4-difluoro-5-[[(4-methylhexahydro-1,4-diazepin-1-yl) carbonyl]methylene]-2,3,4,5-tetrahydro-1H-1-benzazepin-1-yl]carbonyl]-2-phenylbenzanilide hydrochloride in the form of colorless amorphous solid.

Elemental analysis data ($C_{38}H_{36}N_4O_3F_2 \cdot HCl \cdot 0.4H_2O$)

|  | C % | H % | N % | Cl % | F % |
|---|---|---|---|---|---|
| calcd. | 67.28 | 5.62 | 8.26 | 5.23 | 5.60 |
| found | 67.27 | 5.55 | 8.32 | 5.36 | 5.59 |

$^1$H-NMR (δppm in DMSO-d$_6$, TMS internal standard): 2.05–2.34 (total 2H), 2.35–2.55 (total 2H), 2.79 (3H, s), 2.92–4.08 (total 9H), 4.86 (1H, m), 6.74–6.89 (total 2H), 7.01 (2H, m), 7.19 (1H, m), 7.25–7.41 (total 8H), 7.42–7.52 (total 2H), 7.53–7.60 (total 3H), 10.35 (1H, s), 10.84 (1H, m) MS (FAB): 635 (M$^+$+1).

(Example 25)

(Z)-[4,4-difluoro-1-[4-(2-phenylbenzoylamino)benzoyl]-2,3,4,5-tetrahydro-1H-1-benzazepin-5-ylidene]acetic acid (250 mg) and 75 mg of 1-hydroxybenzotriazole were dissolved in 10 ml of methylene chloride and 5 ml of acetonitrile, and 107 mg of 1-ethyl-3-(dimethylaminopropyl)carbodiimide hydrochloride was added to the solution under ice-cooling. Next, 0.074 ml of N,N-dimethylethylenediamine was added to the reaction mixture, and the mixture was stirred overnight at room temperature. Then, 1N sodium hydroxide aqueous solution was added to the reaction solution, and the mixture was extracted with chloroform and dried over anhydrous potassium carbonate. After evaporation of the solvent, the resulting residue was applied to silica gel column chromatography, which was eluted with chloroform-methanol (94:6, v/v) to obtain 261 mg of free base. Next, this product was dissolved in methanol and converted into hydrochloride by adding 4N hydrochloric acid ethyl acetate solution, and then the solvent was evaporated under a reduced pressure. Chloroform-diethyl ether was added to the resulting residue to obtain 200 mg of (Z)-4'-[[4,4-difluoro-5-[[N-(2-dimethylaminoethyl)carbamoyl]methylene]-2,3,4, 5-tetrahydro-1H-1-benzazepin-1-yl]carbonyl]-2-phenylbenzanilide hydrochloride in the form of colorless amorphous solid.

$^1$H-NMR (δppm in DMSO-d$_6$, TMS internal standard): 2.39 (1H, m), 2.65 (1H, m), 2.81 (6H, s), 3.09 (1H, m), 3.16 (2H, m), 3.49 (2H, m), 4.88 (1H, m), 6.53 (1H, s), 6.77 (1H, m), 7.02 (2H, m), 7.17 (1H, m), 7.24–7.41 (total 9H), 7.42–7.51

(total 2H), 7.52–7.60 (total 2H), 8.60 (1H, t), 9.99 (1H, m), 10.31 (1H, s) MS (FAB): 609 (M⁺+1).

(Example 26)

Using 250 mg of (Z)-[4,4-difluoro-1-[4-(2phenylbenzoylamino)benzoyl]-2,3,4,5-tetrahydro-1H-1-benzazepin-5-ylidene]acetic acid and 0.097 ml of N-benzylpiperazine, a similar procedure as in Example 23 was repeated and the product was recrystallized from acetonitrile-ether to obtain 200 mg of (Z)-4'-[[5-[(4-benzyl-1-piperazinyl)carbonylmethylene]-4,4-difluoro-2,3,4,5-tetrahydro- 1H-1-benzazepin-1-yl)carbonyl]-2-phenylbenzanilide hydrochloride.
Melting point: 164°–169° C. ¹H-NMR (67 ppm in DMSO-d₆, TMS internal standard): 2.41 (2H, m), 2.84–3.25 (total 4H), 3.30–3.46 (total 2H), 3.63 (1H, m), 4.02 (1H, m), 4.33–4.51 (3H, m), 4.87 (1H, m), 6.76 (1H, s), 6.81 (1H, m), 7.00 (2H, m), 7.19 (1H, m), 7.24–7.41 (total 8H), 7.42–7.77 (total 10H), 10.33 (1H, s), 11.19 (1H, m) MS (FAB): 697 (M++1).

(Example 27)

Using 250 mg of (Z)-[4,4-difluoro-1-[4-(2Phenylbenzoylamino)benzoyl]-2,3,4,5-tetrahydro-1H-1-benzazepin-5-ylidene]acetic acid and 0.089 ml of N,N-dimethyl-1,3-propanediamine, a similar procedure as in Example 24 was repeated to obtain 245 mg of (Z)-4'-[[4,4-difluoro-5-[[N-(3-dimethylaminopropyl)carbamoyl]methylene]- 2,3,4,5-tetrahydro-1H-1-benzazepin-1-yl]carbonyl]-2-phenylbenzanilide hydrochloride in the form of colorless amorphous solid.
¹H-NMR (δppm in DMSO-d₆, TMS internal standard): 1.81–1.92 (total 2H), 2.39 (1H, m), 2.67 (1H, m), 2.73 (6H, s), 2.96–3.30 (total 5H), 4.88 (1H, m), 6.52 (1H, s), 6.76 (1H, m), 7.02 (2H, m), 7.12–7.41 (total 9H), 7.42–7.51 (total 3H), 7.52–7.60 (total 2H), 8.51 (1H, t), 10.32 (1H, s), 10.59 (1H, m) MS (FAB): 623 (M⁺+1).

(Example 28)

Using 220 mg of (Z)-[4,4-difluoro-1-[4-(2phenylbenzoylamino)benzoyl]-2,3,4,5-tetrahydro-1H-1-benzazepin-5-ylidene]acetic acid and 205 mg of homopiperazine, a similar procedure as in Example 24 was repeated to obtain 220 mg of (Z)-4'-[[[5-[(hexahydro-1,4-diazepin-1-yl)carbonyl]methylene]-4,4-difluoro-2,3,4,5-tetrahydro-1H-1-benzazepin-1-yl]carbonyl]-2-phenylbenzanilide hydrochloride in the form of colorless amorphous solid.
¹H-NMR (δppm in DMSO-d₆, TMS internal standard): 1.97–2.10 (total 2H), 2.41 (2H, m), 3.16 (5H, m), 3.50–3.92 (total 5H), 4.87 (1H, m), 6.76–6.86 (total 2H), 7.01 (2H, m), 7.20 (1H, m), 7.24–7.41 (total 8H), 7.43–7.61 (total 5H), 8.96 (1H, m), 10.34 (1H, s) MS (FAB): 621 (M++1).

(Example 29)

Using 427 mg of 2-(2-methylphenyl)benzoic acid, 0.233 ml of oxalyl chloride and 500 mg of methyl (Z)-[1-(4-aminobenzoyl)-4,4-difluoro-2,3,4,5-tetrahydro-1H-1-benzazepin-5-ylidene]acetate, a similar procedure as in Reference Example 8 was repeated to obtain 603 mg of methyl (Z)-[4,4-difluoro-1-[4-[2-(2-methylphenyl)benzoyl]amino]benzoyl-2,3,4,5-tetrahydro-1H-1-benzazepin-5-ylidene]acetate.
¹H-NMR (8 ppm in CDCl₃, TMS internal standard): 2.06 (3H, s), 2.27–2.75 (total 2H), 3.24 (1H, m), 3.83 (3H, s), 5.01 (1H, m), 6.17 (1H, s), 6.65 (1H, m), 6.84 (2H, d), 6.99 (2H, d), 7.07 (1H, t), 7.09 (1H, s), 7.20–7.39 (total 7H), 7.50 (1H, t), 7.56 (1H, t), 8.07 (1H, d) MS (FAB): 567 (M⁺+1).

(Example 30)

Methyl (Z)-[1-(4-aminobenzoyl)-4,4-difluoro-2,3,4,5-tetrahydro-1H-1-benzazepin-5-ylidene]acetate (500 mg) and 0.373 ml of triethylamine were dissolved in 5 ml of methylene chloride, 0.210 ml of 2-methylbenzoyl chloride was added dropwise to the resulting solution under ice-cooling and then the mixture was stirred at room temperature for 2 hours. Saturated sodium bicarbonate aqueous solution was added and the mixture was extracted with methylene chloride. The resulting organic layer was dried over anhydrous magnesium sulfate, and the solvent was evaporated under a reduced pressure. The resulting residue was applied to column chromatography, which was eluted with a mixed solvent of ethyl acetate and hexane (1:1, v/v) to obtain 651 mg of methyl (Z)-[4,4-difluoro-1-[4-(2-methylbenzoyl)amino]benzoyl]-2,3,4,5-tetrahydro-1H-1-benzazepin-5-ylidene]acetate.
Elemental analysis data ($C_{28}H_{24}N_2O_4F_2$)

|  | C % | H % | N % | F % |
|---|---|---|---|---|
| calcd. | 68.56 | 4.93 | 5.71 | 7.75 |
| found | 68.33 | 4.95 | 5.71 | 7.73 |

¹H-NMR (δppm in CDCl₃, TMS internal standard): 2.02–2.82 (total 2H), 2.47 (3H, s), 3.21 (1H, m), 3.83 (3H, s), 5.06 (1H, m), 6.21 (1H, s), 6.73 (1H, d), 7.12–7.50 (total 12H) MS (EI): 490 (M⁺).

(Example 31)

Using 500 mg of methyl (Z)-[1-(4-aminobenzoyl)-4,4-difluoro-2,3,4,5-tetrahydro-1H-1-benzazepin-5-ylidene] acetate and 0.210 ml of 2-methoxybenzoyl chloride, a similar procedure as in Example 30 was repeated to obtain 644 mg of methyl (Z)-[4,4-difluoro-1-[4-(2methoxybenzoyl)amino]benzoyl-2,3,4,5-tetrahydro-1H-1-benzazepin-5-ylidene]acetate.
¹H-NMR (8 ppm in CDCl₃, TMS internal standard): 2.26–2.84 (total 2H), 3.26 (1H, m), 3.83 (3H, s), 4.03 (3H, s), 5.03 (1H, m), 6.21 (1H, s), 6.73 (1H, m), 7.02 (1H, d), 7.09–7.28 (total 5H), 7.37 (1H, d), 7.50 (3H, m), 8.23 (1H, m), 9.84 (1H, m) MS (EI): 506 (M⁺+1).

(Example 32)

Using 500 mg of methyl (Z)-[1-(4-aminobenzoyl)-4,4-difluoro-2,3,4,5-tetrahydro-1H-1-benzazepin-5-ylidene] acetate and 245 mg of 2-ethoxybenzoic acid, a similar procedure as Reference Example 8 was repeated to obtain 697 mg of methyl (Z)-[1-[4-(2-ethoxybenzoyl)amino] benzoyl-4,4-difluoro-2,3,4,5-tetrahydro-1H-1-benzazepin-5-ylidene]acetate.
¹H-NMR (δppm in CDCl₃, TMS internal standard): 1.61 (3H, t), 2.32–2.82 (total 2H), 3.24 (1H, m), 3.84 (3H, s), 4.26 (2H, q), 5.03 (1H, m), 6.22 (1H, s), 6.73 (1H, m), 7.02 (1H, d), 7.06–7.18 (total 4H), 7.24 (1H, t), 7.37 (1H, d), 7.47 (3H, m), 8.24 (1H, m), 10.12 (1H, m) MS (EI): 521 (M⁺+1).

(Example 33)

Using 500 mg of methyl (Z)-[1-(4-aminobenzoyl)-4,4-difluoro-2,3,4,5-tetrahydro-1H-1-benzazepin-5-ylidene] acetate and 264 mg of 2-isopropoxybenzoic acid, a similar procedure as in Reference Example 8 was repeated to obtain 693 mg of methyl (Z)-[4,4-difluoro-1-[4-(2-isopropoxybenzoyl)amino]benzoyl-2,3,4,5-tetrahydro-1H-1-benzazepin-5-ylidene]acetate.

$^1$H-NMR (δppm in CDCl$_3$, TMS internal standard): 1.50 (6H, d), 2.35–2.82 (total 2H), 3.23 (1H, m), 3.84 (3H, s), 4.82 (1H, m), 5.07 (1H, m), 6.22 (1H, s), 6.73 (1H, m), 7.00 (1H, d), 7.08–7.18 (total 4H), 7.24 (1H, t), 7.38 (1H, d), 7.47 (3H, m), 8.24 (1H, m), 10.25 (1H, m) MS (FAB): 521 (M$^+$+1).

(Example 34)

Using 600 mg of methyl (Z)-[1-(4-aminobenzoyl)-4,4-difluoro-2,3,4,5-tetrahydro-1H-1-benzazepin-5-ylidene]acetate and 0.238 ml of 3-methoxybenzoyl chloride, a similar procedure as in Example 30 was repeated to obtain 787 mg of methyl (Z)-[4,4-difluoro-1-[4-(3-methoxybenzoyl)amino]benzoyl- 2,3,4,5-tetrahydro-1H-1-benzazepin-5-ylidene]acetate.

$^1$H-NMR (δppm in CDCl$_3$, TMS internal standard): 2.30–2.82 (total 2H), 3.26 (1H, m), 3.84 (3H, s), 3.85 (3H, s), 5.05 (1H, m), 6.21 (1H, s), 6.72 (1H, m), 7.02 (1H, d), 7.06–7.19 (total 4H), 7.24 (1H, t), 7.31–7.40 (total 4H), 7.46 (2H, d), 8.85 (1H, s) MS (FAB): 506 (M$^+$+1).

(Example 35)

Using 600 mg of methyl (Z)-[1-(4-aminobenzoyl)-4,4-difluoro-2,3,4,5-tetrahydro-1H-1-benzazepin-5-ylidene]acetate and 0.214 ml of 2-chlorobenzoyl chloride, a similar procedure as in Example 30 was repeated to obtain 820 mg of methyl (Z)[1-[4-(2-chlorobenzoyl)amino]benzoyl-4,4-difluoro-2,3,4,5-tetrahydro-1H-1-benzazepin-5-ylidene] acetate.

$^1$H-NMR (δppm in CDCl$_3$, TMS internal standard): 2.27–2.82 (total 2H), 3.26 (1H, m), 3.83 (3H, s), 5.04 (1H, m), 6.21 (1H, s), 6.73 (1H, m), 7.10–7.20 (total 3H), 7.26 (1H, t), 7.34–7.50 (total 6H), 7.72 (1H, d), 7.98 (1H, s) MS (EI): 510, 512 (M$^+$).

(Example 36)

Using 600 mg of methyl (Z)-[1-(4-aminobenzoyl)-4,4-difluoro-2,3,4,5-tetrahydro-1H-1-benzazepin-5-ylidene]acetate and 0.214 ml of 3-chlorobenzoyl chloride, a similar procedure as in Example 30 was repeated to obtain 820 mg of methyl (Z)-[1-[4-(3-chlorobenzoyl)amino]benzoyl-4,4-difluoro-2,3,4,5-tetrahydro-1H-1-benzazepin-5-ylidene] acetate.

$^1$H-NMR (δppm in CDCl$_3$, TMS internal standard): 2.27–2.82 (total 2H), 3.26 (1H, m), 3.84 (3H, s), 5.06 (1H, m), 6.21 (1H, s), 6.71 (1H, m), 7.07–7.17 (total 3H), 7.24 (1H, t), 7.36–7.47 (total 4H), 7.71 (1H, d), 7.82 (1H, s), 7.94 (1H, s) MS 510, 512 (M$^+$).

(Example 37)

Using 3.00 g of methyl (Z)-[1-(4-aminobenzoyl)-4,4-difluoro-2,3,4,5-tetrahydro-1H-1-benzazepin-5-ylidene]acetate and 0.214 ml of 2-nitrobenzoic acid, a similar procedure as in Reference Example 8 was repeated to obtain 3.75 g of methyl (Z)-[4,4-difluoro-1-[4-(2-nitrobenzoyl)amino]benzoyl-2,3,4,5-tetrahydro-1H-1-benzazepin-5-ylidene]acetate.

$^1$H-NMR (δppm in CDCl$_3$-DMSO-d$_6$, TMS internal standard): 2.25–2.82 (total 2H), 3.24 (1H, m), 3.83 (3H, s), 5.04 (1H, m), 6.24 (1H, s), 6.75 (1H, m), 7.10–7.20 (total 3H), 7.14 (1H, t), 7.38 (1H, m), 7.52 (2H, d), 7.57–7.67 (total 2H), 7.72 (1H, t), 8.08 (1H, d), 10.09 (1H, s) MS (FAB): 522 (M$^+$+1).

(Example 38)

Methyl (Z)-[4,4-difluoro-[1-[4-(2-nitrobenzoyl)amino] benzoyl-2,3,4,5-tetrahydro-1H-1-benzazepin-5-ylidene] acetate (4.00 g) was suspended in 100 ml of ethyl acetate, 10.4 g of stannous chloride monohydrate was added to the suspension and the mixture was heated under reflux for 3 hours. Saturated sodium bicarbonate aqueous solution was added to the reaction solution under ice-cooling, and the thus precipitated insoluble matter was removed by filtration using celite, and the filtrate was separated. The organic layer was dried over anhydrous magnesium sulfate, and the solvent was then evaporated. By crystallizing the resulting residue with ethanol-diethyl ether, 1.79 g of methyl (Z)-[1-[4-(2-aminobenzoyl)amino]benzoyl-4,4-difluoro-2,3,4,5-tetrahydro-1H-1-benzazepin-5-ylidene]acetate was obtained as a colorless amorphous solid.

$^1$H-NMR (δppm in DMSO-d$_6$, TMS internal standard): 2.39–2.56 (total 2H), 3.12 (1H, m), 3.76 (3H, s), 4.87 (1H, m), 6.28 (2H, s), 6.56 (1H, t), 6.73 (1H, d), 6.76 (1H, s), 6.85 (1H, m), 7.05 (2H, d), 7.17–7.23 (total 2H), 7.31 (1H, t), 7.41 (1H, d), 7.53–7.62 (total 3H), 10.09 (1H, s) MS (FAB): 492 (M$^+$+1).

(Example 39)

Methyl (Z)-[1-[4-(2-aminobenzoyl)amino]benzoyl-4,4-difluoro-2,3,4,5-tetrahydro-1H-1-benzazepin-5-ylidene] acetate (1.10 g) was dissolved in 10 ml of acetic acid, the solution was mixed with 511 mg of acetonylacetone and, the mixture heated for 2 hours under reflux. The solvent was evaporated water was added to the resulting residue, and the mixture was extracted with chloroform-methanol mixed solvent. After evaporating the organic layer, the resulting residue was applied to silica gel column chromatography, which was eluted with chloroform-methanol (97:3, v/v), and the thus eluted compound was crystallized from ethyl acetate and hexane to obtain 500 mg of methyl (Z)-[4,4-difluoro-1-[4-[2-(2,5-dimethylpyrrol-1-yl)benzoyl]amino] benzoyl-2,3,4,5-tetrahydro-1H-1-benzazepin-5-ylidene] acetate.

$^1$H-NMR (δppm in CDCl$_3$, TMS internal standard): 2.28–2.80 (total 2H), 3.22 (1H, m), 3.83 (3H, s), 5.02 (1H, m), 6.20 (1H, s), 6.70 (1H, m), 7.08–7.16 (total 3H), 7.24–7.31 (total 3H), 7.38 (1H, d), 7.44 (1H, d), 7.57–7.66 (total 2H), 7.82 (1H, m), 8.09 (1H, s), 8.20 (1H, s), 8.34 (1H, s) MS (EI): 569 (M$^+$).

(Example 40)

Using 948 mg of methyl (Z)-[1-(4-aminobenzoyl)-4,4-difluoro-2,3,4,5-tetrahydro-1H-1-benzazepin-5-ylidene] acetate and 530 mg of 2-(1H-1,2,4-triazol-1-yl)benzoic acid, a similar procedure as in Reference Example 8 was repeated to obtain 1.23 g of methyl (Z)-[4,4-difluoro-1-[4-[2-(1H-1,2,4-triazol-1-yl)benzoyl]amino]benzoyl-2,3,4,5-tetrahYdro-1H-1- benzazepin-5-ylidene]acetate.

$^1$H-NMR (δppm in CDCl$_3$, TMS internal standard): 1.97 (6H, m), 2.28–2.80 (total 2H), 3.22 (1H, m), 3.83 (3H, s), 5.04 (1H, m), 6.08 (2H, s), 6.20 (1H, s), 6.64– 6.74 (total 2H), 6.96–7.30 (total 7H), 7.37 (1H, d), 7.56–7.68 (total 2H), 8.37 (1H, d) MS (FAB): 544 (M$^+$+1).

(Example 41)

2-(1H-Imidazol-1-yl)benzoic acid (222 mg) and 160 mg of 1-hydroxybenzotriazole were dissolved in 10 ml of methylene chloride, and 10 ml of a methylene chloride solution containing 227 mg of 1-ethyl-3(dimethylaminopropyl)carbodiimide hydrochloride was added dropwise under ice-cooling. Next, 400 mg of methyl (Z)-[1-(4-aminobenzoyl)-4,4-difluoro-2,3,4,5-tetrahydro-1H-1-benzazepin-5-ylidene] acetate was added and the mixture was stirred at room temperature for 3 days. Then, 1N Sodium hydroxide was added to the reaction solution, and the mixture was extracted with chloroform and dried over anhydrous potassium carbonate. After evaporation of the solvent, the resulting residue was applied to silica gel column chromatography, which was eluted with chloroform-methanol (95:5, v/v) to obtain 270 mg of methyl (Z)-[4,4-difluoro-1-[4-[2-(1H-imidazol-1-yl)benzoyl]amino]benzoyl-2,3,4,5-tetrahydro-1H-1-benzazepin-5-ylidene]acetate.

$^1$H-NMR (δppm in CDCl$_3$, TMS internal standard): 2.28–2.82 (total 2H), 3.22 (1H, m), 3.83 (3H, s), 5.03 (1H, m), 6.20 (1H, s), 6.69 (1H, m), 7.03–7.41 (total 11H), 7.53–7.64 (total 2H), 7.66 (1H, s), 7.83 (1H, d) MS (FAB): 543 (M++1).

(Example 42)

Using 4.31 g of methyl (Z)-[1-(4-aminobenzoyl)-4,4-difluoro-2,3,4,5-tetrahydro-1H-1-benzazepin-5-ylidene] acetate and 3.0 g of 2-(2-ethyl-1H-imidazol-1-yl)benzoic acid, a similar procedure as in Reference Example 8 was repeated to obtain 5.0 g of methyl (Z)-[1-[4-[2-(2-ethyl-1H-imidazol-1yl)benzoyl]amino]benzoyl-4,4-difluoro-2,3,4,5-tetrahydro-1H-1-benzazepin-5-ylidene]acetate.

Melting point: 230°–231° C. $^1$H-NMR (δppm in DMSO-d$_6$, TMS internal standard): 1.04 (2H, t), 2.40 (2H, q), 3.11 (1H, br), 3.74 (3H, s), 4.86 (1H, br), 6.70–6.85 (total 3H), 10.4 (1H, s) MS (FAB): 571 (M$^+$+1).

(Example 43)

Using 600 mg of methyl (Z)-[1-(4-aminobenzoyl)-4,4-difluoro-2,3,4,5-tetrahydro-1H-1-benzazepin-5-ylidene] acetate and 266 mg of o-tolylacetic acid, a similar procedure as in Reference Example 8 was repeated to obtain 683 mg of methyl (Z)-[4,4-difluoro-1-[4-(2-methylphenyl)acetylamino]benzoyl-2,3,4,5-tetrahydro-1H-1-benzazepin-5-ylidene]acetate.

$^1$H-NMR (δppm in CDCl$_3$, TMS internal standard): 2.29 (3H, s), 2.35–2.80 (total 2H), 3.23 (1H, m), 3.70 (2H, s), 3.82 (3H, s), 5.04 (1H, m), 6.15 (1H, s), 6.67 (1H, m), 6.93 (1H, s), 7.06–7.14 (total 3H), 7.17–7.29 (total 6H), 7.36 (1H, d) MS (FAB): 505 (M$^+$+1).

(Example 44)

Using 500 mg of methyl (Z)-[1-(4-aminobenzoyl)-4,4-difluoro-2,3,4,5-tetrahydro-1H-1-benzazepin-5-ylidene] acetate and 245 mg of 2-methoxyphenylacetic acid, a similar procedure as in Reference Example 8 was repeated to obtain 665 mg of methyl (Z)-[4,4-difluoro-1-[4-(2-methoxyphenyl)acetylamino]benzoyl-2,3,4,5-tetrahydro-1H-1-benzazepin-5-ylidene]acetate.

$^1$H-NMR (δppm in CDCl$_3$, TMS internal standard): 2.26–2.80 (total 2H), 3.23 (1H, m), 3.67 (2H, s), 3.82 (3H, s), 3.91 (3H, s), 5.04 (1H, m), 6.17 (1H, s), 6.67 (1H, m), 6.93–7.01 (total 2H), 7.04–7.13 (total 3H), 7.19–7.38 (total 6H), 7.76 (1H, s) MS (FAB): 521 (M$^+$+1).

(Example 45)

Using 600 mg of methyl (Z)-[1-(4-aminobenzoyl)-4,4-difluoro-2,3,4,5-tetrahydro-1H-1-benzazepin-5-ylidene] acetate and 0.261 ml of 2-trifluoromethylbenzoyl chloride, a similar procedure as in Example 30 was repeated to obtain 861 mg of methyl (Z)-[4,4-difluoro-1-[4-(2-trifluoromethylbenzoyl)amino]benzoyl-2,3,4,5-tetrahydro-1H-1-benzazepin-5-ylidene]acetate.

$^1$H-NMR (δppm in CDCl$_3$, TMS internal standard): 2.30–2.82 (total 2H), 3.24 (1H, m), 3.83 (3H, s), 5.04 (1H, m), 6.21 (1H, s), 6.73 (1H, m), 7.09–7.19 (total 3H), 7.26 (1H, t), 7.36–7.44 (total 3H), 7.53–7.66 (total 4H), 7.74 (1H, d) MS (EI): 544 (M$^+$).

(Example 46)

Using 600 mg of methyl (Z)-[1-(4-aminobenzoyl)-4,4-difluoro-2,3,4,5-tetrahydro-1H-1-benzazepin-5-ylidene] acetate and 0.337 ml of 1-naphthoyl chloride, a similar procedure as in Example 30 was repeated to obtain 860 mg of methyl (Z)-[4,4-difluoro-1-[4-(1-naphthylcarbonyl)amino]benzoyl-2,3,4,5-tetrahydro-1H-1-benzazepin-5-ylidene]acetate.

$^1$H-NMR (δppm in CDCl$_3$, TMS internal standard): 2.25–2.81 (total 2H), 3.29 (1H, m), 3.84 (3H, s), 5.03 (1H, m), 6.22 (1H, s), 6.74 (1H, m), 7.13–7.21 (total 3H), 7.27 (1H, t), 7.39 (1H, d), 7.44–7.57 (total 4H), 7.69 (1H, d), 7.72 (1H, s), 7.89 (1H, m), 7.97 (1H, d), 8.29 (1H, m) MS (FAB): 527 (M$^+$+1).

(Example 47)

Using 600 mg of methyl (Z)-[1-(4-aminobenzoyl)-4,4-difluoro-2,3,4,5-tetrahydro-1H-1-benzazepin-5-Ylidene] acetate and 222 mg of 1-methyl-2-pyrrolcarbonic acid, a similar procedure as in Reference Example 8 was repeated to obtain 480 mg of methyl (Z)-[4,4-difluoro-1-[4-(1-methyl-2pyrrolyl)carbonylamino]benzoyl-2,3,4,5-tetrahYdro-1H-1-benzazepin-5-ylidene]acetate.

$^1$H-NMR (δppm in CDCl$_3$, TMS internal standard): 2.28–2.82 (total 2H), 3.24 (1H, m), 3.83 (3H, s), 3.93 (3H, s), 5.04 (1H, m), 6.11 (1H, m), 6.19 (1H, s), 6.66 (1H, m), 6.72 (1H, m), 6.77 (1H, m), 7.08–7.18 (total 3H), 7.23 (1H, t), 7.36–7.40 (total 3H), 7.65 (1H, s) MS (EI): 479 (M$^+$).

(Example 48)

Using 600 mg of methyl (Z)-[1-(4-aminobenzoyl)-4,4-difluoro-2,3,4,5-tetrahydro-1H-1-benzazepin-5-ylidene] acetate and 252 mg of 3-methyl-2-thiophenecarboxylic acid, a similar procedure as in Reference Example 8 was repeated to obtain 722 mg of methyl (Z)-[4,4-difluoro-1-[4-(3-methyl-2thienyl)carbonylamino]benzoyl-2,3,4,5-tetrahydro-1H-1-benzazepin-5-ylidene]acetate.

$^1$H-NMR (δppm in CDCl$_3$, TMS internal standard): 2.42 (1H, m), 2.55 (3H, s), 2.68 (1H, m), 3.26 (1H, m), 3.83 (3H, s), 5.05 (1H, m), 6.19 (1H, s), 6.72 (1H, m), 6.93 (1H, d), 7.11 (1H, t), 7.16 (2H, d), 7.24 (1H, t), 7.32 (1H, d), 7.36 (1H, d), 7.40 (2H, d), 7.49 (1H, d) MS (FAB): 497 (M$^+$+1).

(Example 49)

Using 500 mg of methyl (Z)-[1-(4-aminobenzoyl)-4,4-difluoro-2,3,4,5-tetrahydro-1H-1-benzazepin-5-ylidene] acetate and 169 mg of 3-methyl-2-furancarboxylic acid, a similar procedure as in Reference Example 8 was repeated to obtain 414 mg of methyl (Z)-[4,4-difluoro-1-[4-(3-methyl-2-furyl)carbonylamino]benzoyl- 2,3,4,5-tetrahydro-1H-1-benzazepin-5-ylidene]acetate.

$^1$H-NMR (δppm in CDCl$_3$, TMS internal standard): 2.22–2.80 (total 2H), 2.41 (3H, s), 3.23 (1H, m), 3.83 (3H, s), 5.05 (1H, m), 6.19 (1H, s), 6.38 (1H, s), 6.71 (1H, m), 7.10 (1H, t), 7.15 (2H, d), 7.23 (1H, t), 7.32–7.40 (total 2H), 7.45 (1H, d), 8.02 (1H, s) MS (FAB): 481 (M$^+$+1).

(Example 50)

Using 269 mg of 2,3-dimethoxybenzoic acid and 500 mg of methyl (Z)-[1-(4-aminobenzoyl)-4,4-difluoro-2,3,4,5-tetrahydro-1H-1-benzazepin-5-ylidene]acetate, a similar procedure as in Reference Example 8 was repeated to obtain 711 mg of methyl (Z)-[1-[4-(2,3dimethoxybenzoyl)amino]benzoyl-4,4-difluoro-2,3,4,5-tetrahydro-1H-1-benzazepin-5-ylidene]acetate.
$^1$H-NMR (δppm in CDCl$_3$, TMS internal standard): 2.27–2.80 (total 2H), 3.27 (1H, m), 3.84 (3H, s), 3.92 (3H, s), 3.96 (3H, s), 5.07 (1H, m), 6.22 (1H, s), 6.73 (1H, m), 7.08–7.26 (total 6H), 7.38 (1H, d), 7.49 (2H, d), 7.74 (1H, d), 10.07 (1H, s) MS (FAB): 537 (M$^+$+1).

(Example 51)

Using 296 mg of 2,6-dimethoxybenzoic acid chloride and 500 mg of methyl (Z)-[1-(4-aminobenzoyl)-4,4-difluoro-2,3,4,5-tetrahydro-1H-1-benzazepin-5-ylidene]acetate, a similar procedure as in Example 30 was repeated to obtain 677 mg of methyl (Z)-[1-[4-(2,6-dimethoxybenzoyl)amino]benzoyl-4,4-difluoro-2,3,4,5-tetrahydro-1H-1-benzazepin-5ylidene]acetate.
$^1$H-NMR (δppm in CDCl$_3$, TMS internal standard): 2.30–2.80 (total 2H), 3.24 (1H, m), 3.81 (6H, s), 3.83 (3H, s), 5.07 (1H, m), 6.20 (1H, s), 6.58 (2H, d), 6.74 (1H, d), 7.11–7.18 (total 3H), 7.26 (1H, d), 7.31 (1H, t), 7.38 (1H, d), 7.40–7.52 (total 4H) MS (FAB): 537 (M$^+$+1).

(Example 52)

Using 280 mg of 1-phenylcyclopentylcarboxylic acid and 500 mg of methyl (Z)-[1-(4-aminobenzoyl)-4,4-difluoro-2, 3,4,5-tetrahydro-1H-1-benzazepin-5-ylidene]acetate, a similar procedure as in Reference Example 8 was repeated to obtain 533 mg of methyl (Z)-[4,4-difluoro-1-[4-(1-phenylcyclopentylcarbonyl)amino]benzoyl-2,3,4,5-tetrahydro-1H-1-benzazepin-5-ylidene]acetate.
$^1$H-NMR (δppm in CDCl$_3$, TMS internal standard): 1.71 (2H, m), 1.85 (2H, m), 2.07 (2H, m), 2.20–2.80 (total 4H), 3.21 (1H, m), 3.81 (3H, s), 5.03 (1H, m), 6.13 (1H, s), 6.67 (1H, d), 6.78 (1H, s), 7.05 (2H, d), 7.09 (1H, t), 7.14 (2H, d), 7.22 (1H, t), 7.26–7.41 (total 6H) MS (FAB): 545 (M$^+$+1).

(Example 53)

Using 302 mg of 2-piperidinobenzoic acid and 500 mg of methyl (Z)-[1-(4-aminobenzoyl)-4,4-difluoro-2,3,4,5-tetrahydro-1H-1-benzazepin-5-ylidene]acetate, a similar procedure as in Reference Example 8 was repeated to obtain 711 mg of methyl (Z)-[4,4-difluoro-1-[4-(2piperidinobenzoyl)amino]benzoyl-2,3,4,5-tetrahydro-1H-1-benzazepin-5-ylidene]acetate.
$^1$H-NMR (δppm in CDCl$_3$, TMS internal standard): 1.65 (2H, m), 1.77 (4H, m), 2.24–2.80 (total 2H), 2.97 (4H, m), 3.25 (1H, m), 3.84 (3H, s), 5.07 (1H, m), 6.23 (1H, s), 6.74 (1H, d), 7.11 (1H, t), 7.17 (2H, d), 7.21–7.31 (total 3H), 7.38 (1H, d), 7.47 (1H, t), 7.57 (2H, d), 8.23 (1H, d), 12.67 (1H, s) MS (FAB): 560 (M$^+$+1).

(Example 54)

Using 600 mg of methyl (Z)-[4,4-difluoro-1-[4-[2-(2-methylphenyl)benzoyl]amino]benzoyl-2,3,4,5-tetrahydro-1H-1-benzazepin-5-ylidene]acetate, a similar procedure as in Example 7 was repeated to obtain 500 mg of (Z)-[4,4-difluoro-[4-[2-(2-methylphenyl)benzoyl]amino]benzoyl-2, 3,4,5-tetrahydro-1H-1-benzazepin-5-ylidene]acetic acid.
$^1$H-NMR (δppm in CDCl$_3$-DMSO-d$_6$, TMS internal standard): 2.07 (3H, s), 2.23–2.84 (total 2H), 3.21 (1H, m), 5 00 (1H, m), 6.20 (1H, s), 6.64 (1H, m), 6.88 (2H, d), 7.00 (2H, d), 7.15–7.39 (total 9H), 7.47–7.59 (total 2H), 8.02 (1H, d) MS (FAB): 553 (M$^+$+1).

(Example 55)

Using 650 mg of methyl (Z)-[4,4-difluoro-1-[4-(2-methylbenzoyl)amino]benzoyl-2,3,4,5-tetrahydro-1H-1-benzazepin-5-ylidene]acetate, a similar procedure as in Example 7 was repeated to obtain 566 mg of (Z)-[4,4-difluoro-1-[4-(2-methylbenzoyl)amino]benzoyl-2,3,4,5-tetrahydro-1H-1-benzazepin-5-ylidene]acetic acid.
$^1$H-NMR (δppm in CDCl$_3$, TMS internal standard): 2.15–3.00 (total 2H), 2.43 (3H, s), 3.35 (1H, m), 5.02 (1H, m), 6.20 (1H, s), 6.75 (1H, m), 7.08–7.49 (total 12H), 7.67 (1H, br) MS (EI): 476 (M$^+$).

(Example 56)

Using 650 mg of methyl (Z)-[4,4-difluoro-1-[4-(2-methoxybenzoyl)amino]benzoyl-2,3,4,5-tetrahydro-1H-1-benzazepin-5-ylidene]acetate, a similar procedure as in Example 7 was repeated to obtain 566 mg of (Z)-[4,4-difluoro-1-[4-(2-methoxybenzoyl)amino]benzoyl-2,3,4,5-tetrahydro-1H-1-benzazepin-5-ylidene]acetic acid.
$^1$H-NMR (δppm in CDCl$_3$, TMS internal standard): 2.2–2.8 (total 2H), 3.26 (1H, m), 4.03 (3H, s), 5.03 (1H, m), 6.21 (1H, s), 6.73 (1H, m), 7.02 (1H, d), 7.09– 7.28 (total 5H), 7.37 (1H, d), 7.50 (3H, m), 8.23 (1H, m), 9.84 (1H, m) MS (EI): 493 (M$^+$+1).

(Example 57)

Using 695 mg of methyl (Z)-[1-[4-(2-ethoxybenzoyl)amino]benzoyl-4,4-difluoro-2,3,4,5-tetrahydro-1H-1-benzazepin-5-ylidene]acetate, a similar procedure as in Example 7 was repeated to obtain 670 mg of (Z)-[1-[4-(2-ethoxybenzoyl)amino]benzoyl-4,4-difluoro-2,3,4,5-tetrahydro-1H-1-benzazepin-5-ylidene]acetic acid.
$^1$H-NMR (δppm in CDCl$_3$, TMS internal standard): 1.59 (3H, t), 2.28–2.90 (total 2H), 3.28 (1H, m), 4.22 (2H, q), 5.03 (1H, m), 6.27 (1H, s), 6.73 (1H, m), 6.93 (1H, d), 7.06–7.18 (total 4H), 7.24 (1H, t), 7.26–7.30 (total 4H), 8.22 (1H, d), 10.16 (1H, m) MS (FAB): 507 (M$^+$+1).

(Example 58)

Using 683 mg of methyl (Z)-[4,4-difluoro-1-[4-(2-isopropoxybenzoyl)amino]benzoyl-2,3,4,5-tetrahydro-1H-1-benzazepin-5-ylidene]acetate, a similar procedure as in Example 7 was repeated to obtain 499 mg of (Z)-[4,4-difluoro-1-[4-(2-isopropoxybenzoyl)amino]benzoyl-2,3,4, 5-tetrahydro-1H-1-benzazepin-5-ylidene]acetic acid.
$^1$H-NMR (δppm in CDCl$_3$, TMS internal standard): 1.47 (6H, d), 2.28–2.86 (total 2H), 3.28 (1H, m), 4.79 (1H, m), 5.07 (1H, m), 6.27 (1H, s), 6.73 (1H, m), 6.98 (1H, d), 7.06–7.20 (total 4H), 7.24 (1H, t), 7.39 (1H, d), 7.41–7.50 (total 4H), 8.21 (1H, m), 10.26 (1H, m) MS (FAB): 521 (M$^+$+1).

(Example 59)

Using 787 mg of methyl (Z)-[4,4-difluoro-1-[4-(3-methoxybenzoyl)amino]benzoyl-2,3,4,5-tetrahydro-1H-1-benzazepin-5-ylidene]acetate, a similar procedure as in Example 7 was repeated to obtain 673 mg of (Z)-[4,4-difluoro-1-[4-(3-methoxybenzoyl)amino]benzoyl-2,3,4,5-tetrahydro-1H-1-benzazepin-5-ylidene]acetic acid.

$^1$H-NMR ($\delta$ppm in CDCl$_3$-DMSO-d$_6$, TMS internal standard): 2.25–2.92 (total 2H), 3.22 (1H, m), 3.86 (3H, s), 5.04 (1H, m), 6.24 (1H, s), 6.71 (1H, m), 7.03–7.13 (total 2H), 7.15 (1H, d), 7.22 (1H, t), 7.34–7.40 (total 2H), 7.44–7.48 (total 2H), 7.60 (2H, d), 9.34 (1H, s) MS (FAB): 493 (M$^+$+1).

(Example 60)

Using 788 mg of methyl (Z)-[1-[4-(2-chlorobenzoyl)amino]benzoyl-4,4-difluoro-2,3,4,5-tetrahydro-1H-1-benzazepin-5-ylidene]acetate, a similar procedure as in Example 7 was repeated to obtain 668 mg of (Z)-[1-[4-(2-chlorobenzoyl)amino]benzoyl-4,4-difluoro-2,3,4,5-tetrahydro-1H-1-benzazepin-5-ylidene]acetic acid.

$^1$H-NMR ($\delta$ppm in CDCl$_3$-DMSO-d$_6$, TMS internal standard): 2.15–2.82 (total 2H), 3.22 (1H, m), 5.03 (1H, m), 6.24 (1H, s), 6.72 (1H, m), 7.09–7.20 (total 3H), 7.25 (1H, t), 7.32–7.48 (total 4H), 7.50–7.65 (total 3H), 9.85 (1H, s) MS (FAB): 497,499 (M$^+$+1)

(Example 61)

Using 782 mg of methyl (Z)-[1-[4-(3-chlorobenzoyl)amino]benzoyl-4,4-difluoro-2,3,4,5-tetrahydro-1H-1-benzazepin-5-ylidene]acetate, a similar procedure as in Example 7 was repeated to obtain 631 mg of (Z)-[1-[4-(3-chlorobenzoyl)amino]benzoyl-4,4-difluoro-2,3,4,5-tetrahydro-1H-1-benzazepin-5-ylidene]acetic acid.

$^1$H-NMR ($\delta$ ppm in CDCl$_3$-DMSO-d$_6$, TMS internal standard): 2.43 (1H, m), 2.69 (1H, m), 3.24 (1H, m), 5.03 (1H, m), 6.24 (1H, s), 6.71 (1H, m), 7.09 (1H, t), 7.14 (2H, d), 7.22 (1H, t), 7.34–7.43 (total 2H), 7.48 (1H, d), 7.59 (2H, d), 7.81 (1H, d), 7.93 (1H, s), 9.53 (1H, s)

MS (FAB): 497, 499 (M$^+$+1)

(Example 62)

Using 730 mg of methyl (Z)-[4,4-difluoro-1-[4-(2-nitrobenzoyl)amino]benzoyl-2,3,4,5-tetrahydro-1H-1-benzazepin-5-ylidene]acetate, a similar procedure as in Example 7 was repeated to obtain 389 mg of (Z)-4,4-difluoro-1-[4-(2-nitrobenzoyl)amino]benzoyl-2,3,4,5-tetrahydro-1H-1-benzazepin-5-ylidene]acetic acid.

$^1$H-NMR ($\delta$ ppm in DMSO-d$_6$, TMS internal standard): 2.46 (2H, m), 3.11 (1H, m), 4.88 (1H, m), 6.68 (1H, s), 6.84 (1H, m), 7.09 (2H, d), 7.21 (1H, t), 7.31 (1H, t), 7.38 (1H, d), 7.50 (2H, d), 7.74–7.80 (total 2H), 7.86 (1H, t), 8.14 (1H, d), 10.74 (1H, s), 13.18 (1H, br)

MS (FAB): 478 (M$^+$+1)

(Example 63)

Using 600 mg of methyl (Z)-[1-[4-(2-aminobenzoyl)amino]benzoyl-4,4-difluoro-2,3,4,5-tetrahydro-1H-1-benzazepin-5-ylidene]acetate, a similar procedure as in Example 7 was repeated to obtain 370 mg of (Z)-[1-[4-(2-aminobenzoyl)amino]benzoyl-4,4-difluoro-2,3,4,5-tetrahydro-1H-1-benzazepin-5-ylidene]acetic acid.

$^1$H-NMR ($\delta$ ppm in DMSO-d$_6$, TMS internal standard): 2.46 (2H, m), 3.11 (1H, m), 3.33 (2H, br), 4.87 (1H, m), 6.56 (1H, t), 6.65 (1H, s), 6.76 (1H, d), 6.83 (1H, m), 7.06 (2H, d), 7.14–7.24 (total 2H), 7.30 (1H, t), 7.38 (1H, d), 7.56 (2H, d), 10.04 (1H, s), 13.20 (1H, br)

MS (FAB): 478 (M$^+$+1)

(Example 64)

Using 500 mg of methyl (Z)-4,4-difluoro-1-[4-[2-(2,5-dimethylpyrrol-1-yl)benzoyl]amino]benzoyl-2,3,4,5-tetrahydro-1H-1-benzazepin-5-ylidene]acetate, a similar procedure as in Example 7 was repeated to obtain 500 mg of (Z)-4,4-difluoro[1-[4-(2,5-dimethylpyrrol-1-yl)benzoyl-2,3,4,5-tetrahydro-1H-1-benzazepin-5-ylidene]acetic acid.

$^1$H-NMR ($\delta$ ppm in CDCl$_3$, TMS internal standard): 1.95 (6H, m), 2.24–2.84 (total 2H), 3.24 (1H, m), 5.04 (1H, m), 6.08 (2H, s), 6.25 (1H, s), 6.68–6.80 (total 2H), 7.03–7.30 (total 7H), 7.38 (1H, d), 7.57–7.67 (total 2H), 8.35 (1H, d)

MS (FAB): 555 (M$^+$)

(Example 65)

Using 960 mg of methyl (Z)-[4,4-difluoro-1-[4-[2-(1H-1,2,4-triazol-1-yl)benzoyl]amino]benzoyl-2,3,4,5-tetrahydro-1H-1-benzazepin-5-ylidene]acetate, a similar procedure as in Example 7 was repeated to obtain 767 mg of (Z)-[4,4-difluoro-1-[4-[2-(1H-1,2,4-triazol-1-yl)benzoyl]amino]benzoyl-2,3,4,5-tetrahydro-1H-1-benzazepin-5-ylidene]acetic acid.

$^1$H-NMR ($\delta$ ppm in DMSO-d$_6$, TMS internal standard): 2.44 (1H, m), 3.10 (1H, m), 4.86 (1H, m), 6.66 (1H, s), 6.82 (1H, m), 7.03 (2H, d), 7.19 (1H, t), 7.30 (1H, t), 7.34–7.46 (total 3H), 7.58–7.74 (total 4H), 8.07 (1H, s), 8.88 (1H, s), 10.47 (1H, s), 10.19 (1H, m)

MS (FAB): 530 (M$^+$+1)

(Example 66)

Using 270 mg of methyl (Z)-[4,4-difluoro-1-[4-[2-(1H-imidazol-1-yl)benzoyl]amino]benzoyl-2,3,4,5-tetrahydro-1H-1-benzazepin-5-ylidene]acetate, a similar procedure as in Example 7 was repeated to obtain 115 mg of (Z)-[4,4-difluoro-1-[4-[2-(1H-imidazol-1-yl)benzoyl]amino]benzoyl-2,3,4,5-tetrahydro-1H-1-benzazepin-5-ylidene]acetic acid.

$^1$H-NMR ($\delta$ ppm in CDCl$_3$, TMS internal standard): 2.44 (2H, m), 3.09 (1H, m), 4.86 (1H, m), 6.66 (1H, s), 6.82 (1H, m), 6.97 (1H, s), 7.04 (2H, d), 7.19 (1H, t), 7.23–7.43 (total 5H), 7.52–7.70 (total 4H), 7.78 (1H, s), 10.49 (1H, s), 13.18 (1H, br)

MS (FAB): 529 (M$^+$+1)

(Example 67)

Using 4.96 g of methyl (Z)-[4,4-difluoro-1-[4-[2-(2-ethyl-1H-imidazol-1-yl)benzoyl]amino]benzoyl-2,3,4,5-tetrahydro-1H-1-benzazepin-5-ylidene]acetate, a similar procedure as in Example 7 was repeated to obtain 4.50 g of (Z)-[4,4-difluoro-1-[4-[2-(2-ethyl-1H-imidazol-1-yl)benzoyl]amino]benzoyl-2,3,4,5-tetrahydro-1H-1-benzazepin-5-ylidene]acetic acid.

$^1$H-NMR ($\delta$ ppm in CDCl$_3$, TMS internal standard): 1.04 (3H, t), 2.41 (2H, q), 3.08 (1H, br), 4.86 (1H, br), 6.03 (1H, s), 10.42 (1H, s)

MS (FAB): 529 (M$^+$+1)

(Example 68)

Using 647 mg of methyl (Z)-[4,4-difluoro-1-[4-(2-methylphenyl)acetylamino]benzoyl-2,3,4,5-tetrahydro-1H-1-benzazepin-5-ylidene]acetate, a similar procedure as in Example 7 was repeated to obtain 517 mg of (Z)-[4,4-difluoro-1-[4-(2-methylphenyl)acetylamino]benzoyl-2,3,4,5-tetrahydro-1H-1-benzazepin-5-ylidene]acetic acid.

¹H-NMR (δ ppm in CDCl₃-DMSO-d₆, TMS internal standard): 2.32 (3H, s), 2.35–2.82 (total 2H), 3.22 (1H, m), 3.68 (2H, s), 5.02 (1H, m), 6.20 (1H, s), 6.67 (1H, m), 7.05–7.13 (total 3H), 7.14–7.26 (total 5H), 7.34–7.39 (total 3H), 8.53 (1H, s)

MS (FAB): 491 (M⁺+1)

(Example 69)

Using 660 mg of methyl (Z)-[4,4-difluoro-1-[4-(2-methoxyphenyl)acetylamino]benzoyl-2,3,4,5-tetrahydro-1H-1-benzazepin-5-ylidene]acetate, a similar procedure as in Example 7 was repeated to obtain 596 mg of (Z)-[4,4-difluoro-1-[4-(2-methoxyphenyl)acetylamino]benzoyl-2,3,4,5-tetrahydro-1H-1-benzazepin-5-ylidene]acetic acid.

¹H-NMR (δ ppm in DMSO-d₆, TMS internal standard): 2.44 (2H, m), 3.10 (1H, m), 3.60 (2H, s), 3.73 (3H, s), 4.86 (1H, m), 6.63 (1H, s), 6.80 (1H, m), 6.88 (1H, t), 6.95 (1H, d), 7.02 (1H, d), 7.12–7.50 (total 8H), 10.16 (1H, s), 13.20 (1H, br)

MS (FAB): 507 (M⁺+1)

(Example 70)

Using 830 mg of methyl (Z)-[4,4-difluoro-1-[4-(2-trifluoromethylbenzoyl)amino]benzoyl-2,3,4,5-tetrahydro-1H-1-benzazepin-5-ylidene]acetate, a similar procedure as in Example 7 was repeated to obtain 751 mg of (Z)-[4,4-difluoro-1-[4-(2-trifluoromethylbenzoyl)amino]benzoyl-2,3,4,5-tetrahydro-1H-1-benzazepin-5-ylidene]acetic acid.

¹H-NMR (δ ppm in DMSO-d₆, TMS internal standard): 2.46 (2H, m), 3.11 (1H, m), 4.89 (1H, m), 6.68 (1H, s), 6.85 (1H, m), 7.09 (2H, m), 7.20 (1H, t), 7.31 (1H, t), 7.47–7.59 (total 2H), 7.67–7.74 (total 2H), 7.78 (1H, t), 7.84 (1H, d), 10.63 (1H, s), 13.17 (1H, br)

MS (FAB): 531 (M⁺+1)

(Example 71)

Using 760 mg of methyl (Z)-[4,4-difluoro-1-[4-(1-naphthylcarbonyl)amino]benzoyl-2,3,4,5-tetrahydro-1H-1-benzazepin-5-ylidene]acetate, a similar procedure as in Example 7 was repeated to obtain 555 mg of (Z)-[4,4-difluoro-1-[4-(1-naphthylcarbonyl)amino]benzoyl-2,3,4,5-tetrahydro-1H-1-benzazepin-5-ylidene]acetic acid.

¹H-NMR (δ ppm in CDCl₃-DMSO-d₆, TMS internal standard): 2.24–2.90 (total 2H), 3.23 (1H, m), 5.04 (1H, m), 6.25 (1H, s), 6.74 (1H, m), 7.13–7.21 (total 3H), 7.25 (1H, t), 7.39 (1H, d), 7.47–7.57 (total 3H), 7.62–7.71 (total 3H), 7.89 (1H, m), 7.94 (1H, d), 8.29 (1H, m), 9.95 (1H, s)

MS (FAB): 513 (M⁺+1)

(Example 72)

Using 445 mg of methyl (Z)-[4,4-difluoro-1-[4-(1-methyl-2-pyrrolyl)carbonylamino]benzoyl-2,3,4,5-tetrahydro-1H-1-benzazepin-5-ylidene]acetate, a similar procedure as in Example 7 was repeated to obtain 332 mg of (Z)-[4,4-difluoro-1-[4-(1-methyl-2-pyrrolyl)carbonylamino]benzoyl-2,3,4,5-tetrahydro-1H-1-benzazepin-5-ylidene]acetic acid.

¹H-NMR (δ ppm in CDCl₃-DMSO-d₆, TMS internal standard): 2.35–2.82 (total 2H), 3.21 (1H, m), 3.94 (3H, s), 5.04 (1H, m), 6.10 (1H, t), 6.23 (1H, s), 6.70 (1H, m), 6.76 (1H, br), 6.87 (1H, m), 7.07–7.17 (total 3H), 7.22 (1H, t), 7.37 (2H, d), 7.50 (2H, d), 8.72 (1H, s)

MS (FAB): 466 (M⁺+1)

(Example 73)

Using 700 mg of methyl (Z)-[4,4-difluoro-1-[4-(3-methyl-2-thienyl)carbonylamino]benzoyl-2,3,4,5-tetrahydro-1H-1-benzazepin-5-ylidene]acetate, a similar procedure as in Example 7 was repeated to obtain 656 mg of (Z)-[4,4-difluoro-1-[4-(3-methyl-2-thienyl)carbonylamino]benzoyl-2,3,4,5-tetrahydro-1H-1-benzazepin-5-ylidene]acetic acid.

¹H-NMR (δ ppm in CDCl₃-DMSO-d₆, TMS internal standard): 2.25–2.89 (total 2H), 2.53 (3H, s), 3.24 (1H, m), 5.04 (1H, m), 6.23 (1H, s), 6.71 (1H, m), 6.92 (1H, d)t 7.12 (1H, t), 7.15 (2H, d), 7.23 (1H, t), 7.33 (1H, d), 7.38 (1H, d), 7.47 (2H, d), 8.40 (1H, s)

MS (FAB): 483 (M⁺+1)

(Example 74)

Using 404 mg of methyl (Z)-[4,4-difluoro-1-[4-(3-methyl-2-furyl)carbonylamino]benzoyl-2,3,4,5-tetrahydro-1H-1-benzazepin-5-ylidene]acetate, a similar procedure as in Example 7 was repeated to obtain 316 mg of (Z)-[4,4-difluoro-1-[4-(3-methyl-2-furyl)carbonylamino]benzoyl-2,3,4,5-tetrahydro-1H-1-benzazepin-5-ylidene]acetic acid.

¹H-NMR (δ ppm in CDCl₃-DMSO-d₆, TMS internal standard): 2.28–2.84 (total 2H), 2.41 (3H, s), 3.23 (1H, m), 5.06 (1H, m), 6.23 (1H, s), 6.39 (1H, s), 6.70 (1H, m), 7.07 (1H, t), 7.15 (2H, d), 7.22 (1H, t), 7.37 (2H, m), 7.49 (1H, d), 8.33 (1H, s)

MS (FAB): 467 (M⁺+1)

(Example 75)

Using 770 mg of methyl (Z)-[1-[4-(2,3-dimethoxybenzoyl)amino]benzoyl-4,4-difluoro-2,3,4,5-tetrahydro-1H-1-benzazepin-5-ylidene]acetate, a similar procedure as in Example 7 was repeated to obtain 770 mg of (Z)-[1-[4-(2,3-dimethoxybenzoyl)amino]benzoyl-4,4-difluoro-2,3,4,5-tetrahydro-1H-1-benzazepin-5-ylidene]acetic acid.

¹H-NMR (δ ppm in DMSO-d₆, TMS internal standard): 2.45 (2H, m), 3.11 (1H, m), 3.76 (3H, s), 3.84 (3H, s), 4.87 (1H, m), 6.66 (1H, s), 6.84 (1H, m), 7.03–7.23 (total 6H), 7.30 (1H, t), 7.38 (1H, d), 7.55 (2H, d), 10.31 (1H, s), 13.17 (1H, s)

MS (FAB): 523 (M⁺+1)

(Example 76)

Using 600 mg of methyl (Z)-[1-[4-(2,6-dimethoxybenzoyl)amino]benzoyl-4,4-difluoro-2,3,4,5-tetrahydro-1H-1-benzazepin-5-ylidene]acetate, a similar procedure as in Example 7 was repeated to obtain 512 mg of (Z)-[1-[4-(2,6-dimethoxybenzoyl)amino]benzoyl-4,4-difluoro-2,3,4,5-tetrahydro-1H-1-benzazepin-5-ylidene]acetic acid.

¹H-NMR (δ ppm in DMSO-d₆, TMS internal standard): 2.50 (2H, m), 3.10 (1H, m), 3.73 (6H, s), 4.89 (1H, m), 6.66 (1H, s), 6.71 (2H, d), 6.83 (1H, m), 7.04 (2H, d), 7.20 (1H, t), 7.26–7.41 (total 3H), 7.52 (2H, d), 10.30 (1H, s), 13.21 (1H, m)

MS (FAB): 523 (M⁺+1)

(Example 77)

Using 525 mg of methyl (Z)-[4,4-difluoro-1-[4-(1-phenylcyclopentylcarbonyl)amino]benzoyl-2,3,4,5-tetrahydro-1H-1-benzazepin-5-ylidene]acetate, a similar procedure as in Example 7 was repeated to obtain 459 mg of (Z)-[4,4-difluoro-1-[4-(1-phenylcyclopentylcarbonyl)amino]benzoyl-2,3,4,5-tetrahydro-1H-1-benzazepin-5-ylidene]acetic acid.

$^1$H-NMR (δ ppm in DMSO-d$_6$, TMS internal standard): 1.53–1.73 (total 4H), 1.88 (2H, m), 2.43 (2H, m), 2.60 (2H, m), 3.08 (1H, m), 4.84 (1H, m), 6.56 (1H, s), 6.77 (1H, d), 6.98 (2H, d), 7.14 (1H, t), 7.16–7.50 (total 9.23 (1H, s), 13.24 (1H, m)

MS (FAB): 531 (M$^+$+1)

(Example 78)

Using 700 mg of methyl (Z)-[4,4-difluoro-1-[4-(2-piperidinobenzoyl)amino]benzoyl-2,3,4,5-tetrahydro-1H-1-benzazepin-5-ylidene]acetate, a similar procedure as in Example 7 was repeated to obtain 403 mg of (Z)-[4,4-difluoro-1-[4-(2-piperidinobenzoyl)amino]benzoyl-2,3,4,5-tetrahydro-1H-1-benzazepin-5-ylidene]acetic acid.

$^1$H-NMR (δ ppm in CDCl$_3$, TMS internal standard): 1.64 (2H, m), 1.77 (4H, m), 2.24–2.85 (total 2H), 2.96 (4H, m), 3.25 (1H, m), 5.06 (1H, m), 6.28 (1H, s), 6.74 (1H, m), 7.11–7.34 (total 6H), 7.39 (1H, d), 7.47 (1H, t), 7.57 (2H, m), 8.22 (1H, d), 12.73 (1H, s)

MS (FAB): 546 (M$^+$+1)

(Example 79)

(Z)-[4,4-Difluoro-1-[4-(2-phenylbenzoyl)amino] benzoyl-2,3,4,5-tetrahydro-1H-1-benzazepin-5-ylidene] acetic acid (1.153 g) was dissolved in 10 ml of methylene chloride and 10 ml of acetonitrile, and 10 ml of a methylene chloride solution containing 493 mg of 1-ethyl-3-(dimethylaminopropyl)carbodiimide hydrochloride was added dropwise under ice-cooling. Next, 296 mg of N-hydroxysuccinimide was added and the mixture was stirred overnight at room temperature. Water was added to the reaction solution, and the mixture was extracted with chloroform and dried over anhydrous magnesium sulfate. After evaporation of the solvent, the resulting residue was applied to silica gel column chromatography, which was eluted with ethyl acetate-hexane (1:1, v/v) to obtain 1.27 g of active ester.

$^1$H-NMR (δ ppm in CDCl$_3$, TMS internal standard): 2.56 (2H, m), 2.88 (4H, br), 3.29 (1H, m), 4.98 (1H, m), 6.38 (1H, s), 6.69 (1H, m), 6.81–7.06 (total 5H), 7.15 (1H, 7.25–7.58 (total 10H), 7.85 (1H, m)

MS m/z (FAB): 636 (M$^+$+1)

A 835 mg portion of the thus obtained active ester was dissolved in 20 ml of tetrahydrofuran, the solution was mixed with 99 mg of sodium borohydride, and the mixture was stirred for 2 days at room temperature. Water was added to the reaction solution, and the mixture was extracted with chloroform and then dried over anhydrous magnesium sulfate. After evaporation of the solvent, the resulting residue was applied to silica gel column chromatography, which was eluted with ethyl acetate-hexane (1:1, v/v) to obtain 538 mg of (Z)-2-[1-[4-(2-biphenylcarbonylamino)benzoyl]-4,4-difluoro-2,3,4,5-tetrahydro-1H-1-benzazepin-5-ylidene] ethanol.

$^1$H-NMR (δ ppm in CDCl$_3$, TMS internal standard): 1.83 (1H, m), 2.12–2.50 (total 2H), 3.31 (1H, m), 4.60–4.80 (total 3H), 6.14 (1H, m), 6.62 (1H, m), 6.82–7.16 (total 6H), 7.20–7.58 (total 8H), 7.83 (1H, m) MS m/z (FAB): 525 (M$^+$+1)

(Example 80)

(Z)-2-[1-[4-(2-Biphenylcarbonylamino)benzoyl]-4,4-difluoro-2,3,4,5-tetrahydro-1H-1-benzazepin-5-ylidene] ethanol (215 mg) and 0.114 ml of triethylamine were dissolved in 20 ml of methylene chloride and 0.0349 ml of methanesulfonyl chloride was added dropwise under ice-cooling. Next, 30 minutes thereafter, 10 ml of N,N-dimethylformamide was added, the low boiling point solvent was evaporated, 0.455 ml of N-methylpiperazine was added and then stirred overnight at 90° C. After evaporation of the solvent, the resulting residue was mixed with 1N sodium hydroxide aqueous solution, extracted with chloroform, and then the mixture was dried over anhydrous potassium carbonate. After evaporation of the solvent, the resulting residue was applied to silica gel column chromatography, which was eluted with chloroform-methanol (95:5, v/v) to obtain 176 mg of free base. Next, this product was dissolved in methanol and converted into its hydrochloride by adding 4N hydrochloric acid ethyl acetate solution, and then the solvent was evaporated under a reduced pressure. Thereafter, the resulting residue was recrystallized from benzene-diethyl ether to obtain 143 mg of (Z)-4'-[[4,4-difluoro-5-[2-(4-methyl-1-piperazinyl) ethylidene]-2,3,4,5-tetrahydro-1H-1-benzazepin-1-yl] carbonyl]-2-phenylbenzanilide dihydrochloride.

Melting point: 159°–162° C.

$^1$H-NMR (δ ppm in DMSO-d$_6$, TMS internal standard): 2.15–2.65 (total 2H), 2.83 (3H, s), 3.10–3.95 (total 8H), 4.17 (1H, m), 4.56 (1H, m), 6.40 (1H, m), 6.82 (1H, m), 7.01 (2H, m), 7.21 (1H, m), 7.24–7.60 (total 13H), 10.34 (1H, s), 11.55 (1H, m)

MS m/z (FAB): 607 (M$^+$+1)

(Example 81)

(Z)-2-[1-[4-(2-Biphenylcarbonylamino)benzoyl]-4,4-difluoro-2,3,4,5-tetrahydro-1H-1-benzazepin-5-ylidene] ethanol (220 mg) and 0.117 ml of triethylamine were dissolved in 10 ml of methylene chloride, and 0.036 ml of methanesulfonyl chloride was added dropwise under ice-cooling. Next, 30 minutes thereafter, 10 ml of N,N-dimethylformamide was added, the low boiling point solvent was evaporated, 0.350 ml of pyrrolidine was added, and then the mixture was stirred overnight at 90° C. After evaporation of the solvent, 1N sodium hydroxide aqueous solution was added to the resulting residue, and the mixture was extracted with chloroform and then dried over anhydrous potassium carbonate. After evaporation of the solvent, the resulting residue was applied to silica gel column chromatography, which was eluted with chloroform-methanol (95:5, v/v) to obtain 158 mg of free base. Next, this product was dissolved in methanol and converted into its hydrochloride by adding 4N hydrochloric acid ethyl acetate solution, and then the solvent was evaporated under a reduced pressure. Thereafter, the resulting residue was recrystallized from acetonitrilediethyl ether to obtain 61 mg of (Z)-4'-[[4,4-difluoro-5-[2-(1-pyrrolidinyl)ethylidene]-2,3,4,5-tetrahydro-1H-1-benzazepin-1-yl]carbonyl]-2-phenylbenzanilide hydrochloride in the form of colorless amorphous solid.

$^1$H-NMR (δ ppm in DMSO-d$_6$, TMS internal standard): 1.82–2.12 (total 4H), 2.15–2.70 (2H, s), 3.05–3.75 (total 7H), 4.25–4.70 (1H, m), 6.27 (1H, m), 6.70–6.90 (1H, m), 6.97–7.60 (total 14H), 10.20–10.50 (total 2H)

MS m/z (FAB) 578 (M$^+$+1)

(Reference Example 10)

[(3-dimethylamino)propyl]triphenylphosphonium bromide (2.11 g) was suspended in 30 ml of toluene, and 9.85 ml of 0.5N potassium hexamethyldisilazide toluene solution was added dropwise, followed by 1 hour of stirring at room temperature. Next, 30 ml of a toluene-dimethoxyethane mixed solvent containing 624 mg of 1-(4-aminobenzoyl)-4,4-difluoro-2,3,4,5-tetrahydro-1H-1-benzazepin-5-one was added dropwise, followed by 10 hours of stirring. Water was added to the reaction solution, and the mixture was extracted with ethyl acetate, and the resulting organic layer was washed with water and dried over anhydrous magnesium sulfate. After evaporation of the solvent, the resulting residue was applied to silica gel column chromatography, which was eluted with chloroform-methanol (97:3, v/v) to obtain 697 mg of (E)-4'-[[5-(3-dimethylaminopropylidene)-4,4-difluoro-2,3,4,5-tetrahydro-1H-1-benzazepine.

$^1$H-NMR ($\delta$ ppm in CDCl$_3$, TMS internal standard): 1.89–2.50 (total 6H), 2.16 (3H, s), 2.24 (3H, s), 3.24 (1H, m), 3.78 (1H, m), 5.01 (1H, m), 6.34 (1H, m), 6.38 (2H, d), 6.75 (1H, d), 7.01 (2H, d), 7.09 (1H, t), 7.22 (1H, t), 7.26 (1H, d)

MS m/z (EI): 3S5 (M$^+$)

(Example 82)

Using 690 mg of (E)-1-(4-aminobenzoyl)-5-(3-dimethylaminopropylidene)-4,4-difluoro-2,3,4,5-tetrahydro-1H- 1-benzazepine and 430 mg of o-phenylbenzoic acid, 520 mg of free base was synthesized in the same manner as described in Reference Example 8. Next, 340 mg of the free base was dissolved in chloroform, the resulting solution was mixed with 4N hydrochloric acid ethyl acetate solution, and the solvent was evaporated. Then, the resulting residue was mixed with hexane to obtain 111 mg of (E)-4'-[[4,4-difluoro-5-(3-dimethylaminopropylidene)-2,3,4,5-tetrahydro-1H-1-benzazepin-1-yl]carbonyl]-2-phenylbenzanilide hydrochloride in the form of colorless amorphous solid.

$^1$H-NMR ($\delta$ ppm in CDCl$_3$, TMS internal standard): 2.29–3.28 (total 12H), 4.93 (1H, m), 6.19 (1H, m), 6.79–7.58 (total 17H), 7.78 (1H, m), 12.82 (1H, m)

MS m/z (FAB): 566 (M$^+$+1)

(Example 83)

Using 300 mg of (Z)-[4,4-difluoro-1-[4-(2-phenylbenzoyl)amino]benzoyl-2,3,4,5-tetrahydro-1H-1-benzazepin-5-ylidene]acetic acid and 79 mg of 4-piperidinopiperidine, a similar procedure as in Example 11 was repeated to obtain a hydrochloride. This was recrystallized from ethanol-ethyl acetate to obtain 212 mg of (Z)-4'-[[4,4-difluoro-5-[[(4-piperidinopiperidino)carbonyl]piperidyl)carbamoyl]methylene]-2,3,4,5-tetrahydro-1H-1-benzazepin-1-yl]carbonyl]-2-phenylbenzanilide hydrochloride in the form of colorless crystals.

Melting point: 230° C. or more

Elemental analysis data (for C$_{42}$H$_{42}$N$_4$O$_3$F$_2$.HCl.1.5H$_2$O)

|  | C % | H % | N % | Cl % | F % |
| --- | --- | --- | --- | --- | --- |
| calcd. | 67.06 | 6.16 | 7.45 | 4.17 | 5.05 |
| found | 67.14 | 6.15 | 7.41 | 4.65 | 4.84 |

$^1$H-NMR ($\delta$ ppm in DMSO-d$_6$, TMS internal standard): 1.32–1.94 (total 7H), 2.16 (2H, m), 2.41 (2H, m), 2.66 (1H, m), 2.91 (2H, m), 2.98–3.46 (total 6H), 4.03 (1H, m), 4.52 (1H, m), 4.84 (1H, m), 6.77 (1H, s), 6.81 (1H, m), 7.01 (2H, m), 7.16–7.59 (total 14H), 10.34 (1H, s), 10.53 (1H, m)

MS m/z (FAB): 689 (M$^+$+1)

(Example 84)

Using 193 mg of (Z)-[4,4-difluoro-1-[4-(2-phenylbenzoyl)amino]benzoyl-2,3,4,5-tetrahydro-1H-1-benzazepin-5-ylidene]acetic acid and 0.078 ml of 1-methyl-(4-methylamino)piperidine, a similar procedure as in Example 11 was repeated to obtain a hydrochloride. This was recrystallized from ethanol-diethyl ether to obtain 80 mg of (Z)-4'-[[4,4-difluoro-5-[[N-methyl-N-(1-methyl-4-piperidyl)carbamoyl]methylene]-2,3,4,5-tetrahydro-1H-1-benzazepin-1-yl]carbonyl]-2-phenylbenzanilide hydrochloride in the form of colorless amorphous solid.

$^1$H-NMR ($\delta$ ppm in DMSO-d$_6$, TMS internal standard): 2.65–3.54 (total 11H), 2.65 (1.2H, br), 2.74 (1.8H, br), 2.75 (1.2H, s), 2.91 (1.8H, s), 3.94 (0.4H, m), 4.49 (0.6H, m), 4.83 (1H, m), 6.77–6.90 (total 2H), 7.02 (2H, m), 7.16–7.62 (total 14H), 10.19 (0.4H, s), 10.30–10.42 (1.6H, m)

MS m/z (FAB): 648 (M$^+$+1)

(Example 85)

Using 220 mg of (Z)-[4,4-difluoro-1-[4-(2-phenylbenzoyl)amino]benzoyl-2,3,4,5-tetrahydro-1H-1-benzazepin-5-ylidene]acetic acid and 77 ml of 3-aminoquinuclidine, a similar procedure as in Example 11 was repeated to obtain a hydrochloride. This was recrystallized from ethanol-diethyl ether to obtain 108 mg of (±)-(Z)-4'-[[4,4-difluoro-5-[[N-(3-quinuclidinyl)carbamoyl]methylene]-2,3,4,5-tetrahydro-1H-1-benzazepin-1-yl]carbonyl]-2-phenylbenzanilide hydrochloride in the form of colorless amorphous solid.

$^1$H-NMR ($\delta$ ppm in DMSO-d$_6$, TMS internal standard): 1.75 (1H, m), 1.89 (1H, m), 1.98–2.15 (total 2H), 2.27–2.70 (total 2H), 2.95–3.45 (total 6H), 3.64 (1H, m), 4.18 (1H, m), 4.86 (1H, m), 6.58 (1H, s), 6.77 (1H, m), 7.01 (2H, m), 7.17 (1H, m), 7.25–7.60 (total 13H), 8.70 (1H, m), 10.12 (1H, m), 10.31 (1H, m)

MS m/z (FAB): 647 (M$^+$+1)

(Example 86)

Using 300 mg of (Z)-[4,4-difluoro-1-[4-[2-(2-methylphenyl)benzoyl]amino]benzoyl-2,3,4,5-tetrahydro-1H-1-benzazepin-5-ylidene]acetic acid, a similar procedure as in Example 11 was repeated to obtain a hydrochloride. This was recrystallized from ethanol-diethyl ether to obtain 264 mg of (Z)-4'-[[4,4-difluoro-5-[(4-dimethylaminopiperidino)carbonyl]methylene]-2,3,4,5-tetrahydro-1H-1-benzazepin-1-yl]carbonyl]-2-(2-methylphenyl)benzanilide hydrochloride in the form of colorless crystals.

Melting point: 210° C. or more $^1$H-NMR ($\delta$ ppm in DMSO-d$_6$, TMS internal standard): 1.38–1.78 (total 2H), 2.06 (3H, s), 2.10 (2H, m), 2.66 (1H, m), 2.71 (6H, s), 2.95–3.22 (total 2H), 3.43 (1H, m), 4.03 (1H, m), 4.51 (1H, m), 4.83 (1H, m), 6.78 (1H, s), 6.80 (1H, m), 6.99 (2H, m), 7.06–7.41 (total 9H), 7.43–7.62 (total 4H), 10.23 (1H, s), 10.66 (1H, m)

MS (FAB): 663 (M$^+$+1)

(Example 87)

Using 230 mg of (Z)-[4,4-difluoro-1-[4-[2-(2-methylphenyl)benzoyl]amino]benzoyl-2,3,4,5-tetrahydro-1H-1-benzazepin-5-ylidene]acetic acid and 0.083 ml of 4-dimethylaminopiperidine, a similar procedure as in Example 11 was repeated to obtain a hydrochloride. This was recrystallized from ethanol-diisopropyl ether to obtain 187 mg of (Z)-4'-[[4,4-difluoro-5-[[(4-dimethylaminopiperidino)carbonyl]methylene]-2,3,4,5-tetrahydro-1H-1-benzazepin-1-yl]carbonyl]-2-methylbenzanilide hydrochloride in the form of colorless crystals.

Melting point: 204°–206° C.
Elemental analysis data (for $C_{34}H_{36}N_4O_3F_2 \cdot HCl \cdot 2H_2O$)

|  | C % | H % | N % | Cl % | F % |
|---|---|---|---|---|---|
| calcd. | 61.95 | 6.27 | 8.50 | 5.38 | 5.76 |
| found | 61.99 | 6.34 | 8.21 | 5.40 | 5.68 |

$^1$H-NMR (δ ppm in DMSO-$d_6$, TMS internal standard): 1.40–1.80 (total 2H), 2.09 (2H, m), 2.42 (2H, m), 2.67 (1H, m), 2.71 (6H, s), 2.98–3.21 (total 2H), 4.06 (1H, d), 4.53 (1H, d), 4.89 (1H, m), 6.81 (1H, s), 6.85 (1H, d), 7.09 (2H, d), 7.20 (1H, t), 7.25–7.44 (total 5H), 7.52 (1H, d), 7.58 (2H, d), 10.39 (1H, s), 10.72 (1H, m)

MS m/z (EI): 587 ($M^+$+1)

(Example 88)

Using 230 mg of (Z)-[4,4-difluoro-1-[4-[2-(2-methylphenyl)benzoyl]amino]benzoyl-2,3,4,5-tetrahydro-1H-1-benzazepin-5-ylidene]acetic acid and 97.5 ml of 4-piperidinopiperidine, a similar procedure as in Example 11 was repeated to obtain a hydrochloride. This was recrystallized from ethanol-ethyl acetate-diethyl ether to obtain 166 mg of (Z)-4'-[[4,4-difluoro-5-[[(4-piperidinopiperidino)carbonyl]methylene]-2,3,4,5-tetrahydro-1H-1-benzazepin-1-yl]carbonyl]-2-methylbenzanilide hydrochloride in the form of colorless crystals.

Melting point: 194°–196° C.
Elemental analysis data ($C_{37}H_{40}N_4O_3F_2 \cdot HCl \cdot 1.8H_2O$)

|  | C % | H % | N % | Cl % | F % |
|---|---|---|---|---|---|
| calcd. | 63.89 | 6.46 | 8.05 | 5.10 | 5.46 |
| found | 63.82 | 6.53 | 7.87 | 5.26 | 5.37 |

$^1$H-NMR (δ ppm in DMSO-$d_6$, TMS internal standard): 1.32–1.94 (total 7H), 2.15 (2H, m), 2.34 (3H, s), 2.43 (2H, m), 2.67 (1H, m), 2.92 (2H, m), 3.02–3.49 (total 6H), 4.05 (1H, m), 4.53 (1H, m), 4.87 (1H, m), 6.80 (1H, s), 6.85 (1H, m), 7.09 (2H, m), 7.20 (1H, m), 7.25–7.34 (total 7.35 (1H, d), 7.42 (1H, d), 7.52 (1H, d), 7.58 (2H, d), 10.39 (2H, m)

MS m/z (FAB): 627 ($M^+$+1)

(Example 89)

Using 300 mg of (Z)-[4,4-difluoro-1-[4-(2-methoxybenzoyl)amino]benzoyl-2,3,4,5-tetrahydro-1H-1-benzazepin-5-ylidene]acetic acid, a similar procedure as in Example 11 was repeated to obtain a hydrochloride. This was recrystallized from ethanol-diisopropyl ether to obtain 270 mg of (Z)-4'-[[4,4-difluoro-5-[[(4-dimethylaminopiperidino)carbonyl]methylene]-2,3,4,5-tetrahydro-1H-1-benzazepin-1-yl]carbonyl]-2-methoxybenzanilide hydrochloride in the form of colorless amorphous solid.

$^1$H-NMR (δ ppm in DMSO-$d_6$, TMS internal standard): 1.42–1.78 (total 2H), 2.08 (2H, m), 2.42 (2H, m), 2.67 (1H, m), 2.72 (6H, s), 2.99–3.22 (total 2H), 3.43 (1H, m), 3.85 (3H, s), 4.04 (1H, m), 4.52 (1H, m), 4.83 (1H, m), 6.79 (1H, s), 6.83 (1H, m), 7.02–7.21 (total 5H), 7.31 (1H, t), 7.44–7.62 (total 5H), 10.19 (1H, s), 10.56 (1H, m)

MS (FAB): 603 ($M^+$+1)

(Example 90)

Using 300 mg of (Z)-[1-[4-(2-ethoxybenzoyl)amino]benzoyl-4,4-difluoro-2,3,4,5-tetrahydro-1H-1-benzazepin-5-ylidene]acetic acid, a similar procedure as in Example 11 was repeated to obtain a hydrochloride. This was recrystallized from ethanol-diethyl ether to obtain 199 mg of (Z)-4'-[[4,4-difluoro-5-[[(4-dimethylaminopiperidino)carbonyl]methylene]-2,3,4,5-tetrahydro-1H-1-benzazepin-1-yl]carbonyl]-2-ethoxybenzanilide hydrochloride in the form of colorless amorphous solid.

Melting point: 181°–186° C.
$^1$H-NMR (δ ppm in DMSO-$d_6$, TMS internal standard): 1.35 (3H, s), 1.40–1.80 (total 2H), 2.09 (2H, m), 2.47 (2H, m), 2.68 (1H, m), 2.70 (3H, s), 2.71 (3H, s), 2.95–3.54 (total 3H), 4.06 (1H, m), 4.15 (2H, q), 4.53 (1H, m), 4.86 (1H, m), 6.81 (1H, s), 6.84 (1H, m), 7.02–7.21 (total 4H), 7.31 (1H, t), 7.44–7.62 (total 4H), 10.20 (1H, s), 10.76 (1H, m)

MS (FAB): 617 ($M^+$+1)

(Example 91)

Using 300 mg of (Z)-[1-[4-(2-ethoxybenzoyl)amino]benzoyl-4,4-difluoro-2,3,4,5-tetrahydro-1H-1-benzazepin-5-ylidene]acetic acid, a similar procedure as in Example 11 was repeated to obtain a hydrochloride. This was recrystallized from ethanol-diethyl ether to obtain 157 mg of (Z)-4'-[[4,4-difluoro-5-[[N-(2-dimethylaminoethyl)carbamoyl]methylene]-2,3,4,5-tetrahydro-1H-1-benzazepin-1-yl]carbonyl]-2-ethoxybenzanilide hydrochloride in the form of colorless amorphous solid.

Melting point: 140°–144° C.
$^1$H-NMR (δ ppm in DMSO-$d_6$, TMS internal standard): 1.36 (3H, s), 2.29–2.80 (total 2H), 2.80 (6H, s), 2.97–3.24 (3H, s), 3.53 (2H, m), 4.15 (2H, q), 4.89 (1H, m), 6.56 (1H, s), 6.80 (1H, m), 7.02–7.21 (total 5H), 7.29 (1H, t), 7.37 (1H, d), 7.48 (1H, t), 7.55 (2H, d), 7.63 (1H, d), 8.69 (1H, t), 10.19 (1H, s), 10.61 (1H, m)

MS (FAB): 577 ($M^+$+1)

(Example 92)

Using 240 mg of methyl (Z)-[4,4-difluoro-1-[4-(2-isopropoxybenzoyl)amino]benzoyl-2,3,4,5-tetrahydro-1H-1-benzazepin-5-ylidene]acetate, a Similar procedure as in Example 11 was repeated to obtain a hydrochloride. This was recrystallized from ethanol-diisopropyl ether to obtain 191 mg of (Z)-4'-[[4,4-difluoro-5-[[(4-dimethylaminopiperidino)carbonyl]methylene]-2,3,4,5-tetrahydro-1H-1-benzazepin-1-yl]carbonyl]-2-isopropoxybenzanilide hydrochloride in the form of colorless amorphous solid.

$^1$H-NMR (δ ppm in DMSO-$d_6$, TMS internal standard): 1.31 (6H, d), 1.40–1.80 (total 2H), 2.08 (2H, m), 2.42 (2H, m), 2.67 (1H, m), 2.72 (6H, s), 2.99–3.22 (total 2H), 3.43 (1H, m), 3.85 (3H, s), 4.04 (1H, m), 4.53 (1H, m), 4.73 (1H, m), 4.86 (1H, m), 6.81 (1H, s), 6.84 (1H, m), 6.98–7.36 (total 5H), 7.31 (1H, m), 7.42–7.70 (total 5H), 10.19 (1H, s), 10.77 (1H, m)

MS (FAB): 631 ($M^+$+1)

(Example 93)

Using 240 mg of (Z)-[4,4-difluoro-1-[4-(2-isopropoxybenzoyl)amino]benzoyl-2,3,4,5-tetrahydro-1H-1-benzazepin-5-ylidene]acetic acid, a similar procedure as in Example 11 was repeated to obtain a hydrochloride. This was recrystallized from ethanol-diisopropyl ether to obtain 157 mg of (Z)-4'-[[4,4-difluoro-5-[[N-(2-dimethylaminoethyl)carbamoyl]methylene]-2,3,4,5-tetrahydro-1H-1-benzazepin-1-yl]carbonyl]-2- isopropoxybenzanilide hydrochloride in the form of colorless amorphous solid.

$^1$H-NMR (δ ppm in DMSO-d$_6$, TMS internal standard): 1.32 (6H, d), 2.24–2.80 (total 2H), 2.80 (3H, s), 2.81 (3H, s), 2.95–3.24 (total 3H), 3.52 (2H, m), 4.73 (1H, m), 4.91 (1H, m), 6.58 (1H, s), 6.80 (1H, m), 7.01–7.41 (total 7H), 7.42–7.58 (total 3H), 7.65 (1H, d), 8.66 (1H, t), 10.18 (1H, s), 10.36 (1H, m)

MS (FAB): 591 (M$^+$+1)

(Example 94)

Using 300 mg of (Z)-[4,4-difluoro-1-[4-(3-methoxybenzoyl)amino]benzoyl-2,3,4,5-tetrahydro-1H-1-benzazepin-5-ylidene]acetic acid and 0.134 ml of 4-dimethylaminopiperidine, a similar procedure as in Example 11 was repeated to obtain a hydrochloride. This was recrystallized from ethanol-diisopropanol-diisopropyl ether to obtain 270 mg of (Z)-4'-[[4,4-difluoro-5-[[(4-dimethylaminopiperidino)carbonyl]methylene]-2,3,4,5-tetrahydro-1H-1-benzazepin-1-yl]carbonyl]-3-methoxybenzanilide hydrochloride.

Melting point: 178°–182° C.

$^1$H-NMR (δ ppm in DMSO-d$_6$, TMS internal standard): 1.38–1.80 (total 2H), 2.10 (2H, m), 2.43 (2H, m), 2.68 (1H, m), 2.71 (6H, s), 2.98–3.23 (total 2H), 3.44 (1H, m), 3.88 (3H, s), 4.06 (1H, m), 4.53 (1H, m), 4.88 (1H, m), 6.80 (1H, s), 6.84 (1H, m), 7.06–7.24 (total 4H), 7.31 (1H, t), 7.38–7.56 (total 4H), 7.63 (2H, m), 10.33 (1H, s), 10.81 (1H, m)

MS (FAB): 603 (M$^+$+1)

(Example 95)

Using 788 mg of (Z)-[1-[4-(2-chlorobenzoyl)amino] benzoyl-4,4-difluoro-2,3,4,5-tetrahydro-1H-1-benzazepin-5-ylidene]acetic acid and 0.134 ml of 4-dimethylaminopiperidine, a similar procedure as in Example 11 was repeated to obtain a hydrochloride, which was subsequently crystallized from ethanol-diethyl ether to obtain 172 mg of (Z)-2-chloro-4'-[[4,4-difluoro-5-[[(4-dimethylaminopiperidino)carbonyl]methylene]-2,3,4,5-tetrahydro-1H-1-benzazepin-1-yl]carbonyl]benzanilide hydrochloride.

Melting point: 181°–186° C.

$^1$H-NMR (δ ppm in DMSO-d$_6$, TMS internal standard): 1.40–1.80 (total 2H), 2.09 (2H, m), 2.43 (2H, m), 2.67 (1H, m), 2.71 (6H, s), 2.95–3.22 (total 2H), 3.43 (1H, m), 4.06 (1H, m), 4.53 (1H, m), 4.87 (1H, m), 6.82 (1H, s), 6.85 (1H, m), 7.10 (2H, m), 7.20 (1H, t), 7.31 (1H, t), 7.41–7.63 (total 7H), 10.61 (1H, m)

MS (FAB): 607, 609 (M$^+$+1)

(Example 96)

Using 300 mg of (Z)-[1-[4-(3-chlorobenzoyl)amino] benzoyl-4,4-difluoro-2,3,4,5-tetrahydro-1H-1-benzazepin-5-ylidene]acetic acid and 0.134 ml of 4-dimethylaminopiperidine, a similar procedure as in Example 11 was repeated to obtain a hydrochloride, which was subsequently crystallized from isopropanol-diethyl ether to obtain 140 mg of (Z)-3-chloro-4'-[[4,4-difluoro-5-[[(4-dimethylaminopiperidino)carbonyl]methylene]-2,3,4,5-tetrahydro-1H-1-benzazepin-1-yl]carbonyl]benzanilide hydrochloride in the form of colorless amorphous solid.

$^1$H-NMR (δ ppm in DMSO-d$_6$, TMS internal standard): 1.40–1.80 (total 2H), 2.08 (2H, m), 2.43 (2H, m), 2.67 (1H, m), 2.73 (3H, s), 2.74 (3H, s), 3.02–3.22 (total 2H), 3.44 (1H, m), 4.06 (1H, m), 4.54 (1H, m), 4.87 (1H, m), 6.80 (1H, s), 6.84 (1H, m), 7.06–7.22 (total 3H), 7.31 (1H, t), 7.48–7.69 (total 5H), 7.86 (1H, d), 7.95 (1H, s), 10.22 (1H, m), 10.43 (1H, s)

MS (FAB): 607, 609 (M$^+$+1)

(Example 97)

Using 350 mg of (Z)-4,4-difluoro-[1-[4-(2-nitrobenzoyl) amino]benzoyl-2,3,4,5-tetrahydro-1H-1-benzazepin-5-ylidene]acetic acid, a similar procedure as in Example 11 was repeated to obtain a hydrochloride, which was subsequently crystallized from ethanol-diethyl ether to obtain 188 mg of (Z)-4'-[[4,4-difluoro-5-[[(4-dimethylaminopiperidino)carbonyl]methylene]-2,3,4,5-tetrahydro-1H-1-benzazepin-1-yl]carbonyl]-2-nitrobenzanilide hydrochloride in the form of colorless amorphous solid.

$^1$H-NMR (δ ppm in DMSO-d$_6$, TMS internal standard): 1.40–1.80 (total 2H), 2.10 (2H, m), 2.43 (2H, m), 2.67 (1H, m), 2.70 (3H, s), 2.71 (3H, s), 3.02–3.24 (total 2H), 3.40 (1H, m), 4.05 (2H, m), 4.53 (1H, m), 4.88 (1H, m), 6.83 (1H, s), 6.86 (1H, m), 7.11 (2H, m), 7.22 (1H, m), 7.32 (1H, t), 7.52 (2H, m), 7.74–7.78 (total 2H), 7.86 (1H, t), 8.14 (1H, dd), 10.76 (1H, m), 10.80 (1H, s)

MS (FAB): 618 (M$^+$+1)

(Example 98)

Using 340 mg of (Z)-[1-[4-(2-aminobenzoyl)amino] benzoyl-4,4-difluoro-2,3,4,5-tetrahydro-1H-1-benzazepin-5-ylidene]acetic acid, a similar procedure as in Example 11 was repeated to obtain 372 mg of (Z)-2-amino-4'-[[4,4-difluoro-5-[[(4-dimethylaminopiperidino)carbonyl] methylene]-2,3,4,5-tetrahydro-1H-1-benzazepin-1-yl] carbonyl]benzanilide.

$^1$H-NMR (δ ppm in DMSO-d$_6$, TMS internal standard): 1.39–1.57 (total 2H), 1.86 (2H, m), 2.29 (6H, s), 2.10–2.80 (total 4H), 3.00–3.42 (total 2H), 3.97 (1H, m), 5.01 (1H, m), 5.47 (1H, s), 6.32 (1H, s), 6.66–6.77 (total 3H), 7.06–7.70 (total 5H), 7.35–7.50 (total 4H), 8.01 (1H, m)

MS (FAB): 588 (M$^+$+1)

(Example 99)

Using 380 mg of (Z)-[4,4-difluoro-1-[4-(2-(2,5-dimethylpyrrol-1-yl)benzoyl]amino]benzoyl-2,3,4,5-tetrahydro-1H-1-benzazepin-5-ylidene]acetic acid, a similar procedure as in Example 11 was repeated to obtain 309 mg of (Z)-4'-[[4,4-difluoro-5-[[(4-dimethylaminopiperidino) carbonyl]methylene]-2,3,4,5-tetrahydro-1H-1-benzazepin-1-yl]carbonyl]-2-(2,5-dimethylpyrrol-1-yl)benzanilide.

$^1$H-NMR (δ ppm in CDCl$_3$, TMS internal standard): 1.42–1.59 (total 2H), 1.91 (2H, m), 2.18–2.80 (total 2H), 2.29 (6H, s), 2.39 (1H, m), 2.74 (1H, m), 3.97 (1H, m), 4.62 (1H, m), 6.08 (1H, s), 6.34 (1H, s), 6.70 (2H, m), 7.06–7.18 (total 4H), 7.22 (1H, t), 7.38 (1H, d), 7.55–7.66 (total 2H), 8.35 (1H, dd)

MS (FAB): 666 (M$^+$+1)

(Example 100)

Using 300 mg of (Z)-[4,4-difluoro-1-[4-[2-(1H-1,2,4-triazol-1-yl)benzoyl]amino]benzoyl-2,3,4,5-tetrahydro-1H-1-benzazepin-5-ylidene]acetic acid and 0.156 ml of 4-dimethylaminopiperidine, a similar procedure as in Example 11 was repeated to obtain a hydrochloride, which was subsequently crystallized from ethanol-diethyl ether to obtain 243 mg of (Z)-4'-[[4,4-difluoro-5-[[(4-dimethylaminopiperidino)carbonyl]methylene]-2,3,4,5-tetrahydro-1H-1-benzazepin-1-yl]carbonyl]-2-(1H-1,2,4-triazol-1-yl)benzanilide hydrochloride.

Melting point: 190°–193° C.

$^1$H-NMR (δ ppm in DMSO-d$_6$, TMS internal standard): 1.38–1.80 (total 2H), 2.09 (2H, m), 2.42 (2H, m), 2.67 (1H, m), 2.70 (3H, s), 2.71 (3H, s), 2.96–3.21 (total 2H), 3.44 (1H, m), 4.04 (1H, m), 4.52 (1H, m), 4.86 (1H, m), 6.75 (1H, s), 6.S3 (1H, m), 7.05 (2H, m), 7.20 (1H, t), 7.29 (1H, t), 7.42 (2H, m), 7.51 (1H, d), 7.59–7.74 (total 4H), 8.07 (1H, s), 8.90 (1H, s), 10.51 (1H, s), 10.81 (1H, m)

MS (FAB): 640 (M$^+$+1)

(Example 101)

Using 300 mg of (Z)-[4,4-difluoro-1-[4-[2-(1H-1,2,4-triazol-1-yl)benzoyl]amino]benzoyl-2,3,4,5-tetrahydro-1H-1-benzazepin-5-ylidene]acetic acid and 115 mg of methylamine hydrochloride, the reaction of Example 11 was repeated and the product was crystallized from ethanol-diethyl ether to obtain 190 mg of (Z)-4'-[[4,4-difluoro-5-(N-methylcarbamoylmethylene)-2,3,4,5-tetrahydro-1H-1-benzazepin-1-yl]carbonyl]-2-(1H-1,2,4-triazol-1-yl)benzanilide.

Melting point: 210° C. or more $^1$H-NMR (δ ppm in CDCl$_3$, TMS internal standard): 2.41 (1H, m), 2.94 and 2.95 (total 3H, each s), 2.96 (1H, m), 3.23 (1H, m), 4.96 (1H, m), 6.36 (1H, s), 6.57 (1H, d), 6.70 (2H, m), 7.00–7.16 (total 4H), 7.22–7.32 (total 2H), 7.35–7.70 (total 4H), 8.02 (1H, s), 8.31 (1H, s), 9.78 (1H, m)

MS (FAB): 543 (M$^+$+1)

(Example 102)

Using 100 mg of (Z)-[4,4-difluoro-1-[4-[2-(1H-imidazol-1-yl)benzoyl]amino]benzoyl-2,3,4,5-tetrahydro-1H-1-benzazepin-5-ylidene]acetic acid and 56 mg of isopropylamine, a similar procedure as in Example 11 was repeated to obtain 233 mg of (Z)-4'-[[4,4-difluoro-5-(N-isopropylcarbamoylmethylene)-2,3,4,5-tetrahydro-1H-1-benzazepin-1-yl]carbonyl]-2-(1H-imidazol-1-yl)benzanilide.

$^1$H-NMR (δ ppm in CDCl$_3$, TMS internal standard): 1.22 (6H, d), 2.15–2.70 (total 2H), 3.29 (1H, m), 4.17 (1H, m), 4.80 (1H, m), 6.01 (1H, m), 6.30 (1H, s), 6.66 (1H, m), 7.00–7.38 (total 10H), 7.40–7.62 (total 7.69 (1H, s), 7.79 (1H, d)

MS (FAB): 570 (M$^+$+1)

(Example 103)

Using 1.0 g of (Z)-[1-[4-[2-(2-ethyl-1H-imidazol-1-yl)benzoylamino]benzoyl]-4,4-difluoro-2,3,4,5-tetrahydro-1H-1-benzazepin-5-ylidene]acetic acid and 5 ml of aqueous ammonia, a similar procedure as in Example 11 was repeated to obtain 683 mg of (Z)-4'-[(5-carbamoylmethylene-4,4-difluoro-2,3,4,5-tetrahydro-1H-1-benzazepin-1-yl]carbonyl]-2-(2-ethyl-1H-imidazol-1-yl)benzanilide.

Melting point: 290° C. or more

Elemental analysis data (C$_{31}$H$_{27}$N$_5$O$_3$F$_2$·0.3H$_2$O)

|  | C % | H % | N % | F % |
| --- | --- | --- | --- | --- |
| calcd. | 66.37 | 4.96 | 12.48 | 6.77 |
| found | 66.35 | 4.97 | 12.53 | 6.70 |

$^1$H-NMR (δ ppm in DMSO-d$_6$, TMS internal standard): 1.04 (3H, t), 2.40 (2H, q), 3.06 (1H, br), 4.87 (1H, br), 6.48 (1H, s), 10.39 (1H, d)

MS (FAB): 556 (M$^+$+1)

(Example 104)

Using 0.5 g of (Z)-[1-[4-[2-(2-ethyl-1H-imidazol-1-yl)benzoylamino]benzoyl]-4,4-difluoro-2,3,4,5-tetrahydro-1H-1-benzazepin-5-ylidene]acetic acid and 40% methylamine aqueous solution, a similar procedure as in Example 11 was repeated to obtain 425 mg of (Z)-2-(2-ethyl-1H-imidazol-1-yl)-4'-[[4,4-difluoro-5-[(N-methylcarbamoyl)methylene]-2,3,4,5-tetrahydro-1H-1-benzazepin-1-yl]carbonyl]benzanilide.

Melting point: 290° C. or more

Elemental analysis data (C$_{32}$H$_{29}$N$_5$O$_3$F$_2$)

|  | C % | H % | N % | F % |
| --- | --- | --- | --- | --- |
| calcd. | 67.48 | 5.13 | 12.30 | 6.67 |
| found | 67.19 | 5.30 | 12.32 | 6.61 |

(Example 105)

Using 0.5 g of (Z)-[1-[4-[2-(2-ethyl-1H-imidazol-1-yl)benzoylamino]benzoyl]-4,4-difluoro-2,3,4,5-tetrahydro-1H-1-benzazepin-5-ylidene]acetic acid and 0.074 ml of cylopropylamine, a similar procedure as in Example 11 was repeated to obtain 325 mg of (Z)-4'-[[5-[(N-cyclopropylcarbamoyl)methylene]-4,4-difluoro-2,3,4,5-tetrahydro-1H-1-benzazepin-1-yl]carbonyl]-2-(2-ethyl-1H-imidazol-1-yl) benzanilide.

Melting point: 260° C. or more

Elemental analysis data (C$_{34}$H$_{31}$N$_5$O$_3$F$_2$)

|  | C % | H % | N % | F % |
| --- | --- | --- | --- | --- |
| calcd. | 68.56 | 5.25 | 11.76 | 6.38 |
| found | 68.48 | 5.35 | 11.80 | 6.35 |

$^1$H-NMR (δ ppm in DMSO-d$_6$, TMS internal standard): 0.46 (2H, m), 0.67 (2H, m), 1.04 (3H, t), 2.40 (2H, q), 3.04 (1H, br), 4.87 (1H, br), 6.48 (1H, s), 8.35 (1H, d), 10.38 (1H, s)

MS (FAB): 570 (M$^+$+1)

(Example 106)

Using 280 mg of (Z)-[4,4-difluoro-1-[4-(2-methylphenyl)acetylamino]benzoyl-2,3,4,5-tetrahydro-1H-1-benzazepin-5-ylidene]acetic acid and 0.152 ml of 4-dimethylaminopiperidine, a similar procedure as in Example 11 was repeated to obtain a hydrochloride, which was subsequently crystallized from ethanol-diethyl ether to obtain 173 mg of (Z)-N-[4'-[[4,4-difluoro-5-[[(4-dimethylaminopiperidino)carbonyl]methylene]-2,3,4,5-tetrahydro-1H-1-benzazepin-1-yl]carbonyl]phenyl-2-methoxyphenylacetamide hydrochloride.

Melting point: 186°–191° C.

¹H-NMR (δ ppm in DMSO-d₆, TMS internal standard): 1.39–1.77 (total 2H), 2.07 (2H, m), 2.26 (3H, s), 2.41 (1H, m), 2.66 (1H, m), 2.70 (3H, s), 2.72 (3H, s), 2.97–3.21 (total 2H), 3.42 (1H, m), 3.66 (2H, s), 4.04 (1H, m), 4.52 (1H, m), 4.87 (1H, m), 6.76 (1H, s), 6.80 (1H, s), 7.04 (2H, m), 7.08–7.25 (total 5H), 7.28 (1H, t), 7.44 (2H, m), 7.50 (1H, m), 10.33 (1H, s), 10.48 (1H, m)

MS (FAB): 601 (M⁺+1)

(Example 107)

Using 280 mg of (Z)-[4,4-difluoro-1-[4-(2-methoxyphenyl)acetylamino]benzoyl-2,3,4,5-tetrahydro-1H-1-benzazepin-5-ylidene]acetic acid and 0.152 ml of 4-dimethylaminopiperidine, a similar procedure as in Example 11 was repeated to obtain a hydrochloride, which was subsequently crystallized from ethanol-diethyl ether to obtain 230 mg of (Z)-4'-[[4,4-difluoro-5-[[(4-dimethylaminopiperidino)carbonyl]methylene]-2,3,4,5-tetrahydro-1H-1-benzazepin-1-yl]carbonyl]-3-methylpyrrole-2-carboxyamide hydrochloride.

Melting point: 183°–188° C.

¹H-NMR (δ ppm in DMSO-d₆, TMS internal standard): 1.40–1.80 (total 2H), 2.09 (2H, m), 2.41 (2H, m), 2.66 (1H, m), 2.70 (6H, s), 2.98–3.21 (total 2H), 3.43 (1H, m), 3.60 (2H, s), 3.73 (3H, s), 4.05 (1H, m), 4.52 (1H, m), 4.87 (1H, m), 6.77 (1H, s), 6.81 (1H, m), 6.88 (1H, t), 6.96 (1H, d), 7.03 (2H, m), 7.13–7.32 (total 5H), 7.42–7.51 (total 3H), 10.21 (1H, s), 10.73 (1H, m)

MS (FAB): 617 (M⁺+1)

(Example 108)

Using 300 mg of (Z)-[4,4-difluoro-1-[4-(2-trifluoromethylbenzoyl)amino]benzoyl-2,3,4,5-tetrahydro-1H-1-benzazepin-5-ylidene]acetic acid and 0.124 ml of 4-dimethylaminopiperidine, a similar procedure as in Example 11 was repeated to obtain a hydrochloride, which was subsequently crystallized from isopropanol-diisopropyl ether to obtain 270 mg of (Z)-4'-[[4,4-difluoro-5-[[(4-dimethylaminopiperidino)carbonyl]methylene]-2,3,4,5-tetrahydro-1H-1-benzazepin-1-yl]carbonyl]-2-trifluoromethylbenzanilide hydrochloride in the form of colorless amorphous solid.

¹H-NMR (δ ppm in DMSO-d₆, TMS internal standard): 1.40–1.85 (total 2H), 2.10 (2H, m), 2.43 (2H, m), 2.66 (1H, m), 2.70 (6H, s), 2.95–3.22 (total 2H), 3.43 (1H, m), 4.06 (1H, m), 4.53 (1H, m), 4.88 (1H, m), 6.82 (1H, s), 6.86 (1H, m), 7.11 (2H, m), 7.21 (1H, t), 7.32 (1H, t), 7.53 (3H, m), 7.66–7.80 (total 3H), 7.83 (1H, d), 10.68 (1H, s), 10.85 (1H, m)

MS (FAB): 641 (M⁺+1)

(Example 109)

Using 260 mg of (Z)-[4,4-difluoro-1-[4-(1-naphthylcarbonyl)amino]benzoyl-2,3,4,5-tetrahydro-1H-1-benzazepin-5-ylidene]acetic acid and 0.112 ml of 4-dimethylaminopiperidine, a similar procedure as in Example 11 was repeated to obtain a hydrochloride, which was subsequently recrystallized from ethanol-ether to obtain 180 mg of (Z)-N-[4'-[[4,4-difluoro-5-[[(4-dimethylaminopiperidino)carbonyl]methylene]-2,3,4,5-tetrahydro-1H-1-benzazepin-1-yl]carbonyl]phenylnaphthalene-1-carboxyamide hydrochloride.

Melting point: 196°–201° C.

¹H-NMR (δ ppm in DMSO-d₆, TMS internal standard): 1.36–1.81 (total 2H), 2.10 (2H, m), 2.44 (2H, m), 2.68 (1H, m), 2.71 (6H, s), 3.04–3.22 (total 2H), 3.44 (1H, m), 4.07 (1H, s), 4.54 (1H, m), 4.89 (1H, m), 6.83 (1H, s), 6.88 (1H, m), 7.13 (2H, m), 7.22 (1H, t), 7.33 (1H, t), 7.50–7.76 (total 7H), 8.00–8.16 (total 3H), 10.68 (1H, s), 10.76 (1H, m)

MS (FAB): 623 (M⁺+1)

(Example 110)

Using 300 mg of (Z)-[4,4-difluoro-1-[4-(1-methylpyrrolyl)amino]benzoyl-2,3,4,5-tetrahydro-1H-1-benzazepin-5-ylidene]acetic acid and 0.142 ml of 4-dimethylaminopiperidine, a similar procedure as in Example 11 was repeated to obtain a hydrochloride, which was subsequently crystallized from ethanol-diethyl ether to obtain 233 mg of (Z)-N-[4-[[4,4-difluoro-5-[[(4-dimethylaminopiperidino)carbonyl]methylene]-2,3,4,5-tetrahydro-1H-1-benzazepin-1-yl]carbonyl]phenyl]-1-methylpyrrole-2-carboxyamide hydrochloride.

Melting point: 195°–198° C.

¹H-NMR (δ ppm in DMSO-d₆, TMS internal standard): 1.40–1.80 (total 2H), 2.42 (2H, m), 2.67 (1H, m), 2.72 (6H, s), 2.96–3.23 (total 2H), 3.43 (1H, m), 3.83 (3H, s), 4.06 (1H, m), 4.53 (1H, m), 4.87 (1H, m), 6.07 (1H, t), 6.79 (1H, s), 6.83 (1H, m), 7.00 (2H, d), 7.06 (2H, m), 7.18 (1H, t), 7.30 (1H, t), 7.51 (1H, d), 7.55 (2H, m), 9.82 (1H, s), 10.42 (1H, m)

MS (FAB): 576 (M⁺+1)

(Example 111)

Using 300 mg of (Z)-[4,4-difluoro-1-[4-2-(3-methyl-2-thienyl)amino]benzoyl-2,3,4,5-tetrahydro-1H-1-benzazepin-5 -ylidene]acetic acid and 0.137 ml of 4-dimethylaminopiperidine, a similar procedure as in Example 11 was repeated to obtain a hydrochloride, which was subsequently crystallized from ethanol-diethyl ether to obtain 237 mg of (Z)-N-[4-[[4,4-difluoro-5-[[(4-dimethylaminopiperidino)carbonyl]methylene]-2,3,4,5-tetrahydro-1H-1-benzazepin-1-yl]carbonyl]phenyl]-3-methylthiophene-2-carboxyamide hydrochloride in the form of colorless amorphous solid.

¹H-NMR (δ ppm in DMSO-d₆, TMS internal standard): 1.38–1.79 (total 2H), 2.10 (2H, m), 2.40 (3H, s), 2.42 (2H, m), 2.68 (1H, m), 2.70 (3H, s), 2.71 (3H, s), 2.98–3.23 (total 2H), 3.43 (1H, m), 4.06 (1H, m), 4.53 (1H, m), 4.87 (1H, m), 6.80 (1H, s), 6.85 (1H, m), 7.01 (1H, s), 7.08 (2H, m), 7.19 (1H, t), 7.31 (1H, t), 7.53 (3H, m), 7.66 (1H, d), 10.07 (1H, s), 10.81 (1H, m)

MS (FAB): 593 (M⁺+1)

(Example 112)

Using 250 mg of methyl (Z)-[4,4-difluoro-1-[4-(3-methyl-2-thienyl)amino]benzoyl-2,3,4,5-tetrahydro-1H-1-benzazepin-5-ylidene]acetate and 175 mg of methylamine hydrochloride, crystals precipitated during the reaction were collected by filtration and washed with water and dichloromethane to obtain 113 mg of (Z)-N-[4-[[4,4-difluoro-5-(N-methylcarbamoylmethylene)-2,3,4,5-tetrahydro-1H-1-benzazepin-1-yl]carbonyl]phenyl]-3-methylthiophene-2-carboxyamide hydrochloride.

Melting point: 277°–279° C.

¹H-NMR (δ ppm in DMSO-d₆, TMS internal standard): 2.37 (1H, m), 2.46 (3H, s), 2.66 (3H, d), 2.75 (1H, m), 3.07 (1H, m), 4.89 (1H, m), 6.48 (1H, s), 6.76 (1H, m), 7.01 (1H, d), 7.05–7.20 (total 3H), 7.27 (1H, t), 7.34 (1H, d), 7.50 (2H, d), 7.66 (1H, d), 8.24 (1H, s), 10.00 (1H, s)

MS (FAB): 496 (M$^+$+1)

(Example 113)

Using 320 mg of (Z)-[4,4-difluoro-1-[4-(3-methyl-2-furyl)amino]benzoyl-2,3,4,5-tetrahydro-1H-1-benzazepin-5-ylidene]acetic acid and 0.188 ml of 4-dimethylaminopiperidine, a similar procedure as in Example 11 was repeated to obtain a hydrochloride, which was subsequently recrystallized from ethanol to obtain 176 mg of (Z)-N-[4-[[4,4-difluoro-5-[[(4-dimethylaminopiperidino)carbonyl]methylene]-2,3,4,5-tetrahydro-1H-1-benzazepin-1-yl]carbonyl]phenyl]-3-methyl-2-furancarboxyamide hydrochloride.

Melting point: 170°–174° C.

$^1$H-NMR (δ ppm in DMSO-d$_6$, TMS internal standard): 1.42–1.82 (total 2H), 2.10 (2H, m), 2.42 (2H, m), 2.67 (1H, m), 2.70 (3H, d), 2.98–3.30 (total 2H), 3.44 (1H, m), 4.06 (1H, m), 4.53 (1H, m), 4.87 (1H, m), 6.58 (1H, d), 6.79 (1H, s), 6.84 (1H, m), 7.07 (2H, m), 7.18 (1H, t), 7.28 (1H, t), 7.52 (2H, d), 7.55 (2H, d), 7.78 (1H, d), 10.13 (1H, s), 11.00 (1S, m)

MS (FAB): 577 (M$^+$+1)

(Example 114)

Using 300 mg of (Z)-[4,4-difluoro-1-[4-(2,3-dimethoxybenzoyl)amino]benzoyl-2,3,4,5-tetrahydro-1H-1-benzazepin-5-ylidene]acetic acid and 0.158 ml of 4-dimethylaminopiperidine, a similar procedure as in Example 11 was repeated to obtain a hydrochloride, which was subsequently crystallized from isopropanol-diisopropyl ether to obtain 252 mg of (Z)-4'-[[4,4-difluoro-5-[[(4-dimethylaminopiperidino)carbonyl]methylene]-2,3,4,5-tetrahydro-1H-1-benzazepin-1-yl]carbonyl]-2,3-dimethoxyphenylbenzanilide hydrochloride in the form of colorless amorphous solid.

$^1$H-NMR (δ ppm in DMSO-d$_6$, TMS internal standard): 1.40–1.80 (total 2H), 2.09 (2H, m), 2.42 (2H, m), 2.67 (1H, m), 2.71 (3H, s), 2.73 (3H, s), 3.00–3.22 (total 2H), 3.44 (1H, m), 3.76 (3H, s), 3.84 (3H, s), 4.06 (1H, m), 4.53 (1H, m), 4.87 (1H, m), 6.81 (1H, s), 6.85 (1H, m), 7.04–7.23 (total 6H), 7.31 (1H, t), 7.51–7.60 (total 3H), 10.33 (1H, s), 10.48 (1H, m)

MS (FAB): 633 (M$^+$+1)

(Example 115)

Using 280 mg of (Z)-[4,4-difluoro-1-[4-(2,3-dimethoxybenzoyl)amino]benzoyl-2,3,4,5-tetrahydro-1H-1-benzazepin-5-ylidene]acetic acid and 181 mg of methylamine hydrochloride, a similar procedure as in Example 11 was repeated and the thus formed product was crystallized from ethanol to obtain 215 mg of (Z)-4'-[[4,4-difluoro-5-(N-methylcarbamoylmethylene)-2,3,4,5-tetrahydro-1H-1-benzazepin-1-yl]carbonyl]-2,3-dimethoxyphenylbenzanilide.

Melting point: 242°–243° C.

$^1$H-NMR (δ ppm in DMSO-d$_6$, TMS internal standard): 2.36 (1H, m), 2.66 (3H, d), 3.06 (1H, m), 3.76 (3H, s), 3.84 (3H, s), 4.90 (1H, m), 6.50 (1H, s), 6.78 (1H, m), 7.03–7.21 (total 6H), 7.27 (1H, t), 7.35 (1H, d), 7.54 (2H, d), 8.25 (1H, m), 10.30 (1H, s)

MS (FAB): 536 (M$^+$+1)

(Example 116)

Using 250 mg of (Z)-[4,4-difluoro-1-[4-(2,6-dimethoxybenzoyl)amino]benzoyl-2,3,4,5-tetrahydro-1H-1-benzazepin-5-ylidene]acetic acid and 0.131 ml of 4-dimethylaminopiperidine, a similar procedure as in Example 11 was repeated to obtain a hydrochloride. This was crystallized from ethanol-diisopropyl ether to obtain 181 mg of (Z)-4'-[[4,4-difluoro-5-[[(4-dimethylaminopiperidino)carbonyl]methylene]-2,3,4,5-tetrahydro-1H-1-benzazepin-1-yl]carbonyl]-2,6-dimethoxyphenylbenzanilide hydrochloride in the form of colorless amorphous solid.

$^1$H-NMR (δ ppm in DMSO-d$_6$, TMS internal standard): 1.40–1.80 (total 2H), 2.10 (2H, m), 2.42 (2H, m), 2.68 (1H, m), 2.70 (3H, s), 2.71 (3H, s), 2.95–3.23 (total 2H), 3.45 (1H, m), 3.73 (6H, s), 4.05 (1H, m), 4.53 (1H, m), 4.87 (1H, m), 6.71 (2H, d), 6.80 (1H, s), 6.84 (1H, m), 7.06 (1H, m), 7.21 (1H, m), 7.36–7.38 (total 2H), 7.53 (3H, m), 10.31 (1H, s), 10.83 (1H, m)

MS (FAB): 633 (M$^+$+1)

(Example 117)

Using 280 mg of (Z)-[4,4-difluoro-1-[4-(1-phenylcyclopentylcarbonyl)amino]benzoyl-2,3,4,5-tetrahydro-1H-1-benzazepin-5-ylidene]acetic acid and 0.145 ml of 4-dimethylaminopiperidine, a similar procedure as in Example 11 was repeated to obtain a hydrochloride, which was crystallized from ethanol-diethyl ether to obtain 280 mg of (Z)-N-[4-[[4,4-difluoro-5-[[(4-dimethylaminopiperidino)carbonyl]methylene]-2,3,4,5-tetrahydro-1H-1-benzazepin-1-yl]carbonyl]phenyl-1-phenylcyclopentanecarboxyamide hydrochloride.

Melting point: 210° C. or more $^1$H-NMR (δ ppm in DMSO-d$_6$, TMS internal standard): 1.40–1.74 (total 6H), 1.88 (2H, m), 2.09 (2H, m), 2.39 (1H,m), 2.59 (2H, m), 2.66 (1H, m), 2.70 (6H, s), 2.99–3.23 (total 2H), 3.42 (1H, m), 4.02 (1H, m), 4.52 (1H, m), 4.83 (1H, m), 6.74 (1H, s), 6.79 (1H, m), 7.00 (2H, m), 7.12–7.46 (total 9H), 7.49 (1H, d), 9.25 (1H, s), 10.76 (1H, m)

MS (FAB): 641 (M$^+$+1)

(Example 118)

Using 318 mg of (Z)-[4,4-difluoro-1-[4-(1-phenylcyclopentylcarbonyl)amino]benzoyl-2,3,4,5-tetrahydro-1H-1-benzazepin-5-ylidene]acetic acid and 202 mg of methylamine hydrochloride, a similar procedure as in Example 11 was repeated and the thus formed product was crystallized from ethanol-diethyl ether to obtain 145 mg of (Z)-N-[4-[[4,4-difluoro-5-(N-methylcarbamoylmethylene)-2,3,4,5-tetrahydro-1H-1-benzazepin-1-yl]carbonyl]phenyl-1-phenylcyclopentanecarboxyamide.

Melting point: 228°–230° C.

$^1$H-NMR (δ ppm in DMSO-d$_6$, TMS internal standard): 1.50–1.70 (total 4H), 1.89 (2H, m), 2.33 (1H, m), 2.56 (2H,m), 2.65 (3H, d), 2.70 (1H, m), 3.04 (1H, m), 4.87 (1H, m), 6.44 (1H, s), 6.71 (1H, m), 7.01 (2H, m), 7.10 (1H, t), 7.20–7.45 (total 9H), 8.22 (1H, m), 9.18 (1H, s)

MS (FAB): 536 (M$^+$+1)

(Example 119)

Using 300 mg of (Z)-[4,4-difluoro-1-[4-(2-piperidinobenzoyl)amino]benzoyl-2,3,4,5-tetrahydro-1H-1-benzazepin-5-ylidene]acetic acid and 106 mg of 4-dimethylaminopiperidine, a similar procedure as in Example 11 was repeated to obtain a hydrochloride, isopropanol-diethyl ether to obtain 250 mg of (Z)-4'-[[4,4-difluoro-5-[(4-dimethylaminopiperidino)carbonyl]

methylene]-2,3,4,5-tetrahydro-1H-1-benzazepin-1-yl]carbonyl]-3-methylpyrrole-2-carboxyamide hydrochloride.

Melting point: 175°–180° C.

$^1$H-NMR (δ ppm in DMSO-d$_6$, TMS internal standard): 1.40–1.80 (total 8H), 2.12 (2H, m), 2.43 (2H, m), 2.65 (1H, m), 2.69 (6H, br), 2.85–3.33 (total 6H), 3.45 (1H, m), 4.07 (1H, m), 4.53 (1H, m), 4.88 (1H, m), 6.82 (1H, s), 6.85 (1H, m), 7.07–7.20 (total 3H), 7.24–7.41 (total 2H), 7.44–7.75 (total 5H), 7.90 (1H, m), 11.10 (1H, m), 11.53 (1H, m)

MS (FAB): 656 (M$^+$)

(Example 120)

Using 240 mg of (Z)-[4,4-difluoro-1-[4-(2,6-dimethylpyrrol-1-yl)benzoyl]-2,3,4,5-tetrahydro-1H-1-benzazepin-5-ylidene]acetic acid and 128 mg of isopropylamine, a similar procedure as in Example 11 was repeated to obtain 184 mg of (Z)-4'-[[4,4-difluoro-5-(N-isopropylcarbamoyl)carbonylmethylene-2,3,4,5-tetrahydro-1H-1-benzazepin-1-yl]carbonyl]-2-(2,5-dimethylpyrrol-1-yl)benzanilide.

Elemental analysis data (C$_{27}$H$_{23}$N$_3$O$_3$F$_2$)

|  | C % | H % | N % | F % |
| --- | --- | --- | --- | --- |
| calcd. | 65.98 | 4.72 | 8.55 | 7.73 |
| found | 65.73 | 4.74 | 8.42 | 7.73 |

$^1$H-NMR (δ ppm in CDCl$_3$, TMS internal standard): 1.24 (6H, d), 1.95 (6H, s), 2.23–2.72 (total 2H), 3.31 (1H, m), 4.21 (1H, m), 4.83 (1H, m), 5.01 (1H, m), 5.76 (1H, m), 6.08 (2H, s), 6.34 (1H, m), 6.68 (1H, m), 6.71 (1H, s), 7.04–7.19 (total 5H), 7.23 (1H, t), 7.37 (1H, d), 7.62 (2H, m), 8.34 (1H, dd)

MS (FAB): 596 (M$^+$+1)

(Example 121)

Using 539 mg of (Z)-[4,4-difluoro-1-[4-(2-phenylbenzoyl)amino]benzoyl-2,3,4,5-tetrahydro-1H-1-benzazepin-5-ylidene]acetic acid and 0.3 ml of aqueous ammonia, the reaction procedure of Example 11 was repeated. The crystals precipitated during the reaction were washed with water and diethyl ether to obtain 493 mg of (Z)-4'-[(5-carbamoylmethylene-4,4-difluoro-2,3,4,5-tetrahydro-1H-1-benzazepin-1-yl]carbonyl]-2-phenylbenzanilide.

Elemental analysis data (C$_{32}$H$_{25}$N$_3$O$_3$F$_2$.0.1H$_2$O)

|  | C % | H % | N % | F % |
| --- | --- | --- | --- | --- |
| calcd. | 71.23 | 5.04 | 7.79 | 7.04 |
| found | 71.12 | 4.92 | 7.68 | 6.89 |

$^1$H-NMR (δ ppm in CDCl$_3$, TMS internal standard): 2.37 (1H, br), 2.64 (1H, br), 3.06 (1H, br), 4.87 (1H, br), 6.46 (1H, s), 6.75 (1H, d), 7.78 (1H, s), 10.30 (1H, s)

MS m/z (FAB): 538 (M$^+$+1)

(Example 122)

Using 500 mg of (Z)-[4,4-difluoro-1-[4-(2-phenylbenzoyl)amino]benzoyl-2,3,4,5-tetrahydro-1H-1-benzazepin-5-ylidene]acetic acid and 126 mg of methylamine hydrochloride, the reaction procedure of Example 11 was repeated. The crystals precipitated during the reaction were washed with water and dichloromethane to obtain 228 mg of (Z)-4'-[[4,4-difluoro-5-(N-methylcarbamoylmethylene)-2,3,4,5-tetrahydro-1H-1-benzazepin-1-yl]carbonyl]-2-phenylbenzanilide.

Melting point: 265°–268° C.

$^1$H-NMR (δ ppm in DMSO-d$_6$, TMS internal standard): 2.37 (1H, m), 2.66 (3H, d), 2.72 (1H, m), 3.06 (1H, m), 4.87 (1H, m), 5.76 (1H, s), 6.47 (1H, s), 6.75 (1H, m), 7.02 (2H, m), 7.14 (1H, t), 7.23–7.60 (total 13H), 8.22 (1H, m), 10.29 (1H, s)

MS m/z (FAB): 552 (M$^+$+1)

(Example 123)

Using 500 mg of (Z)-[4,4-difluoro-1-[4-(2-phenylbenzoyl)amino]benzoyl-2,3,4,5-tetrahydro-1H-1-benzazepin-5-ylidene]acetic acid and 151 mg of ethylamine hydrochloride, the reaction procedure of Example 11 was repeated. The thus formed compound was crystallized from ethanol to obtain 421 mg of (Z)-4'-[[5-(N-ethylcarbamoylmethylene)-4,4-difluoro-2,3,4,5-tetrahydro-1H-1-benzazepin-1-yl]carbonyl]-2-phenylbenzanilide.

Melting point: 264°–266° C.

Elemental analysis data (C$_{34}$H$_{29}$N$_3$O$_3$F$_2$.0.6H$_2$O)

|  | C % | H % | N % | F % |
| --- | --- | --- | --- | --- |
| calcd. | 70.85 | 5.28 | 7.29 | 6.59 |
| found | 70.76 | 5.20 | 7.26 | 6.49 |

$^1$H-NMR (δ ppm in DMSO-d$_6$, TMS internal standard): 1.06 (3H, t), 2.35 (1H, m), 2.67 (1H, m), 3.15 (2H, m), 4.88 (1H, m), 6.47 (1H, s), 6.74 (1H, m), 7.02 (2H, m), 7.14 (1H, t), 7.24–7.58 (total 13H), 8.27 (1H, m), 10.28 (1H, s)

MS m/z (FAB): 566 (M$^+$+1)

(Example 124)

Using 500 mg of (Z)-[4,4-difluoro-1-[4-(2-phenylbenzoyl)amino]benzoyl-2,3,4,5-tetrahydro-1H-1-benzazepin-5-ylidene]acetic acid and 110 mg of propylamine, the reaction procedure of Example 11 was repeated. The thus formed compound was crystallized from chloroform-hexane to obtain 400 mg of (Z)-4'-[[4,4-difluoro-5-(N-propylcarbamoylmethylene)-2,3,4,5-tetrahydro-1H-1-benzazepin-1-yl]carbonyl]-2-phenylbenzanilide.

Melting point: 255°–257° C.

$^1$H-NMR (δ ppm in DMSO-d$_6$, TMS internal standard): 0.87 (3H, t), 1.42 (2H, m), 2.36 (1H, m), 2.67 (1H, m), 3.09 (3H, m), 4.88 (1H, m), 6.48 (1H, s), 6.74 (1H, m), 7.02 (2H, m), 7.14 (1H, t), 7.25–7.59 (total 13H), 8.29 (1H, m), 10.29 (1H, s)

MS m/z (FAB): 580 (M$^+$+1)

(Example 125)

Using 400 mg of (Z)-[4,4-difluoro-1-[4-(2-phenylbenzoyl)amino]benzoyl-2,3,4,5-tetrahydro-1H-1-benzazepin-5-ylidene]acetic acid and 66 mg of isopropylamine, the reaction procedure of Example 11 was repeated. The thus formed compound was crystallized from chloroform-diethyl ether to obtain 374 mg of (Z)-4'-[[4,4-difluoro-5-(N-isopropylcarbamoylmethylene)-2,3,4,5-tetrahydro-1H-1-benzazepin-1-yl]carbonyl]-2-phenylbenzanilide.

Melting point: 236°–238° C.

¹H-NMR (δ ppm in DMSO-$d_6$, TMS internal standard): 1.11 (6H, d), 2.36 (1H, m), 2.64 (1H, m), 3.94 (1H, m), 4.88 (1H, m), 6.46 (1H, s), 6.74 (1H, m), 7.02 (2H, m), 7.13 (1H, t), 7.24–7.40 (total 8H), 7.42–7.58 (total 4H), 8.12 (1H, d), 10.28 (1H, s)

MS m/z (FAB): 580 (M⁺+1)

(Example 126)

Using 539 mg of (Z)-[4,4-difluoro-1-[4-(2-phenylbenzoyl)amino]benzoyl-2,3,4,5-tetrahydro-1H-1-benzazepin-5-ylidene]acetic acid and 0.08 ml of cyclopropylamine, the reaction procedure of Example 11 was repeated. The crystals precipitated during the reaction were washed with water and dichloromethane to obtain 456 mg of (Z)-4'-[[5-(N-cyclopropylcarbamoyl)methylene]-4,4-difluoro-2,3,4,5-tetrahydro-1H-1-benzazepin-1-yl]carbonyl]-2-phenylbenzanilide.

Melting point: 246°–249° C.

Elemental analysis data ($C_{35}H_{29}N_3O_3F_2$)

|  | C % | H % | N % | F % |
| --- | --- | --- | --- | --- |
| calcd. | 72.78 | 5.06 | 7.27 | 6.58 |
| found | 72.51 | 5.33 | 7.33 | 6.39 |

¹H-NMR (δ ppm in CDCl₃, TMS internal standard): 0.46 (2H, m), 0.65 (2H, m), 2.34 (1H, br), 3.04 (1H, br), 4.87 (1H, br), 6.45 (1H, s), 6.73 (1H, d), 7.10 (2H, d), 8.35 (1H, d), 10.29 (1H, s)

MS m/z (FAB): 578 (M⁺+1)

(Example 127)

Using 539 mg Of (Z)-[4,4-difluoro-1-[4-(2-phenylbenzoyl)amino]benzoyl-2,3,4,5-tetrahydro-1H-1-benzazepin-5-ylidene]acetic acid and 0.13 ml of benzylamine, the reaction procedure of Example 11 was repeated. The crystals precipitated during the reaction were washed with water and dichloromethane to obtain 506 mg of (Z)-4'-[[4,4-difluoro-5-[(N-benzylcarbamoyl)methylene]-2,3,4,5-tetrahydro-1H-1-benzazepin-1-yl]carbonyl]-2-phenylbenzanilide.

Melting point: 189°–192° C.

Elemental analysis data ($C_{39}H_{31}N_3O_3F_2 \cdot 0.25H_2O$)

|  | C % | H % | N % | F % |
| --- | --- | --- | --- | --- |
| calcd. | 74.03 | 5.73 | 6.64 | 6.01 |
| found | 74.03 | 5.41 | 6.38 | 5.65 |

¹H-NMR (δ ppm in CDCl₃, TMS internal standard): 2.38 (1H, br), 2.67 (1H, br), 3.05 (1H, br), 4.37 (2H, d), 4.88 (1H, br), 6.57 (1H, br), 6.73 (1H, d), 7.02 (2H, d), 7.14 (1H, t), 8.82 (1H, t), 10.28 (1H, s)

MS m/z (FAB): 628 (M⁺+1)

(Example 128)

Using 400 mg of (Z)-[4,4-difluoro-1-[4-(2-phenylbenzoyl)amino]benzoyl-2,3,4,5-tetrahydro-1H-1-benzazepin-5-ylidene]acetic acid and 148 mg of cyclohexylamine, the reaction procedure of Example 11 was repeated. The thus formed compound was crystallized from methanol to obtain 280 mg of (Z)-4'-[[5-(N-cyclohexylcarbamoylmethylene)-4,4-difluoro-2,3,4,5-tetrahydro-1H-1-benzazepin-1-yl]carbonyl]-2-phenylbenzanilide.

Melting point: 262°–264° C.

Elemental analysis data ($C_{38}H_{35}N_3O_3F_2$)

|  | C % | H % | N % | F % |
| --- | --- | --- | --- | --- |
| calcd. | 73.65 | 5.69 | 6.78 | 6.13 |
| found | 73.50 | 5.72 | 6.75 | 6.01 |

¹H-NMR (δ ppm in CDCl₃, TMS internal standard): 1.07–1.60 (total 6H), 1.73 (2H, m), 2.94–3.60 (total 5H), 4.85 (1H, m), 6.76 (1H, s), 6.80 (1H, m), 7.01 (2H, m), 7.17 (1H, t), 7.24–7.58 (total 13H), 10.31 (1H, s)

MS m/z (FAB): 619 (M⁺+1)

(Example 129)

Using 500 mg of (Z)-[4,4-difluoro-1-[4-(2-phenylbenzoyl)amino]benzoyl-2,3,4,5-tetrahydro-1H-1-benzazepin-5-ylidene]acetic acid and 151 mg of dimethylamine hydrochloride, the reaction procedure of Example 11 was repeated. The thus formed compound was crystallized from ethanol-diethyl ether to obtain 411 mg of (Z)-4'-[[5-(N,N-dimethylcarbamoylmethylene)-4,4-difluoro-2,3,4,5-tetrahydro1H-1-benzazepin-1-yl]carbonyl]-2-phenylbenzanilide.

Melting point: 202°–203° C.

Elemental analysis data ($C_{34}H_{29}N_3O_3F_2$)

|  | C % | H % | N % | F % |
| --- | --- | --- | --- | --- |
| calcd. | 72.20 | 5.17 | 7.43 | 6.72 |
| found | 72.18 | 5.17 | 7.47 | 6.63 |

¹H-NMR (δ ppm in CDCl₃, TMS internal standard): 2.25–2.79 (total 2H), 3.06 (3H, s), 3.09 (3H, s), 3.22 (1H, m), 4.96 (1H, m), 6.31 (1H, s), 6.66 (1H, m), 6.83–6.95 (total 3H), 7.02–7.11 (total 3H), 7.23 (1H, t), 7.32–7.50 (total 8H), 7.56 (1H, t), 7.84 (1H, d)

MS m/z (FAB): 566 (M⁺+1)

(Example 130)

Using 500 mg of (Z)-[4,4-difluoro-1-[4-(2-phenylbenzoyl)amino]benzoyl-2,3,4,5-tetrahydro-1H-1-benzazepin-5-ylidene]acetic acid and 136 mg of diethylamine, the reaction procedure of Example 11 was repeated. The thus formed compound was crystallized from diethyl ether to obtain 412 mg of (Z)-4'-[[5-(N,N-diethylcarbamoylmethylene)-4,4-difluoro-2,3,4,5-tetrahydro-1H-1-benzazepin-1-yl]carbonyl]-2-phenylbenzanilide.

Melting point: 175°–176° C.

¹H-NMR (δ ppm in CDCl₃, TMS internal standard): 1.18 (3H, t), 1.20 (3H, t), 2.27–2.80 (total 2H), 3.23 (1H, m), 3.46 (4H, m), 4.98 (1H, m), 6.33 (1H, s), 6.65 (1H, m), 6.93 (3H, m), 6.98–7.02 (total 3H), 7.22 (1H, t), 7.32–7.48 (total 8H), 7.55 (1H, t), 7.83 (1H, d)

MS m/z (FAB): 594 (M⁺+1)

(Example 131)

Using 400 mg of (Z)-[4,4-difluoro-1-[4-(2-phenylbenzoyl)amino]benzoyl-2,3,4,5-tetrahydro-1H-1- benzazepin-5-ylidene]acetic acid and 79 mg of pyrrolidine, the reaction procedure of Example 11 was repeated. The thus formed compound was crystallized from dichloromethane-diethyl ether-hexane to obtain 292 mg of (Z)-4'-[[4,4-difluoro-5-[(1-pyrrolidinylcarbonyl)methylene-4,4-difluoro-2,3,4,5-tetrahydro-1H-1-benzazepin-1-yl]carbonyl]-2-phenylbenzanilide in the form of colorless amorphous solid.

Melting point: 132°–136° C.

$^1$H-NMR ($\delta$ ppm in CDCl$_3$, TMS internal standard): 1.60–2.03 (total 4H), 2.25–2.80 (total 2H), 3.20 (1H, m), 3.43–3.60 (total 4H), 4.99 (1H, m), 6.31 (1H, s), 6.65 (1H, m), 6.93 (3H, m), 6.98–7.12 (total 3H), 7.22 (1H, t), 7.31–7.47 (total 8H), 7.52 (1H, t), 7.84 (1H, d)

MS m/z (FAB): 592 (M$^+$+1)

(Example 132)

Using 400 mg of (Z)-[4,4-difluoro-1-[4-(2-phenylbenzoyl)amino]benzoyl-2,3,4,5-tetrahydro-1H-1-benzazepin-5-ylidene]acetic acid and 127 mg of piperidine, the reaction procedure of Example 11 was repeated. The thus formed compound was crystallized from chloroform-diethyl ether-hexane to obtain 289 mg of (Z)-4'-[(4,4-difluoro-5-piperidinocarbonylmethylene-4,4-difluoro-2,3,4,5-tetrahydro-1H-1-benzazepin-1-yl)carbonyl]-2-phenylbenzanilide in the form of colorless amorphous solid.

$^1$H-NMR ($\delta$ ppm in DMSO-d$_6$, TMS internal standard): 1.40–1.60 (total 6H), 1.73 (2H, m), 2.94–3.60 (total 5H), 4.85 (1H, m), 6.76 (1H, s), 6.80 (1H, m), 7.01 (2H, m), 7.17 (1H, t), 7.24–7.60 (total 13H), 10.31 (1H, s)

MS m/z (FAB): 605 (M$^+$)

(Example 133)

Using 400 mg of (Z)-[4,4-difluoro-1-[4-(2-phenylbenzoyl)amino]benzoyl-2,3,4,5-tetrahydro-1H-1-benzazepin-5-ylidene]acetic acid and 97 mg of morpholine, the reaction procedure of Example 11 was repeated. The thus formed compound was crystallized from isopropanol-diethyl ether to obtain 324 mg of (Z)-4'-[(4,4-difluoro-5-morpholinocarbonylmethylene-4,4-difluoro-2,3,4,5-tetrahydro-1H-1-benzazepin-1-yl)carbonyl]-2-phenylbenzanilide.

Melting point: 161°–165° C.

$^1$H-NMR ($\delta$ ppm in DMSO-d$_6$, TMS internal standard): 2.40 (2H, m), 3.07 (1H, m), 3.42–3.60 (total 8H), 4.84 (1H, m), 6.76 (1H, s), 6.80 (1H, m), 7.01 (2H, m), 7.18 (1H, t), 7.27–7.60 (total 13H), 10.32 (1H, s)

MS m/z (FAB): 608 (M$^+$+1)

(Example 134)

Using 500 mg of (Z)-[4,4-difluoro-1-[4-(2-phenylbenzoyl)amino]benzoyl-2,3,4,5-tetrahydro-1H-1-benzazepin-5-ylidene]acetic acid and 114 mg of 2-ethanolamine, the reaction procedure of Example 11 was repeated. The crystals precipitated during the reaction were collected by filtration and washed with water and dichloromethane to obtain 420 mg of (Z)-4'-[[4,4-difluoro-5-[N-(2-hydroxyethyl)carbamoylmethylene]-4,4-difluoro-2,3,4,5-tetrahydro-1H-1-benzazepin-1-yl]carbonyl]-2-phenylbenzanilide.

Melting point: 262°–265° C.

$^1$H-NMR ($\delta$ ppm in DMSO-d$_6$, TMS internal standard): 2.36 (1H, m), 2.68 (1H, m), 3.04 (1H, m), 3.22 (2H, m), 3.45 (2H, m), 4.71 (1H, m), 4.88 (1H, m), 6.47 (1H, s), 6.74 (1H, m), 7.02 (2H, m), 7.16 (1H, t), 7.21–7.60 (total 13H), 8.35 (1H, t), 10.30 (1H, s)

MS m/z (FAB): 682 (M$^+$+1)

(Example 135)

Using 500 mg of (Z)-[4,4-difluoro-1-[4-(2-phenylbenzoyl)amino]benzoyl-2,3,4,5-tetrahydro-1H-1-benzazepin-5-ylidene]acetic acid and 140 mg of 2-methoxyethylamine, the reaction procedure of Example 11 was repeated. The thus formed compound was crystallized from ethanol to obtain 420 mg of (Z)-4'-[[4,4-difluoro-5-[N-(2-methoxyethyl)carbamoylmethylene]-2,3,4,5-tetrahydro-1H-1-benzazepin-1-yl]carbonyl]-2-phenylbenzanilide.

Melting point: 230°–231° C.

$^1$H-NMR ($\delta$ ppm in DMSO-d$_6$, TMS internal standard): 2.37 (1H, m), 2.69 (1H, m), 3.03 (1H, m), 3.26 (3H, s), 3.28 (2H, m), 3.38 (2H, m), 4.89 (1H, m), 6.48 (1H, s), 6.74 (1H, m), 7.02 (1H, m), 7.13 (1H, t), 7.26–7.59 (total 13H), 8.46 (1H, t), 10.28 (1H, s)

MS m/z (FAB): 595 (M$^+$+1)

(Example 136)

Using 506 mg of (Z)-[1-[4-(2-ethoxybenzoyl)amino]benzoyl-4,4-difluoro-2,3,4,5-tetrahydro-1H-1-benzazepin-5-ylidene]acetic acid and 0.3 ml of aqueous ammonia, the reaction procedure of Example 11 was repeated. The thus formed product was crystallized from ethyl acetate-diethyl ether to obtain 100 mg of (Z)-4'-[(5-carbamoylmethylene-4,4-difluoro-2,3,4,5-tetrahydro-1H-1-benzazepin-1-yl)carbonyl]-2-ethoxybenzanilide in the form of colorless amorphous solid.

Elemental analysis data (C$_{28}$H$_{25}$N$_3$O$_4$F$_2$.0.5H$_2$O)

|  | C % | H % | N % | F % |
| --- | --- | --- | --- | --- |
| calcd. | 65.36 | 5.09 | 8.17 | 7.38 |
| found | 65.24 | 5.13 | 8.12 | 7.22 |

$^1$H-NMR ($\delta$ ppm in CDCl$_3$, TMS internal standard): 1.61 (3H, t), 2.4–2.8 (total 2H), 3.34 (1H, m), 4.23 (2H, d), 4.86 (1H, d), 5.66 (1H, s), 6.14 (1H, s), 6.35 (1H, s), 6.72 (1H, d), 6.94 (1H, d), 7.0–7.3 (total 5H), 7.38 (1H, d), 7.4–7.5 (total 3H), 8.24 (1H, d), 10.16 (1H, s)

MS m/z (FAB): 506 (M$^+$+1)

(Example 137)

Using 506 mg of (Z)-[1-[4-(2-ethoxybenzoyl)amino]benzoyl-4,4-difluoro-2,3,4,5-tetrahydro-1H-1-benzazepin-5-ylidene]acetic acid and 135 mg of methylamine hydrochloride, the reaction procedure of Example 11 was repeated. The thus formed product was crystallized from ethyl acetate-diethyl ether to obtain 360 mg of (Z)-4'-[[4,4-difluoro-5-(N-methylcarbamoylmethylene)-2,3,4,5-tetrahydro-1H-1-benzazepin-1-yl]carbonyl]-2-ethoxybenzanilide.

Melting point: 213°–215° C.

Elemental analysis data ($C_{29}H_{27}N_3O_4F_2$)

|  | C % | H % | N % | F % |
|---|---|---|---|---|
| calcd. | 67.04 | 5.24 | 8.09 | 7.31 |
| found | 66.82 | 5.33 | 8.10 | 7.16 |

$^1$H-NMR ($\delta$ ppm in CDCl$_3$, TMS internal standard): 1.60 (3H, t), 2.38 (1H, d), 2.65 (1H, d), 2.96 (3H, d), 3.31 (1H, d), 4.19 (2H, q), 4.87 (1H, d), 6.27 (1H, m), 6.35 (1H, s), 6.69 (1H, d), 6.91 (1H, d), 7.0–7.1 (total 4H), 7.23 (1H, t), 7.4–7.5 (total 4H), 8.22 (1H, d), 10.15 (1H, s)

MS m/z (FAB): 520 (M$^+$+1)

(Example 138)

Using 506 mg of (Z)-[1-[4-(2-ethoxybenzoyl)amino]benzoyl-4,4-difluoro-2,3,4,5-tetrahydro-1H-1-benzazepin-5-ylidene]acetic acid and 163 mg of ethylamine hydrochloride, the reaction procedure of Example 11 was repeated. The thus formed product was crystallized from ethyl acetate-diethyl ether to obtain 410 mg of (Z)-2-ethoxy-4'-[[5-(N-ethylcarbamoylmethylene)-4,4-difluoro-2,3,4,5-tetrahydro-1H-1-benzazepin-1-yl]carbonyl]benzanilide.

Melting point: 197°–199° C.

Elemental analysis data ($C_{30}H_{29}N_3O_4F_2 \cdot 0.1H_2O$)

|  | C % | H % | N % | F % |
|---|---|---|---|---|
| calcd. | 67.30 | 5.50 | 7.85 | 7.10 |
| found | 67.01 | 5.64 | 7.93 | 6.83 |

$^1$H-NMR ($\delta$ ppm in CDCl$_3$, TMS internal standard): 1.24 (3H, t), 1.60 (3H, t), 2.40.(1H, m), 2.70 (1H, m), 3.34 (1H, m), 3.44 (2H, q), 4.17 (2H, q), 4.88 (1H, m), 6.36 (2H, m), 6.68 (1H, d), 6.67 (1H, d), 7.0–7.1 (total 4H), 7.23 (1H, t), 7.4–7.5 (total 4H), 8.22 (1H, d), 10.14 (1H, s)

MS m/z (FAB): 534 (M$^+$+1)

(Example 139)

Using 506 mg of (Z)-[1-[4-(2-ethoxybenzoyl)amino]benzoyl-4,4-difluoro-2,3,4,5-tetrahydro-1H-1-benzazepin-5-ylidene]acetic acid and 0.10 ml of propylamine, the reaction procedure of Example 11 was repeated. The thus formed product was crystallized from ethyl acetate-diethyl ether to obtain 430 mg of (Z)-4'-[[4,4-difluoro-5-(N-propylcarbamoylmethylene)-2,3,4,5-tetrahydro-1H-1-benzazepin-1-yl]carbonyl]-2-ethoxybenzanilide.

Melting point: 214°–216° C.

Elemental analysis data ($C_{31}H_{31}N_3O_4F_2 \cdot 0.2H_2O$)

|  | C % | H % | N % | F % |
|---|---|---|---|---|
| calcd. | 67.55 | 5.74 | 7.62 | 6.89 |
| found | 67.74 | 6.13 | 7.65 | 6.65 |

$^1$H-NMR ($\delta$ ppm in CDCl$_3$, TMS internal standard): 0.98 (3H, t), 1.6–1.7 (total 5H), 2.40 (1H, m), 2.66 (1H, m), 3.3–3.4 (total 3H, m), 4.18 (2H, q), 4.88 (1H, m), 6.36 (2H, br), 6.68 (1H, d), 6.89 (1H, d), 7.0–7.1 (total 4H), 7.23 (1H, t), 7.4–7.5 (total 4H), 8.22 (1H, d), 10.15 (1H, s)

MS m/z (FAB): 548 (M$^+$+1)

(Example 140)

Using 506 mg of (Z)-[1-[4-(2-ethoxybenzoyl)amino]benzoyl-4,4-difluoro-2,3,4,5-tetrahydro-1H-1-benzazepin-5-ylidene]acetic acid and 0.10 ml of isopropylamine, the reaction procedure of Example 11 was repeated. The thus formed product was crystallized from ethyl acetate-diethyl ether to obtain 450 mg of (Z)-4'-[[4,4-difluoro-5-(N-isopropylcarbamoylmethylene)-2,3,4,5-tetrahydro-1H-1-benzazepin-1-yl]carbonyl]-2-ethoxybenzanilide.

Melting point: 230° C. or more

Elemental analysis data ($C_{31}H_{31}N_3O_4F_2 \cdot 0.1H_2O$)

|  | C % | H % | N % | F % |
|---|---|---|---|---|
| calcd. | 67.72 | 5.73 | 7.65 | 6.91 |
| found | 67.56 | 5.77 | 7.59 | 6.71 |

$^1$H-NMR ($\delta$ ppm in CDCl$_3$, TMS internal standard): 1.25 (6H, t), 1.60 (3H, t), 2.37 (1H, m), 2.67 (1H, m), 3.33 (1H, m), 4.18 (2H, q), 4.25 (1H, m), 4.88 (1H, d), 6.11 (1H, m), 6.35 (1H, s), 6.67 (1H, d), 6.89 (1H, d), 7.0–7.1 (total 4H), 7.23 (1H, t), 7.4–7.5 (total 4H), 8.22 (1H, d), 10.14 (1H, s)

MS m/z (FAB): 548 (M$^+$+1)

(Example 141)

Using 506 mg of (Z)-[1-[4-(2-ethoxybenzoyl)amino]benzoyl-4,4-difluoro-2,3,4,5-tetrahydro-1H-1-benzazepin-5-ylidene]acetic acid and 0.08 ml of cyclopropylamine, the reaction procedure of Example 11 was repeated. The thus formed product was crystallized from ethyl acetate-diethyl ether to obtain 440 mg of (Z)-4'-[[5-(N-cyclopropylcarbamoylmethylene)-4,4-difluoro-2,3,4,5-tetrahydro-1H-1-benzazepin-1-yl]carbonyl]-2-ethoxybenzanilide.

Melting point: 230° C. or more

Elemental analysis data ($C_{31}H_{29}N_3O_4F_2 \cdot 0.25H_2O$)

|  | C % | H % | N % | F % |
|---|---|---|---|---|
| calcd | 67.69 | 5.41 | 7.64 | 6.91 |
| found | 67.42 | 5.42 | 7.96 | 6.77 |

$^1$H-NMR ($\delta$ ppm in CDCl$_3$, TMS internal standard): 0.6–0.7 (total 2H), 0.8–0.9 (total 2H), 1.59 (3H, t), 2.38 (1H, d), 2.68 (1H, d), 2.85 (1H, m), 3.28 (1H, d), 4.14 (1H, q), 4.87 (1H, d), 6.33 (1H, s), 6.6–6.7 (2H, m), 6.83 (1H, d), 7.0–7.1 (total 4H), 7.22 (1H, t), 7.3–7.4 (total 4H), 8.20 (1H, d), 10.13 (1H, s)

MS m/z (FAB): 546 (M$^+$+1)

(Example 142)

Using 506 mg of (Z)-[1-[4-(2-ethoxybenzoyl)amino]benzoyl-4,4-difluoro-2,3,4,5-tetrahydro-1H-1-benzazepin-5-ylidene]acetic acid and 163 mg of dimethylamine hydrochloride, the reaction procedure of Example 11 was repeated. The thus formed product was crystallized from ethyl acetate-diethyl ether to obtain 450 mg of (Z)-4'-[[5-(N,N-dimethylcarbamoylmethylene)-4,4-difluoro-2,3,4,5-tetrahydro-1H-1-benzazepin-1-yl]carbonyl]-2-ethoxybenzanilide.

Melting point: 195°–198° C.

Elemental analysis data ($C_{30}H_{29}N_3O_4F_2 \cdot 0.5H_2O$)

|  | C % | H % | N % | F % |
|---|---|---|---|---|
| calcd. | 66.41 | 5.57 | 7.74 | 7.00 |
| found | 66.37 | 5.84 | 7.73 | 6.70 |

$^1$H-NMR (δ ppm in $CDCl_3$, TMS internal standard): 1.61 (3H, t), 2.3–2.8 (total 2H), 3.04 (3H, s), 3.09 (3H, s), 3.28 (1H, m), 4.26 (2H, q), 5.04 (1H, m), 6.34 (1H, s), 6.72 (1H, d), 6.99 (1H, d), 7.1–7.5 (total 9H), 8.25 (1s, d), 10.18 (1H, s)

MS m/z (FAB): 534 ($M^+$+1)

(Example 143)

Using 506 mg of (Z)-[1-[4-(2-ethoxybenzoyl)amino]benzoyl-4,4-difluoro-2,3,4,5-tetrahydro-1H-1-benzazepin-5-ylidene]acetic acid and 0.13 ml of diethylamine, the reaction procedure of Example 11 was repeated. The thus formed product was crystallized from ethyl acetate-diethyl ether to obtain 410 mg of (Z)-4'-[[5-(N,N-diethylcarbamoylmethylene)-4,4-difluoro-2,3,4,5-tetrahydro-1H-1-benzazepin-1-yl]carbonyl]-2-ethoxybenzanilide.

Melting point: 164°–165° C.

Elemental analysis data ($C_{32}H_{33}N_3O_4F_2 \cdot 0.5H_2O$)

|  | C % | H % | N % | F % |
|---|---|---|---|---|
| calcd. | 67.35 | 6.01 | 7.37 | 6.66 |
| found | 67.56 | 5.98 | 7.43 | 6.63 |

$^1$H-NMR (δ ppm in $CDCl_3$, TMS internal standard): 1.21 (6H, t) 1.60 (3H, t), 2.4–2.8 (total 2H), 3.30 (1H, m), 3.67 (4H, q), 4.26 (2H, q), 5.05 (1H, m), 6.38 (1H, s), 6.71 (1H, d), 6.98 (1H, d), 7.0–7.3 (total 5H), 7.36 (1H, t), 7.4–7.5 (total 3H), 8.24 (1H, d), 10.17 (1H, s)

MS m/z (FAB): 562 ($M^+$+1)

(Example 144)

Using 506 mg of (Z)-[1-[4-(2-ethoxybenzoyl)amino]benzoyl-4,4-difluoro-2,3,4,5-tetrahydro-1H-1-benzazepin-5-ylidene]acetic acid and 0.13 ml of morpholine, the reaction procedure of Example 11 was repeated. The thus formed product was crystallized from ethyl acetate-diethyl ether to obtain 470 mg of (Z)-4'-[(4,4-difluoro-5-morpholinocarbonylmethylene-2,3,4,5-tetrahydro-1H-1-benzazepin-1-yl)carbonyl]-2-ethoxybenzanilide.

Melting point: 144°–147° C.

$^1$H-NMR (δ ppm in $CDCl_3$, TMS internal standard): 1.61 (3H, t), 2.4–2.8 (total 2H), 3.30 (1H, m), 3.58 (2H, m), 3.74 (6H, m), 4.26 (2H, q), 5.05 (1H, m), 6.33 (1H, s), 6.74 (1H, d), 6.99 (1H, d), 7.1–7.6 (total 9H), 8.25 (1H, d), 10.17 (1H, s)

MS m/z (FAB): 576 ($M^+$+1)

(Example 145)

Using 400 mg of (Z)-[1-[4-(2-ethoxybenzoyl)amino]benzoyl-4,4-difluoro-2,3,4,5-tetrahydro-1H-1-benzazepin-5-ylidene]acetic acid and 163 mg of thiomorpholine, the reaction procedure of Example 11 was repeated. The thus formed product was crystallized from isopropanol to obtain 198 mg of (Z)-4'-[(4,4-difluoro-5-thiomorpholinocarbonylmethylene-2,3,4,5-tetrahydro-1H-1-benzazepin-1-yl)carbonyl]-2-ethoxybenzanilide.

$^1$H-NMR (δ ppm in $CDCl_3$, TMS internal standard): 1.61 (3H, t), 2.27–2.86 (total 6H), 3.26 (1H, m), 3.70–4.14 (total 4H), 4.26 (2H, q), 5.02 (1H, m), 6.33 (1H, s), 6.74 (1H, m), 6.99 (1H, t), 7.07–7.29 (total 6H), 7.36 (1H, m), 7.53 (3H, m), 8.24 (1H, m), 10.17 (1H, s)

MS m/z (FAB): 592 ($M^+$+1)

The following shows structures of compounds obtained in Reference Examples 6 to 10 and Examples (cf. Tables 2 and 3).

TABLE 2

| Ref. Ex. No. | Chemical Structure |
|---|---|
| 6 | [structure: benzazepine with CO$_2$Me vinyl group, two F, N-benzoyl with H$_2$N-phenyl] (Z) + |
|  | [structure: benzazepine with MeO$_2$C vinyl group, two F, N-benzoyl with H$_2$N-phenyl] (E) |
| 7 | [structure: benzazepine with CO$_2$Et vinyl group, two F, N-benzoyl with H$_2$N-phenyl] |

TABLE 2-continued

| Ref. Ex. No. | Chemical Structure |
|---|---|
| 8 | (biphenyl-2-yl)-C(=O)-NH-(4-phenyl)-C(=O)-N-[2-methylphenyl ring fused benzazepinone with CF$_2$ and C=O] |
| 9 | (4'-methylbiphenyl-2-yl)-C(=O)-NH-(4-phenyl)-C(=O)-N-[2-methylphenyl ring fused benzazepinone with CF$_2$ and C=O] |
| 10 | Me$_2$N-CH$_2$CH$_2$-CH=C[benzazepine with CF$_2$]-N-C(=O)-(4-aminophenyl) |

General structure:

$$R^7-\underset{R^6}{\underset{|}{\overset{R^5}{\overset{|}{C}}}}_n-CONH-\text{(Ar-}R^4\text{)}-C(=O)-N-\text{[benzazepine with CF}_2\text{, }R^3\text{]}-C(R^1)=C(R^2)$$

TABLE 3

| Ex. No. | R$^1$ | R$^2$ | R$^3$ | R$^4$ | R$^5$ | R$^6$ | n | R$^7$ | Salt |
|---|---|---|---|---|---|---|---|---|---|
| 1 | H | CO$_2$Me | H | H | — | — | 0 | 2-methylbiphenyl | free |
| 2 | CO$_2$Me | H | H | H | — | — | 0 | 2-methylbiphenyl | free |

TABLE 3-continued

| Ex. No. | R¹ | R² | R³ | R⁴ | R⁵ | R⁶ | n | R⁷ | Salt |
|---|---|---|---|---|---|---|---|---|---|
| 3 | H | $CO_2Me$ | H | H | — | — | 0 | 4'-Me-biphenyl-2-yl | free |
| 4 | H | $CO_2Me$ | H | H | — | — | 0 | 3'-Me-biphenyl-2-yl | free |
| 5 | H | $CO_2Me$ | H | H | — | — | 0 | biphenyl-2-yl | free |
| 6(a) | H | $CO_2Et$ | H | H | — | — | 0 | 4'-Me-biphenyl-2-yl | free |
| 6(b) | $CO_2Et$ | H | H | H | — | — | 0 | 4'-Me-biphenyl-2-yl | free |
| 7 | H | $CO_2H$ | H | H | — | — | 0 | biphenyl-2-yl | free |

TABLE 3-continued
| Ex. No. | R¹ | R² | R³ | R⁴ | R⁵ | R⁶ | n | R⁷ | Salt |
|---|---|---|---|---|---|---|---|---|---|
| 8 | CO₂H | H | H | H | — | — | 0 | 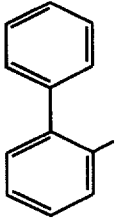 | free |
| 9 | H | CO₂H | H | H | — | — | 0 | 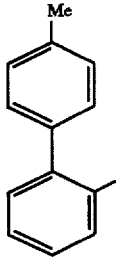 | free |
| 10 | H | CO₂H | H | H | — | — | 0 | 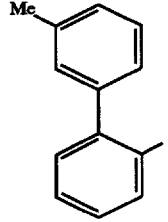 | free |
| 11 | H | 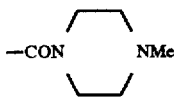 | H | H | — | — | 0 | 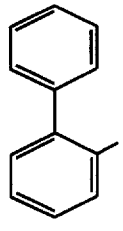 | HCl |
| 12 | H |  | H | H | — | — | 0 | 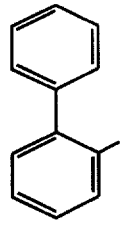 | HCl |
| 13 | H | 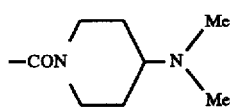 | H | H | — | — | 0 | 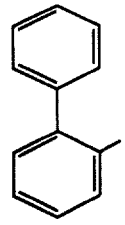 | HCl |

TABLE 3-continued
| Ex. No. | R¹ | R² | R³ | R⁴ | R⁵ | R⁶ | n | R⁷ | Salt |
|---|---|---|---|---|---|---|---|---|---|
| 14 | H | 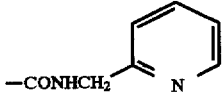 —CONHCH₂-(2-pyridyl) | H | H | — | — | 0 | 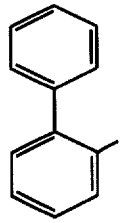 2-biphenyl | HCl |
| 15 | H | 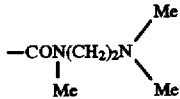 —CON(Me)(CH₂)₂NMe₂ | H | H | — | — | 0 | 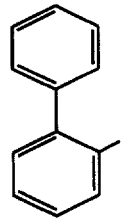 2-biphenyl | HCl |
| 16 | 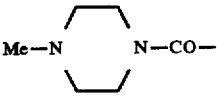 Me-N(CH₂CH₂)₂N-CO- | H | H | H | — | — | 0 | 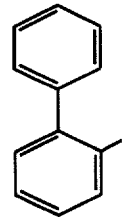 2-biphenyl | HCl |
| 17 | H |  —CON(CH₂CH₂)₂NMe | H | H | — | — | 0 | 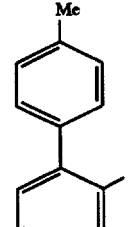 4'-Me, 2-biphenyl | HCl |
| 18 | H | 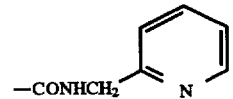 —CONHCH₂-(2-pyridyl) | H | H | — | — | 0 | 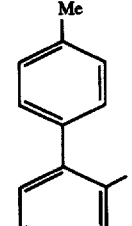 4'-Me, 2-biphenyl | HCl |
| 19 | H |  —CON(CH₂CH₂)₂NMe | H | H | — | — | 0 | 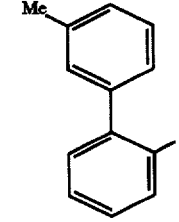 3'-Me, 2-biphenyl | HCl |

TABLE 3-continued

| Ex. No. | R¹ | R² | R³ | R⁴ | R⁵ | R⁶ | n | R⁷ | Salt |
|---|---|---|---|---|---|---|---|---|---|
| 20 | H | —CONHMe | H | H | — | — | 0 | 4'-Me-2-biphenylyl | free |
| 21 | MeNHCO— | H | H | H | — | — | 0 | 4'-Me-2-biphenylyl | free |
| 22(a) | H | CN | H | H | — | — | 0 | 4'-Me-2-biphenylyl | free |
| 22(b) (E) | CN | H | H | H | — | — | 0 | 4'-Me-2-biphenylyl | free |
| 23 | H | —CON(CH₂CH₂)₂NEt | H | H | — | — | 0 | 2-biphenylyl | HCl |
| 24 | H | —CON(CH₂CH₂CH₂)NMe | H | H | — | — | 0 | 2-biphenylyl | HCl |

TABLE 3-continued
| Ex. No. | R¹ | R² | R³ | R⁴ | R⁵ | R⁶ | n | R⁷ | Salt |
|---|---|---|---|---|---|---|---|---|---|
| 25 | H | —CONH(CH₂)₂N(Me)₂ | H | H | — | — | 0 |  2-biphenylyl | HCl |
| 26 | H | —CON(piperazine)NCH₂-phenyl | H | H | — | — | 0 | 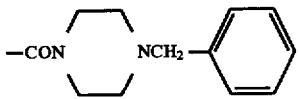 2-biphenylyl | HCl |
| 27 | H | —CONH(CH₂)₃N(Me)₂ | H | H | — | — | 0 |  2-biphenylyl | HCl |
| 28 | H | —CON(piperazine)NH | H | H | — | — | 0 | 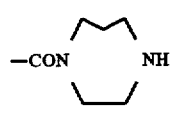 2-biphenylyl | HCl |
| 29 | H | CO₂Me | H | H | — | — | 0 | 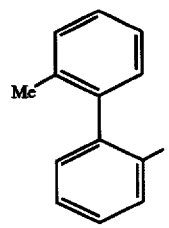 2'-Me-2-biphenylyl | free |
| 30 | H | CO₂Me | H | H | — | — | 0 | 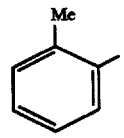 2-Me-phenyl | free |
| 31 | H | CO₂Me | H | H | — | — | 0 | 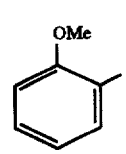 2-OMe-phenyl | free |

TABLE 3-continued

| Ex. No. | R¹ | R² | R³ | R⁴ | R⁵ | R⁶ | n | R⁷ | Salt |
|---|---|---|---|---|---|---|---|---|---|
| 32 | H | CO₂Me | H | H | — | — | 0 | 2-ethoxyphenyl | free |
| 33 | H | CO₂Me | H | H | — | — | 0 | 2-isopropoxyphenyl | free |
| 34 | H | CO₂Me | H | H | — | — | 0 | 3-methoxyphenyl | free |
| 35 | H | CO₂Me | H | H | — | — | 0 | 2-chlorophenyl | free |
| 36 | H | CO₂Me | H | H | — | — | 0 | 3-chlorophenyl | free |
| 37 | H | CO₂Me | H | H | — | — | 0 | 2-nitrophenyl | free |
| 38 | H | CO₂Me | H | H | — | — | 0 | 2-aminophenyl | free |
| 39 | H | CO₂Me | H | H | — | — | 0 | 2-(2,5-dimethylpyrrol-1-yl)phenyl | free |
| 40 | H | CO₂Me | H | H | — | — | 0 | 2-(1,2,4-triazol-1-yl)phenyl | free |
| 41 | H | CO₂Me | H | H | — | — | 0 | 2-(imidazol-1-yl)phenyl | free |

TABLE 3-continued
| Ex. No. | R¹ | R² | R³ | R⁴ | R⁵ | R⁶ | n | R⁷ | Salt |
|---|---|---|---|---|---|---|---|---|---|
| 42 | H | CO$_2$Me | H | H | — | — | 0 | 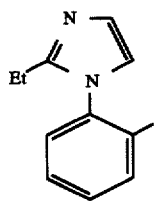 | free |
| 43 | H | CO$_2$Me | H | H | H | H | 1 | 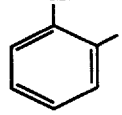 | free |
| 44 | H | CO$_2$Me | H | H | H | H | 1 | 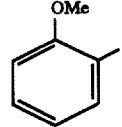 | free |
| 45 | H | CO$_2$Me | H | H | — | — | 0 | 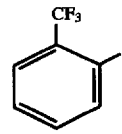 | free |
| 46 | H | CO$_2$Me | H | H | — | — | 0 | 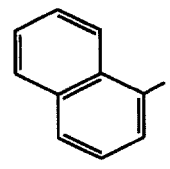 | free |
| 47 | H | CO$_2$Me | H | H | — | — | 0 | 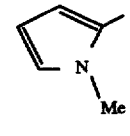 | free |
| 48 | H | CO$_2$Me | H | H | — | — | 0 | 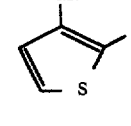 | free |
| 49 | H | CO$_2$Me | H | H | — | — | 0 | 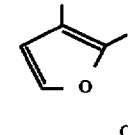 | free |
| 50 | H | CO$_2$Me | H | H | — | — | 0 | 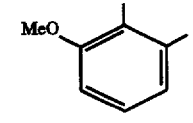 | free |
| 51 | H | CO$_2$Me | H | H | — | — | 0 | 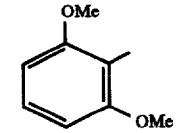 | free |

TABLE 3-continued
| Ex. No. | R¹ | R² | R³ | R⁴ | R⁵ R⁶ | n | R⁷ | Salt |
|---|---|---|---|---|---|---|---|---|
| 52 | H | CO₂Me | H | H |  | 1 | 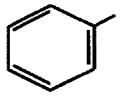 | free |
| 53 | H | CO₂Me | H | H | — — | 0 | 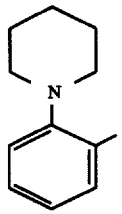 | free |
| 54 | H | CO₂H | H | H | — — | 0 | 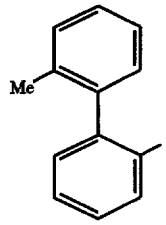 | free |
| 55 | H | CO₂H | H | H | — — | 0 | 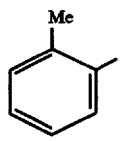 | free |
| 56 | H | CO₂H | H | H | — — | 0 | 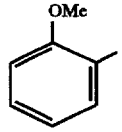 | free |
| 57 | H | CO₂H | H | H | — — | 0 | 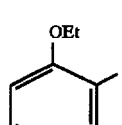 | free |
| 58 | H | CO₂H | H | H | — — | 0 | 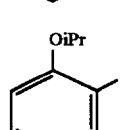 | free |
| 59 | H | CO₂H | H | H | — — | 0 | 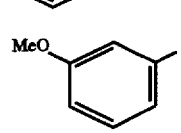 | free |
| 60 | H | CO₂H | H | H | — — | 0 | 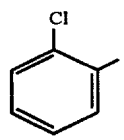 | free |
| 61 | H | CO₂H | H | H | — — | 0 | 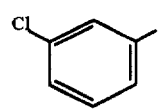 | free |

TABLE 3-continued
| Ex. No. | R¹ | R² | R³ | R⁴ | R⁵ | R⁶ | n | R⁷ | Salt |
|---|---|---|---|---|---|---|---|---|---|
| 62 | H | CO₂H | H | H | — | — | 0 | 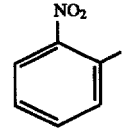 2-nitrophenyl | free |
| 63 | H | CO₂H | H | H | — | — | 0 | 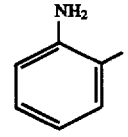 2-aminophenyl | free |
| 64 | H | CO₂H | H | H | — | — | 0 | 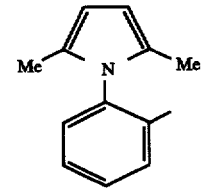 2-(2,6-dimethylpyrrol-1-yl)phenyl | free |
| 65 | H | CO₂H | H | H | — | — | 0 | 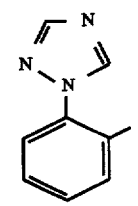 2-(1,2,4-triazol-1-yl)phenyl | free |
| 66 | H | CO₂H | H | H | — | — | 0 | 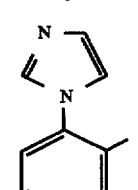 2-(imidazol-1-yl)phenyl | free |
| 67 | H | CO₂H | H | H | — | — | 0 | 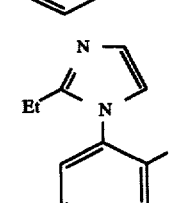 2-(2-ethylimidazol-1-yl)phenyl | free |
| 68 | H | CO₂H | H | H | H | H | 1 | 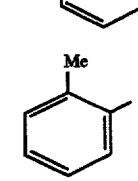 2-methylphenyl | free |
| 69 | H | CO₂H | H | H | H | H | 1 | 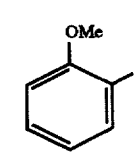 2-methoxyphenyl | free |
| 70 | H | CO₂H | H | H | — | — | 0 | 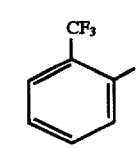 2-(trifluoromethyl)phenyl | free |

TABLE 3-continued

| Ex. No. | R¹ | R² | R³ | R⁴ | R⁵ | R⁶ | n | R⁷ | Salt |
|---|---|---|---|---|---|---|---|---|---|
| 71 | H | CO₂H | H | H | — | — | 0 | 1-naphthyl | free |
| 72 | H | CO₂H | H | H | — | — | 0 | 1-methylpyrrol-2-yl | free |
| 73 | H | CO₂H | H | H | — | — | 0 | 3-methylthiophen-2-yl | free |
| 74 | H | CO₂H | H | H | — | — | 0 | 3-methylfuran-2-yl | free |
| 75 | H | CO₂H | H | H | — | — | 0 | 2,3-dimethoxyphenyl | free |
| 76 | H | CO₂H | H | H | — | — | 0 | 2,6-dimethoxyphenyl | free |
| 77 | H | CO₂H | H | H | cyclopentyl | | 1 | phenyl | free |
| 78 | H | CO₂H | H | H | — | — | 0 | 2-(piperidin-1-yl)phenyl | free |
| 79 | H | —CH₂OH | H | H | — | — | 0 | 2-biphenylyl | free |

TABLE 3-continued

| Ex. No. | R¹ | R² | R³ | R⁴ | R⁵ | R⁶ | n | R⁷ | Salt |
|---|---|---|---|---|---|---|---|---|---|
| 80 | H | —CH₂N(piperazine)NMe | H | H | — | — | 0 | 2-biphenyl | 2HCl |
| 81 | H | —CH₂—N(pyrrolidine) | H | H | — | — | 0 | 2-biphenyl | HCl |
| 82 | Me₂N(CH₂)₂— | H | H | H | — | — | 0 | 2-biphenyl | HCl |
| 83 | H | —CON(piperidine)-N(piperidine) | H | H | — | — | 0 | 2-biphenyl | HCl |
| 84 | H | —CON(Me)-(piperidine)-NMe | H | H | — | — | 0 | 2-biphenyl | HCl |
| 85 | H | —CONH-(quinuclidine) | H | H | — | — | 0 | 2-biphenyl | HCl |

TABLE 3-continued
| Ex. No. | R¹ | R² | R³ | R⁴ | R⁵ | R⁶ | n | R⁷ | Salt |
|---|---|---|---|---|---|---|---|---|---|
| 86 | H | 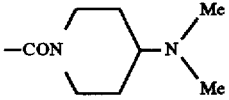 | H | H | — | — | 0 | 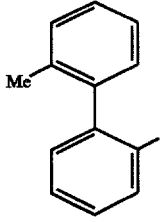 | HCl |
| 87 | H | 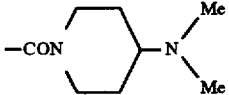 | H | H | — | — | 0 | 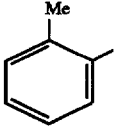 | HCl |
| 88 | H | 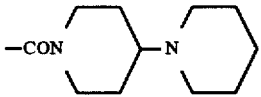 | H | H | — | — | 0 | 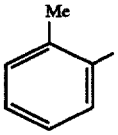 | HCl |
| 89 | H | 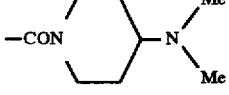 | H | H | — | — | 0 | 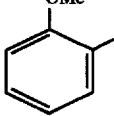 | HCl |
| 90 | H | 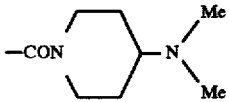 | H | H | — | — | 0 | 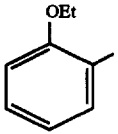 | HCl |
| 91 | H | —CONH(CH$_2$)$_2$N(Me)Me | H | H | — | — | 0 | 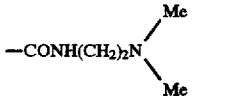 | HCl |
| 92 | H | 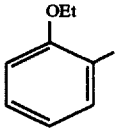 | H | H | — | — | 0 | 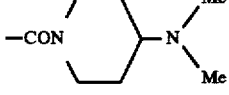 | HCl |
| 93 | H | —CONH(CH$_2$)$_2$N(Me)Me | H | H | — | — | 0 | 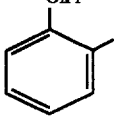 | HCl |
| 94 | H | 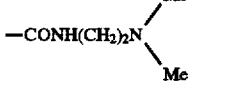 | H | H | — | — | 0 | 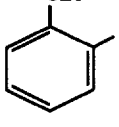 | HCl |
| 95 | H | 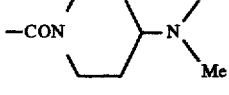 | H | H | — | — | 0 | 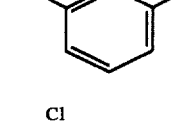 | HCl |

TABLE 3-continued
| Ex. No. | R¹ | R² | R³ | R⁴ | R⁵ | R⁶ | n | R⁷ | Salt |
|---|---|---|---|---|---|---|---|---|---|
| 96 | H | 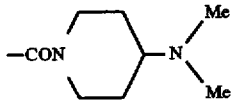 | H | H | — | — | 0 | 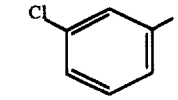 | HCl |
| 97 | H | 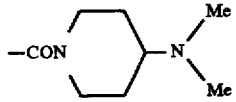 | H | H | — | — | 0 | 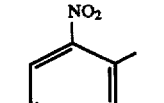 | HCl |
| 98 | H | 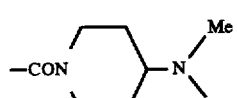 | H | H | — | — | 0 | 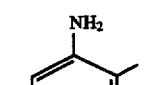 | free |
| 99 | H | 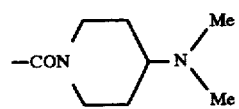 | H | H | — | — | 0 | 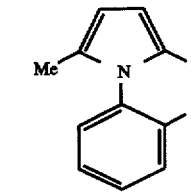 | free |
| 100 | H | 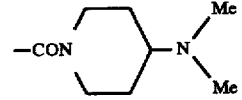 | H | H | — | — | 0 | 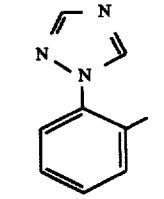 | HCl |
| 101 | H | —CONHMe | H | H | — | — | 0 | 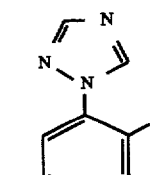 | free |
| 102 | H | —CONHiPr | H | H | — | — | 0 | 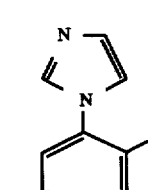 | free |
| 103 | H | —CONH₂ | H | H | — | — | 0 | 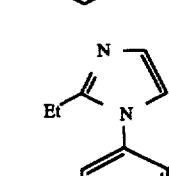 | free |

TABLE 3-continued

| Ex. No. | R¹ | R² | R³ | R⁴ | R⁵ | R⁶ | n | R⁷ | Salt |
|---|---|---|---|---|---|---|---|---|---|
| 104 | H | —CONHMe | H | H | — | — | 0 | 2-(2-ethyl-imidazol-1-yl)phenyl | free |
| 105 | H | —CONH-cyclopropyl | H | H | — | — | 0 | 2-(2-ethyl-imidazol-1-yl)phenyl | free |
| 106 | H | —CON(4-dimethylaminopiperidinyl) | H | H | H | H | 1 | 2-methylphenyl | HCl |
| 107 | H | —CON(4-dimethylaminopiperidinyl) | H | H | H | H | 1 | 2-methoxyphenyl | HCl |
| 108 | H | —CON(4-dimethylaminopiperidinyl) | H | H | — | — | 0 | 2-trifluoromethylphenyl | HCl |
| 109 | H | —CON(4-dimethylaminopiperidinyl) | H | H | — | — | 0 | 1-naphthyl | HCl |
| 110 | H | —CON(4-dimethylaminopiperidinyl) | H | H | — | — | 0 | 1-methylpyrrol-2-yl | HCl |
| 111 | H | —CON(4-dimethylaminopiperidinyl) | H | H | — | — | 0 | 3-methylthien-2-yl | HCl |
| 112 | H | —CONHMe | H | H | — | — | 0 | 3-methylfuran-2-yl | HCl |
| 113 | H | —CON(4-dimethylaminopiperidinyl) | H | H | — | — | 0 | 2,3-dimethoxyphenyl | HCl |

TABLE 3-continued

| Ex. No. | R¹ | R² | R³ | R⁴ | R⁵ | R⁶ | n | R⁷ | Salt |
|---|---|---|---|---|---|---|---|---|---|
| 114 | H | —CON(piperidin-4-yl)NMe₂ | H | H | — | — | 0 | 2,3-dimethoxyphenyl (MeO, OMe) | HCl |
| 115 | H | —CONHMe | H | H | — | — | 0 | 2,6-dimethoxyphenyl | free |
| 116 | H | —CON(piperidin-4-yl)NMe₂ | H | H | — | — | 0 | phenyl | HCl |
| 117 | H | —CON(piperidin-4-yl)NMe₂ | H | H | cyclopentyl | | 1 | phenyl | HCl |
| 118 | H | —CONHMe | H | H | cyclopentyl | | 1 | phenyl | free |
| 119 | H | —CON(piperidin-4-yl)NMe₂ | H | H | — | — | 0 | 2-(piperidin-1-yl)phenyl | HCl |
| 120 | H | —CONHiPr | H | H | — | — | 0 | 2-(2,5-dimethylpyrrol-1-yl)phenyl | free |
| 121 | H | —CONH₂ | H | H | — | — | 0 | 2-biphenyl | free |
| 122 | H | —CONHMe | H | H | — | — | 0 | 2'-phenyl-2-biphenyl | free |

TABLE 3-continued
| Ex. No. | R¹ | R² | R³ | R⁴ | R⁵ | R⁶ | n | R⁷ | Salt |
|---|---|---|---|---|---|---|---|---|---|
| 123 | H | —CONHEt | H | H | — | — | 0 | 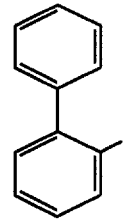 | free |
| 124 | H | —CONHPr | H | H | — | — | 0 | 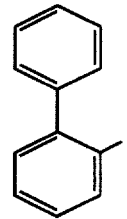 | free |
| 125 | H | —CONHiPr | H | H | — | — | 0 | 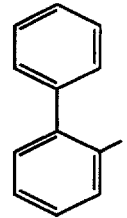 | free |
| 126 | H | —CONH—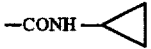 | H | H | — | — | 0 | 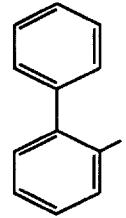 | free |
| 127 | H | —CONHCH₂—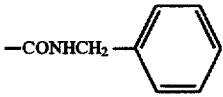 | H | H | — | — | 0 | 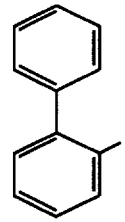 | free |
| 128 | H | —CONH—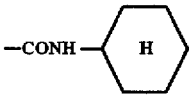 | H | H | — | — | 0 | 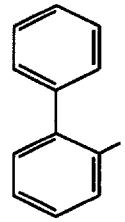 | free |

TABLE 3-continued
| Ex. No. | R¹ | R² | R³ | R⁴ | R⁵ | R⁶ | n | R⁷ | Salt |
|---|---|---|---|---|---|---|---|---|---|
| 129 | H | —CON(Me)Me | H | H | — | — | 0 | 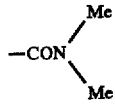 | free |
| 130 | H | —CON(Et)Et | H | H | — | — | 0 | 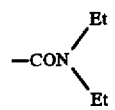 | free |
| 131 | H | —CON(pyrrolidine) | H | H | — | — | 0 | 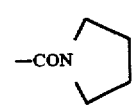 | free |
| 132 | H | —CON(piperidine) | H | H | — | — | 0 | 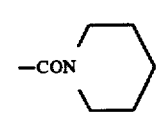 | free |
| 133 | H | —CON(morpholine) | H | H | — | — | 0 | 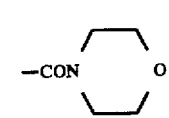 | free |
| 134 | H | —CONH(CH₂)₂OH | H | H | — | — | 0 | 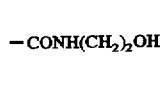 | free |

TABLE 3-continued
| Ex. No. | R¹ | R² | R³ | R⁴ | R⁵ | R⁶ | n | R⁷ | Salt |
|---|---|---|---|---|---|---|---|---|---|
| 135 | H | —CONH(CH₂)₂OMe | H | H | — | — | 0 | 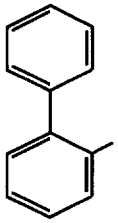 | free |
| 136 | H | —CONH₂ | H | H | — | — | 0 | 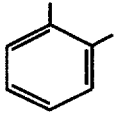 | free |
| 137 | H | —CONHMe | H | H | — | — | 0 | 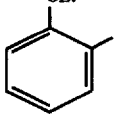 | free |
| 138 | H | —CONHEt | H | H | — | — | 0 | 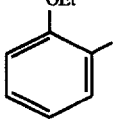 | free |
| 139 | H | —CONHPr | H | H | — | — | 0 | 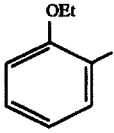 | free |
| 140 | H | —CONHiPr | H | H | — | — | 0 | 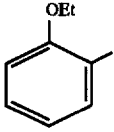 | free |
| 141 | H | 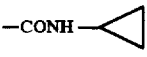 | H | H | — | — | 0 | 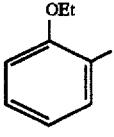 | free |
| 142 | H | 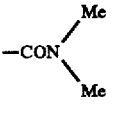 | H | H | — | — | 0 | 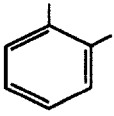 | free |
| 143 | H | 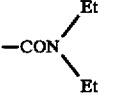 | H | H | — | — | 0 | 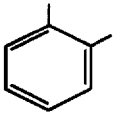 | free |
| 144 | H | 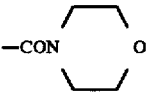 | H | H | — | — | 0 | 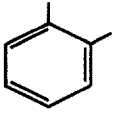 | free |

TABLE 3-continued

| Ex. No. | R¹ | R² | R³ | R⁴ | R⁵ | R⁶ | n | R⁷ | Salt |
|---|---|---|---|---|---|---|---|---|---|
| 145 | H | —CON⟨morpholine-S⟩ | H | H | — | — | 0 | (2-OEt-phenyl) | free |

In addition to the compounds of the aforementioned examples, other compounds of the present invention (Examples A-1 to 45) are shown below in the form of tables (Tables 4, 5 and 6). Since these compounds can be synthesized in accordance with the synthetic pathways and methods described in the aforementioned production processes and examples and their modifications known to those skilled in the art, particular experiments are not required.

TABLE 4

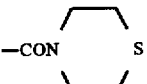

| No. | R₁ | R₂ |
|---|---|---|
| A-1 | tBu-phenyl | acetyl-piperidine-N(Me)₂ |
| A-2 | cyclopropyl-phenyl | acetyl-piperidine-N(Me)₂ |
| A-3 | iPrO-phenyl | -C(O)NH-CH₂CH₂-OMe |
| A-4 | tBuO-phenyl | acetyl-piperidine-N(Me)₂ |

TABLE 4-continued

| No. | R₁ | R₂ |
|---|---|---|
| A-5 | 2,6-di-tBu-phenoxy | -C(O)NH-CH₂CH₂-OMe |
| A-6 | 2-(2-methoxyethoxy)-phenyl | -C(O)NH-C(Me)₂ |
| A-7 | HO-phenyl | -C(O)NH-C(Me)₂ |
| A-8 | HO₂C-phenyl | -C(O)NH-C(Me)₂ |
| A-9 | 2-phenoxy-phenyl | acetyl-piperidine-N(Me)₂ |

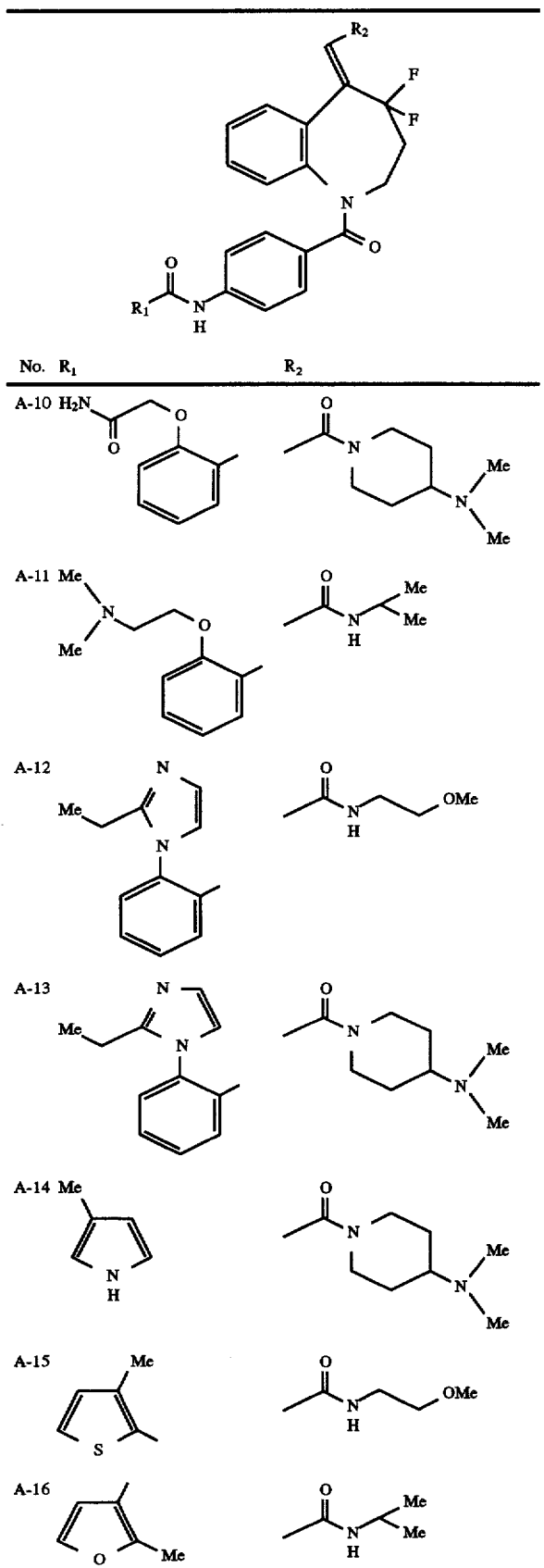
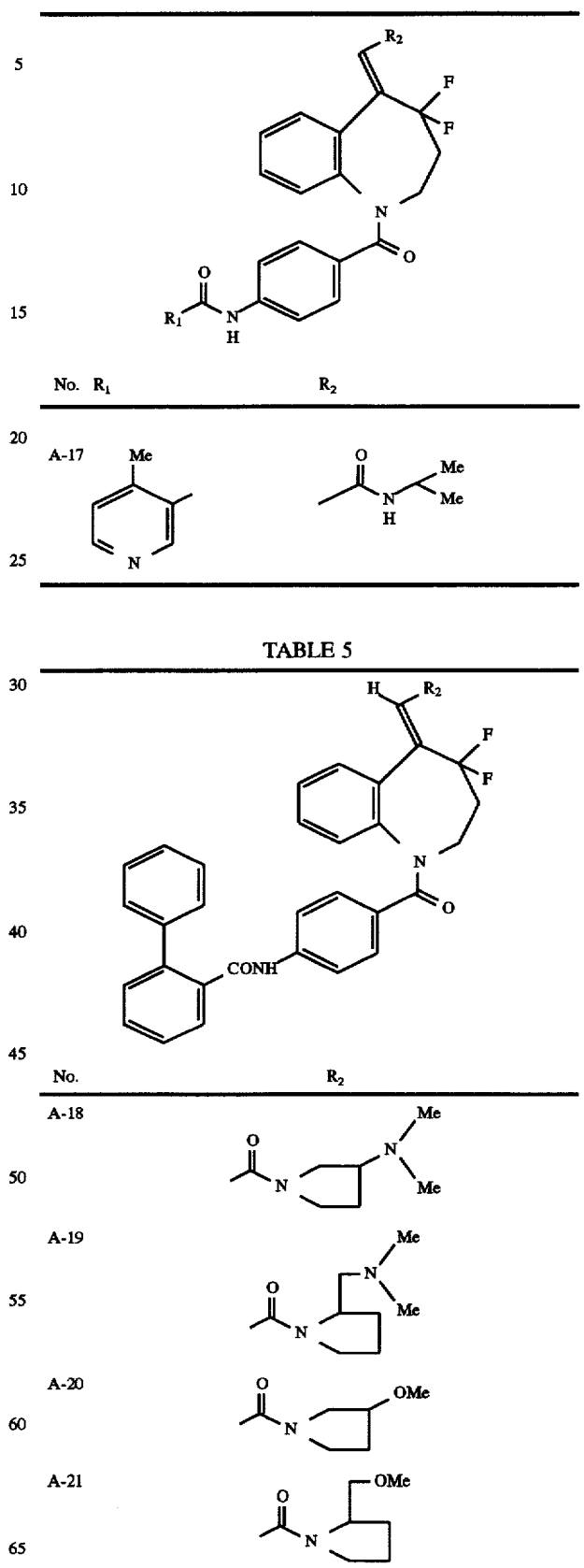

TABLE 5-continued

Structure 123 (R₂ substituent on parent scaffold with biphenyl-CONH-phenyl-CON group)

| No. | R₂ |
|---|---|
| A-22 | -C(O)NH-(quinuclidinyl) |
| A-23 | -C(O)-thiomorpholinyl |
| A-24 | -C(O)-thiomorpholinyl S-oxide |
| A-25 | -C(O)-thiomorpholinyl S,S-dioxide |
| A-26 | -C(O)-(4-(4-diethylaminopiperidin-1-yl)piperidin-1-yl) |
| A-27 | -C(O)NH-CH₂CH₂-O-CH₂CH₂-OMe |
| A-28 | -C(O)NH-CH₂-C≡C-CH₂-(pyrrolidin-1-yl) |
| A-29 | -C(O)NH-CH₂-CH=CH-CH₂-(pyrrolidin-1-yl) (cis) |
| A-30 | -C(O)-(4-(N,N-dimethylamino N-oxide)piperidin-1-yl) |
| A-31 | -C(O)-(4,4-dimethyl-piperazinium) Cl⁻ |

TABLE 5-continued

Structure 124 (R₂ substituent on parent scaffold with biphenyl-CONH-phenyl-CON group)

| No. | R₂ |
|---|---|
| A-32 | -C(O)-(4-(N,N-diethylamino)piperidin-1-yl) |
| A-33 | -Me |
| A-34 | -CH₂CH₂CH₂-N(Me)₂ |
| A-35 | -CH₂CH₂CH₂-(piperidin-1-yl) |
| A-36 | -CH₂-O-CH₂CH₂-OMe |
| A-37 | -CH=CH-Me |
| A-38 | -C(O)-(4-(2-methoxyethyl)piperazin-1-yl) |
| A-39 | -C(O)-(4-(1-methylpiperidin-4-yl)piperazin-1-yl) |
| A-40 | -C(O)-N(Me)-CH₂CH₂-(4-(1-methylpiperidin-4-yl)piperazin-1-yl) |
| A-41 | -C(O)-(4-(1'-methyl-[4,4'-bipiperidin]-1-yl)piperazin-1-yl) |
| A-42 | -C(O)-(4-(3-ethoxypropyl)piperazin-1-yl) |

TABLE 6

| No. | Structure |
|---|---|
| A-43 | 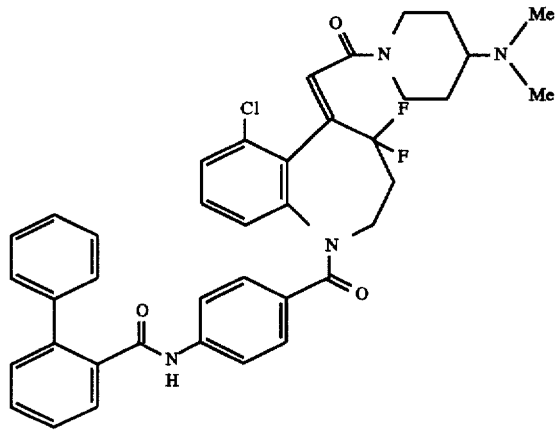 |
| A-44 | 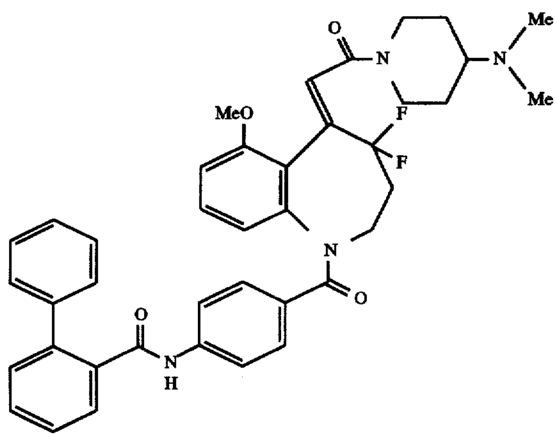 |
| A-45 | 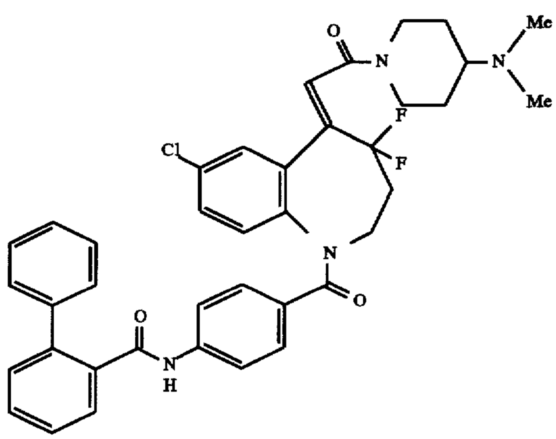 |

Formulation Examples

Injections

| Composition | | |
|---|---|---|
| Formulation 1. | Compound of the present invention | 1.5 mg |
| | Lactic acid | 0.2 mg |
| | Lactose | 200 mg |
| | Distilled water for injection use | 2.0 ml in total |
| Formulation 2. | Compound of the present invention | 1.5 mg |
| | Lactic acid | 0.2 mg |
| | Glycerol | 52 mg |
| | Distilled water for injection use | 2.0 ml in total |

About 300 ml of distilled water for injection use containing 0.75 g of the compound of the present invention and 0.1 g of lactic acid was mixed with about 500 ml of distilled water for injection use containing 100 g of lactose (or 26 g of glycerol), and the mixture was stirred. Contents in the resulting mixture was dissolved by heating the mixture at 60° C. After cooling down to room temperature, total volume of the solution was adjusted to 1,000 ml. The thus prepared solution was filtered through a membrane filter, dispensed and sealed into ampoules in 2 ml portions and then sterilized to obtain injections each ampoule containing 1.5 mg of the compound of the present invention.

Tablets

| Composition | | |
|---|---|---|
| [Tablet] | Compound of the present invention | 5.0 mg |
| | Lactose | 73.2 |
| | Corn starch | 18.8 |
| | Hydroxypropylcellulose | 3 0 |
| | Magnesium stearate | 0.5 |
| | subtotal | 100 mg |
| [Coat] | Hydroxypropyl methylcellulose 2910 | 2.5 mg |
| | Polyethylene glycol 6000 | 0.5 |
| | Talc | 0.7 |
| | Titanium oxide | 0.3 |
| | Subtotal | 4 mg |
| | Total | 104 mg |

<Production of 5 mg tablets>

The compound of the present invention (25 g) was mixed with 366 g of lactose and the mixture was pulverized using Sample Mill (manufactured by Hosokawa Micron). After uniformly mixing 391 g of the thus pulverized mixture with 91.5 g of corn starch in a fluidized granulation coating machine (manufactured by Ohgawara Seisakusyo), 150 g of 10% hydroxypropylcellulose aqueous solution was sprayed on the mixture to effect granulation. After drying, the thus prepared granules were passed through a 24-mesh screen, mixed with 2.5 g of magnesium stearate and then made into tablets, each weighing 100 mg, by a rotary tabletting machine (manufactured by Hata Tekkosho) using a die/punch system of 6.5 mm⌀×7.8 R. Using a coating apparatus (manufactured by Freund Sangyo), 154 g of an aqueous coating solution containing 12.5 g of hydroxypropylcellulose, 2.5 g of polyethylene glycol 6000, 3.5 g of talc and 1.5 g of titanium oxide was sprayed on the thus prepared tablets to obtain film-coated tablets each having 4 mg of coated film and containing 5.0 mg of the compound of the present invention.

We claim:

1. A benzazepine derivative represented by the following formula (I) or a pharmaceutically acceptable salt thereof:

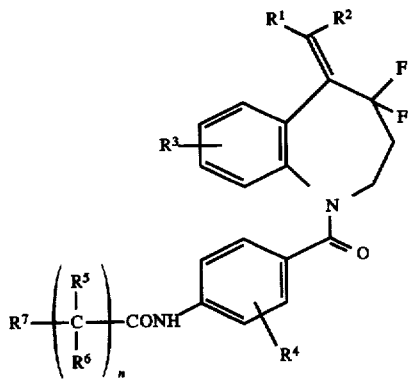

wherein the symbols in the formula have the following meanings; $R^1$ and $R^2$: one of them represents a hydrogen atom and the other represents a group represented by

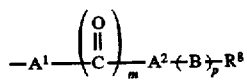

with the proviso that $R^1$ and $R^2$ cannot simultaneously be hydrogen atoms, $A^1$ and $A^2$: these may be the same or different from each other and each represents a single bond, a lower alkylene group or a lower alkenylene group, m: 0 or 1, B: a group represented by

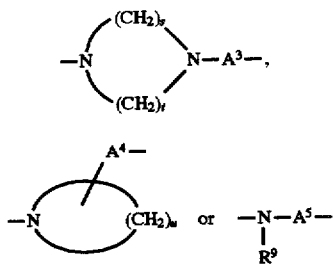

where the nitrogen atoms in these formulae may be oxidized, p: 0 or an integer of from 1 to 3, provided that when p is 2 or 3 the groups defined by B may be the same or different, $R^8$: a hydrogen atom; a lower alkyl group; a lower alkenyl group; a cycloalkyl group; a hydroxyl group; a lower alkoxy group; a carboxyl group; a lower alkoxycarbonyl group; a cyano group; an aryl group which may be substituted; a nitrogen-containing aromatic five- or six-membered heterocyclic group which may be substituted; a nitrogen-containing saturated five- to eight-membered heterocyclic group which may have a bridge and which may be substituted with a lower alkyl group on the nitrogen atom of the ring; or a group represented by

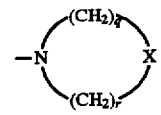

where the nitrogen atom in the formula may be oxidized, s and t: these may be the same or different from each other and each is an integer of 1 to 3, provided that the total number of s and t is an integer of from 3 to 5, u: an integer of from 2 to 7, $A^3$, $A^4$ and $A^5$: these may be the same or different from one another and each represents a single bond, a lower alkylene group or a lower alkenylene group, provided that when the adjacent group is linked to $A^3$ or $A^5$ via a nitrogen atom or an oxygen atom, $A^3$ or $A^5$ is a group other than a single bond, $R^9$: a hydrogen atom or a lower alkyl group, q and r: these may be the same or different from each other and each is an integer of from 1 to 3, provided that the total number of q and r is an integer of from 3 to 5, X: a group represented by —O— or —S(o)$_w$—, w: 0, 1 or 2, $R^3$ and $R^4$: these may be same or different from each other and each represents a hydrogen atom; a halogen atom; a lower alkyl group; a lower alkoxy group; or an amino group which may be substituted with a lower alkyl group, $R^5$ and $R^6$: these may be the same or different from each other and each represents a hydrogen atom or a lower alkyl group, where $R^5$ and $R^6$ may be combined as a lower alkylene group to form a saturated carbon ring with adjacent carbon atoms, n: 0 or 1, and $R^7$: an aryl group which may be substituted or an aromatic five- or six-membered heterocyclic group which may be substituted.

2. The compound as claimed in claim 1, or a pharmaceutically acceptable salt thereof, wherein the group represented by

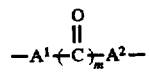

is selected from (1) a single bond, (2) a group of formula

(3) a lower alkylene group or a lower alkenylene group, or (4) a group of formula

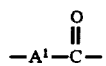

where $A^1$ is a lower alkylene group or a lower alkenylene group, and $R^8$ is a hydrogen atom; a cyano group; a carboxyl group; a lower alkoxycarbonyl group; a lower alkyl group; a lower alkenyl group; a cycloalkyl group; a hydroxyl group; a lower alkoxy group; a phenyl or naphthyl group which may be substituted with a lower alkyl group, a halogen atom, an amino group which may be substituted with a lower alkyl group, or a lower alkoxy group; a nitrogen-containing aromatic five- or six-membered heterocyclic group which is selected from a pyridyl group, an imidazolyl group, a pyrazinyl group, a pyrimidinyl group, a pyridazinyl group, a pyrazolyl group, a pyrrolyl group, a tetrazolyl group, a triazolyl group, a thiazolyl group and an oxazolyl group and which may be substituted with a lower alkyl group, a halogen atom, an amino group which may be substituted with a lower alkyl group, or a lower alkoxy group; a nitrogen-containing saturated five- to eight-membered heterocyclic group which is selected from a pyrrolidinyl group, a piperidyl group, a piperazinyl group, an imidazolidinyl group, a homopiperazinyl group, a pyrazolidinyl group, an azabicyclo{2.2.2}octyl group, an azabicyclo{2.2.1}heptyl group and an azabicyclo{3.2.1}octyl group and which may have a bridge and which may be substituted with a lower alkyl group on the nitrogen atom of the ring; or a group represented by

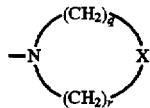

where the N atom in the formula may be oxidized, wherein q and r: 1, 2 or 3 and q+r=3 to 5, X: O or $S(O)_w$, w: 0, 1 or 2, and $R^7$ is a phenyl group which may have 1 to 5 substituents; a naphthyl group which may be substituted with a lower alkyl group; or an aromatic five- or six-membered heterocyclic group which is selected from a thienyl group, a furyl group, a pyrrolyl group, a pyridyl group, an imidazolyl group, a pyrazinyl group, a pyrimidinyl group, a pyranyl group, a pyridazinyl group, a pyrazolyl group, a tetrazolyl group, a triazolyl group, a thiazolyl group, an isothiazolyl group, an oxazolyl group and an isoxazolyl group, and which may be substituted with a lower alkyl group, a halogen atom, an amino group which may be substituted with a lower alkyl group, or a lower alkoxy group; in which each of the substituents for the phenyl group of $R^7$ is selected from:

(a) a lower alkyl group, a lower alkenyl group or a lower alkynyl group which groups may be substituted with a halogen atom or a hydroxyl group, (b) a lower alkoxy group which may be substituted with a halogen atom, a cyano group, a hydroxyl group, a carboxyl group, a lower alkoxycarbonyl group, a lower alkanoyl group, a lower alkanoyloxy group, a carbamoyl group, a lower alkylaminocarbonyl group or a phthalimide group; a hydroxyl group; a mercapto group; or a lower alkylthio group, (c) a halogen atom, a cyano group, or a nitro group, (d) a carboxyl group; a lower alkoxycarbonyl group; a lower alkanoyl group; a lower alkanoyloxy group; a carbamoyl group; or a lower alkylaminocarbonyl group, (e) an amino group which may be substituted with a lower alkyl group; a lower alkanoylamino group; a 1-pyrrodinyl group; a piperidino group; a morpholino group; or a piperazinyl, imidazolidinyl or homopiperazinyl group which may be substituted with a lower alkyl group on the nitrogen atom of the ring, (f) a cycloalkyl group, (g) a phenyl group which may be substituted with a lower alkyl group, a lower alkenyl group, a lower alkynyl group, a halogen atom, a lower alkoxy group, an amino group which my be substituted with a lower alkyl group, a hydroxyl group or a carboxyl group, and (h) an imidazolyl, triazolyl, tetrazolyl, pyrrolyl, pyridyl, pyrazinyl or pyrimidinyl group, which may be substituted with a lower alkyl group, a cycloalkyl group or a phenyl group.

3. The compound as claimed in claim 2, or a pharmaceutically acceptable salt thereof, wherein the group represented by

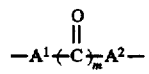

is selected from (1) a single bond, (2)

and (3) a lower alkylene group or a lower alkenylene group, and $R^8$ is a hydrogen atom; a cyano group; a carboxyl group; a lower alkoxycarbonyl group; a lower alkyl group; a lower alkenyl group; a cycloalkyl group; a hydroxyl group; a lower alkoxy group; a phenyl group which may be substituted with a lower alkyl group or a halogen atom; a nitrogen-containing aromatic five- or six-membered cyclic group which is selected from a pyridyl group, an imidazolyl group, a triazolyl group, a thiazolyl group and an oxazolyl group and which may be substituted with a lower alkyl group or with an amino group which may be substituted with a lower alkyl group; a nitrogen-containing saturated five- to eight-membered cyclic group which is selected from a pyrrolidinyl group, a piperidyl group, a homopiperazinyl group, an azabicyclic{2.2.2} octyl group and an azabicyclo{3.2.1}octyl group, which may have a bridge, and which may be substituted with a lower alkyl group on the nitrogen atom of the ring; or a group represented by

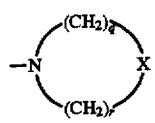

where the N atom in the formula may be oxidized, wherein q and r: 1, 2 or 3 and q+r=3 to 5, X: O or S(O)$_w$, w: 0, 1 or 2, and $R^7$ is a phenyl group which may have 1 to 5 substituents; a naphthyl group; or an aromatic five- or six-membered heterocyclic group which is selected from a thienyl group, a furyl group, a pyrrolyl group, a pyridyl group, an imidazolyl group, a triazolyl group, a thiazolyl group and an oxazolyl group and which may be substituted with an alkyl group; in which each of the substituents for the phenyl group of $R^7$ is selected from:

(a) a lower alkyl, lower alkenyl or lower alkynyl group, which groups may be substituted with a halogen atom or a hydroxyl group, (b) a lower alkoxy group which may be substituted with a hydroxyl group, a carboxyl group or a carbamoyl group; or a lower alkylthio group, (c) a halogen atom, or a nitro group, (e) an amino group which may be substituted with a lower alkyl group; a 1-pyrrodinyl group; a piperidino group; a morpholino group; or a piperazinyl or homopiperazinyl group which groups may be substituted with a lower alkyl group on the nitrogen atom of the ring, (g) a phenyl group which may be substituted with a lower alkyl group, a lower alkoxy group, an amino group which may be substituted with a lower alkyl group, or a hydroxyl group, and (h) an imidazolyl, triazolyl or pyrrolyl group, which may be substituted with a lower alkyl group, a cycloalkyl group or a phenyl group.

4. The compound as claimed in claim 3, or a pharmaceutically acceptable salt thereof, wherein when the group represented by

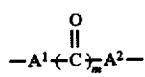

is (1) a single bond, then p is 0, and $R^8$ is a cyano group, a carboxyl group or a lower alkoxycarbonyl group, or (2)

or (3) a lower alkylene group or a lower alkenylene group, then p is 0, 1 or 2, and $R^8$ is a hydrogen atom; a lower alkyl group; a lower alkenyl group; a hydroxyl group; a lower alkoxy group; a phenyl group which may be substituted with a lower alkyl group or a halogen atom; a nitrogen-containing aromatic five- or six-membered heterocyclic group which is selected from a pyridyl group, an imidazolyl group, a triazolyl group, a thiazolyl group and an oxazolyl group and which may be substituted with a lower alkyl group or with an amino group which may be substituted with a lower alkyl group; a nitrogen-containing saturated five- to eight-membered heterocyclic group which is selected from a pyrrolidinyl group, a piperidyl group, a homopiperazinyl group, an azabicyclo{2.2.2}octyl group and an azabicyclo{3.2.1}octyl group, which may have a bridge, and which may be substituted with a lower alkyl group on the nitrogen atom of the ring; or a group represented by

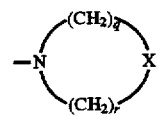

where the N atom in the formula may be oxidized, wherein q and r: 1, 2 or 3 and q+r=3 to 5, X: O or S(O)$_w$, w: 0, 1 or 2, with the proviso that, when

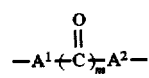

is

and p=0, $R^8$ represents

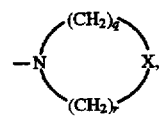

and when

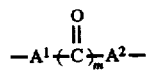

is a lower alkylene group and p=0, $R^8$ represents a hydroxyl group.

5. The compound as claimed in claim 4, or a pharmaceutically acceptable salt thereof, wherein (1) when the group represented by

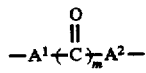

is a single bond, then

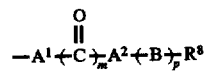

is —$R^{8a}$, wherein $R^{8a}$ is a cyano group, a carboxyl group or a lower alkoxycarbonyl group;

(2) when the group represented by

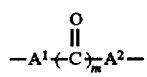

is

then

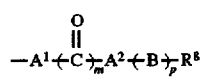

is

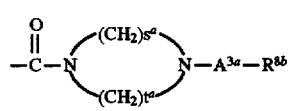 (2-1)

wherein
$S^a$ and $t^a$: 1, 2 or 3,
$s^a+t^a=3$ to 5,
$A^{3a}$: a single bond or a lower alkylene group, and
$R^{8b}$: a hydrogen atom, a lower alkyl group or a phenyl group;

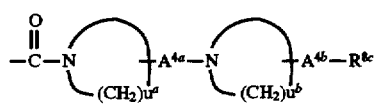 (2-2)

wherein
$u^a$ and $u^b$: 4, 5 or 6,
$A^{4a}$ and $A^{4b}$: each is a single bond, and
$R^{8c}$: a hydrogen atom;

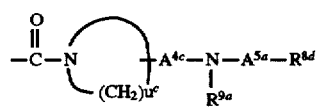 (2-3)

wherein
$u^c$: 4, 5 or 6,
$A^{4c}$ and $A^{5a}$: each is a single bond, and
$R^{9a}$ and $R^{8d}$: the same or different from each other and each represents a lower alkyl group;

 (2-4)

wherein
$u^d$: 1, 4, 5 or 6,
$A^{4d}$: a single bond, and
$R^{8e}$: a hydrogen atom;

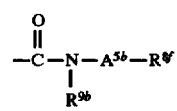 (2-5)

wherein
$R^{9b}$: a hydrogen atom or a lower alkyl group, $A^{5b}$: a single bond or a lower alkylene group, and
$R^{8f}$: a hydrogen atom, a cycloalkyl group, a phenyl group, a pyridyl group, a piperidyl group which may be substituted with a lower alkyl group on the nitrogen atom of the ring, a quinuclidine group, a hydroxyl group, a lower alkoxy group or a lower alkyl group;

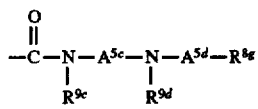 (2-6)

wherein
$A^{5c}$: a lower alkylene group,
$A^{5d}$: a single bond,
$R^{9c}$ and $R^{9d}$: the same or different from each other and each represents hydrogen atom or a lower alkyl group, and
$R^{8g}$: a hydrogen atom or a lower alkyl group; or

 (2-7)

$R^{8h}$: a group represented by a formula

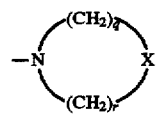

wherein q and r: 1, 2 or 3 and q+r=3 to 5, X: O or $S(O)_w$, and w: 0, 1 or 2; or (3) when the group represented by

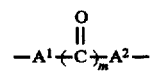

is a lower alkylene group or a lower alkenylene group, then

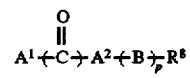

is

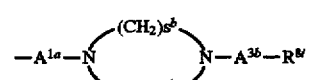 (3-1)

wherein
$A^{1a}$: a lower alkylene group,
$s^b$ and $t^b$: 1, 2 or 3,
$s^b+t^b$: 3 to 5,
$A^{3b}$: a single bond, and
$R^{8i}$: a hydrogen atom or a lower alkyl group;

 (3-2)

wherein
$A^{1b}$: a lower alkylene group,
$u^e$: 4, 5 or 6,
$A^{4e}$: a single bond, and $R^{8j}$: a hydrogen atom;

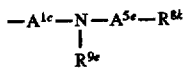

wherein $A^{1c}$: a lower alkylene group, $R^{8k}$ and $R^{9e}$: a hydrogen atom or a lower alkyl group, and $A^{5e}$: a single bond; or (3-4) —$A^{1d}$—$R^{8l}$ wherein $A^{1d}$: a lower alkylene group, and $R^{8l}$: a hydroxyl group.

6. The compound as claimed in claim 5, or a pharmaceutically acceptable salt thereof, wherein $R^7$ is a phenyl group which may be substituted with 1 to 3 substituents each selected from a lower alkyl group which may be substituted with a halogen atom, a lower alkoxy group which may be substituted with a carbamoyl group, a halogen atom, a piperidino group, a phenyl group which may be substituted with a lower alkyl group, an imidazolyl, triazolyl, or pyrrolyl group which may be substituted with a lower alkyl group; a naphthyl group; or a thienyl, furyl or pyrrolyl group which may be substituted with a lower alkyl group.

7. The compound as claimed in claim 6, or a pharmaceutically acceptable salt thereof, wherein the group represented by the formula

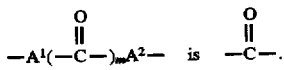

8. The compound as claimed in claim 1, or a pharmaceutically acceptable salt thereof, which is a Z form.

9. 4'-{(4,4-Difluoro-5-(4-methyl-1-piperazinyl) carbonylmethylene-2,3,4,5-tetrahydro-1H-1-benzazepin-1-yl) carbonyl}-2-phenylbenzanilide, 4'-{(4,4-difluoro-5-((1-piperazinylcarbonyl)methylene)-2,3,4-5-tetrahydro-1H-1-benzazepin-1-yl)carbonyl}-2-phenylbenzanilide, 4'-{(4,4-difluoro-5-((4-dimethylaminopiperidino)carbonyl) methylene)-2,3,4,5-tetrahydro-1H-1-benzazepin-1-yl) carbonyl}-2-phenylbenzanilide, 4'-{(4,4-difluoro-5-((4-methylhexahydro-1,4-diazepin-1-yl)carbonyl)methylene)-2, 3,4,5-tetrahydro-1H-1-benzazepin-1-yl)carbonyl)-2-phenylbenzanilide, 4'-{(5-(hexahydro-1,4-diazepin-1 -yl) carbonyl)methylene)-4,4-difluoro-2,3,4,5-tetrahydro-1H-1-benzazepin-1-yl)carbonyl}-2-phenylbenzanilide, 4'-{(4,4-difluoro-5-((N-methyl-N-(1-methyl-4-piperidyl)carbamoyl) methylene)-2,3,4,5-tetrahydro-1H-1-benzazepin-1-yl) carbonyl}-2-phenylbenzanilide, 4'-{(4,4-difluoro-5-N-((3-quinuclidinyl)carbamoyl)methylene)-2,3,4,5-tetrahydro-1H-1-benzazepin-1-yl)carbonyl}-2-phenylbenzanilide, N-{4-((4,4-difluoro-5-(((4-dimethylaminopiperidino) carbonyl)methylene)-2,3,4,5-tetrahydro-1H-1-benzazepin-1-yl)carbonyl)phenyl}-3-methylthiophene-2-carboxyamide, 4'-{(4,4-difluoro-5-(N-isopropylcarbamoylmethylene)-2,3, 4,5-tetrahydro-1H-1-benzazepin-1-yl)carbonyl}-2-phenylbenzanilide, 4'-{(4,4-difluoro-5-(N-(2-methoxylethyl)carbamoylmethylene)-2,3,4,5-tetrahydro-1H-1-benzazepin-1-yl)carbonyl}-2-phenylbenzanilide, 4'{{4,4-difluoro-5-(N-isopropylcarbamoylmethylene)-2,3, 4,5-tetrahydro-1H-1-benzazepin-1-yl}carbonyl}-2-ethoxybenzanilide, or a pharmaceutically acceptable salt or an isomer thereof.

10. A pharmaceutical composition which comprises the compound as claimed in any one of claims 1 to 7 or 9 or a pharmaceutically acceptable salt thereof and a pharmaceutically acceptable carrier.

11. The pharmaceutical composition according to claim 10, wherein it is an arginine vasopressin antagonist.

12. A difluorobenzazepinone derivative represented by the following general formula (II) or a salt thereof

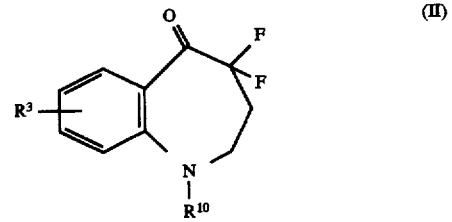

in the formula $R^3$ represents a hydrogen atom; a halogen atom; a lower alkyl group; a lower alkoxy group; or an amino group which may be substituted with a lower alkyl group, and $R^{10}$ represents a hydrogen atom or a protecting group for the amino group.

13. An aminobenzoyldifluorobenzazepinone derivative represented by the following general formula (III) or a salt thereof:

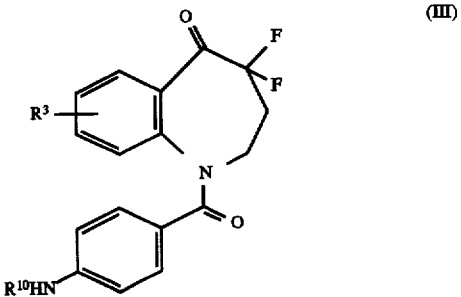

in the formula, $R^3$ represents a hydrogen atom; a halogen atom; a lower alkyl group; a lower alkoxy group; or an amino group which may be substituted with a lower alkyl group, and $R^{10}$ represents a hydrogen atom or a protecting group for the amino group.

* * * * *